United States Patent [19]
Dalla-Favera et al.

[11] Patent Number: 5,882,858
[45] Date of Patent: Mar. 16, 1999

[54] CLONING AND USES OF THE GENETIC LOCUS BCL-6

[75] Inventors: Riccardo Dalla-Favera; Raju S. K. Chaganti, both of New York, N.Y.

[73] Assignees: The Trustees of Columbia University in the City of New York; Sloan-Kettering Institute for Cancer Research, both of New York, N.Y.

[21] Appl. No.: 553,541

[22] PCT Filed: Jun. 9, 1994

[86] PCT No.: PCT/US94/06669

§ 371 Date: May 28, 1996

§ 102(e) Date: May 28, 1996

[87] PCT Pub. No.: WO94/29343

PCT Pub. Date: Dec. 22, 1994

Related U.S. Application Data

[63] Continuation-in-part of Ser. No. 74,967, Jun. 9, 1993, Pat. No. 5,641,672.

[51] Int. Cl.$^6$ .............................. C12Q 1/68; C07H 21/04
[52] U.S. Cl. .............................. 435/6; 435/7.24; 436/813; 536/24.31; 935/19; 935/21; 935/78
[58] Field of Search ...................... 435/6, 7.24; 436/813; 536/24.31; 935/19, 21, 78

[56] References Cited

U.S. PATENT DOCUMENTS

| | | | |
|---|---|---|---|
| 5,015,568 | 5/1991 | Tsujimoto et al. | 435/5 |
| 5,149,628 | 9/1992 | Croce et al. | 435/6 |

OTHER PUBLICATIONS

Sambrook et al. Molecular Cloning: A Laboratory Manual Second Edition vols. 1, 2 and 3. Cold Spring Harbor Laboratory Press: Cold Spring Harbor, New York, U.S.A. Nov., 1989.

Otsuki T; Yano T; Clark H M; Bastard C; Kerckaert J P; Jaffe E S; Raffeld M. Analysis of LAZ3 (BCL–6) status in B–cell non–Hodgkins's lymphomas: results of rearrangement and gene expression studies and a mutational analysis of coding region sequences. B May 1995.

Baron, B.W., et al. (1993) "Identification of the gene associated with the recurring chromosomal translocations t(3;14) (q27;q32) and t(3;22) (q27;q11) in B–cell lymphomas." *Proc. Natl. Acad. Sci.* 90: 5262–5266.

Bastard, C. et al. (1992) "Translocations involving band 3q27 and Ig gene regions in non–Hodgkin's lymphoma." *Blood* 79: 2527–2531.

Cleary, M.L. and J. Sklar (1985) "Nucleotide sequence of a t(14;18) chromosomal breakpoint in follicular lymphoma and demonstration of a breakpoint–cluster region near a transcriptionally active locus on chromosome 18." *Proc. Natl. Acad. Sci.* 82:7439–7443.

Kerckaert, J.–P., et al. (1993) "LAZ3, a novel zinc–finger encoding gene, is disrupted by recurring chromosome 3q27 translocations in human lymphomas." *Nature Genetics* 5:66–70 (Exhibit B).

Offit, K., et al., (1989) "A novel translocation associated with diffuse non–Hodgkin's lymphoma." *Blood* 74:1876–1879.

Rosati, M., et al. (1991) "Members of the zinc finger protein gene family sharing a conserved N–terminal module." *Nuc. Acids Res.* 19:5661–5667.

Van Cong, N., et al. (1989) "The human homologues of Fim1,Fim2/c–Fms, and Fim3, three retroviral integration regions involved in mouse myeloblastic leukemias, are respectively located on chromosomes 6p23, 5q33, and 3q27." *Human Genet* 81:257–263.

Ye, B.H., et al. (1993) "Cloning of bcl–6, the locus involved in chromosome translocations affecting band 3q27 in B–cell lymphoma." *Cancer Research* 53:2732–2735.

Ye, B.H. et al. (1993) "Alterations of a zinc finger–encoding gene, BCL–6, in diffuse large–cell lymphoma." *Science* 262:747–750 (Exhibit C).

*Primary Examiner*—Elizabeth C. Kemmerer
*Assistant Examiner*—David S. Romeo
*Attorney, Agent, or Firm*—John P. White; Cooper & Dunham LLP

[57] ABSTRACT

This invention provides a method for detecting a rearrangement of a bcl-6 gene in B-cell lymphoma in a subject, comprising: (a) obtaining a DNA sample from the subject; (b) cleaving the DNA sample into fragments; (c) separating the DNA fragments by size fractionation; (d) hybridizing the DNA fragments with a nucleic acid molecule comprising at least 15 contiguous nucleotides which is complementary to a sequence of an isolated nucleic acid molecule having the nucleic acid sequence as set forth in SEQ ID NO:1 and specifically hybridizes with the nucleic acid sequence as set forth in SEQ ID NO:1 to detect the DNA fragment containing the bcl-6 nucleic acid sequence; and (e) comparing the detected DNA fragment from (d) with a DNA fragment from a known normal subject, the difference in size of the fragments indicating occurrence of a rearrangement of the bcl-6 gene in B-cell lymphoma in the subject. This invention also provides a method for detecting a rearrangement of a bcl-6 gene in B-cell lymphoma in a subject, comprising: (a) obtaining an RNA sample from the subject; (b) separating the RNA sample into different species by size fractionation; (c) hybridizing the RNA species with a nucleic acid molecule comprising at least 15 contiguous nucleotides which is complementary to a sequence of an isolated nucleic acid molecule having the nucleic acid sequence as set forth in SEQ ID NO:1 and specifically hybridizes with the nucleic acid sequence as set forth in SEQ ID NO:1 to detect the RNA species containing bcl-6 nucleic acid sequence; and (d) comparing the detected RNA species from step (c) with the RNA species from a known normal subject, the difference in size of the species indicating the rearrangement of the bcl-6 gene in B-cell lymphoma in the subject.

11 Claims, 23 Drawing Sheets

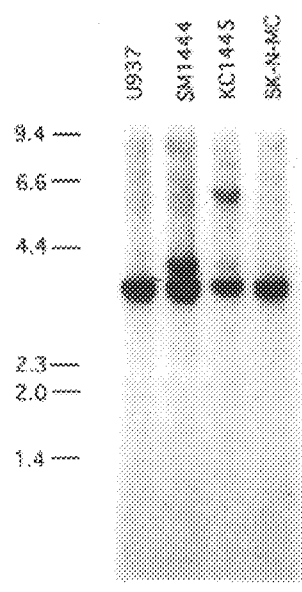
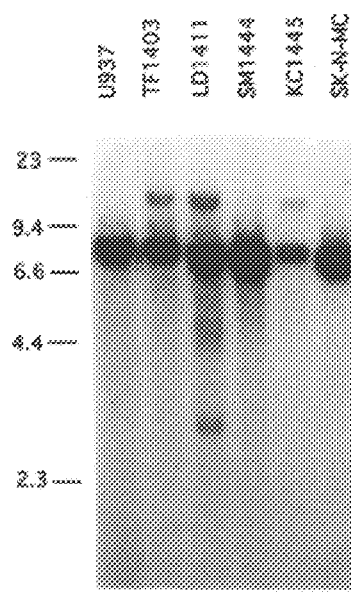
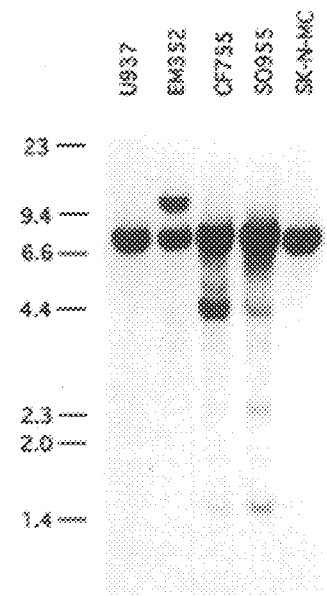

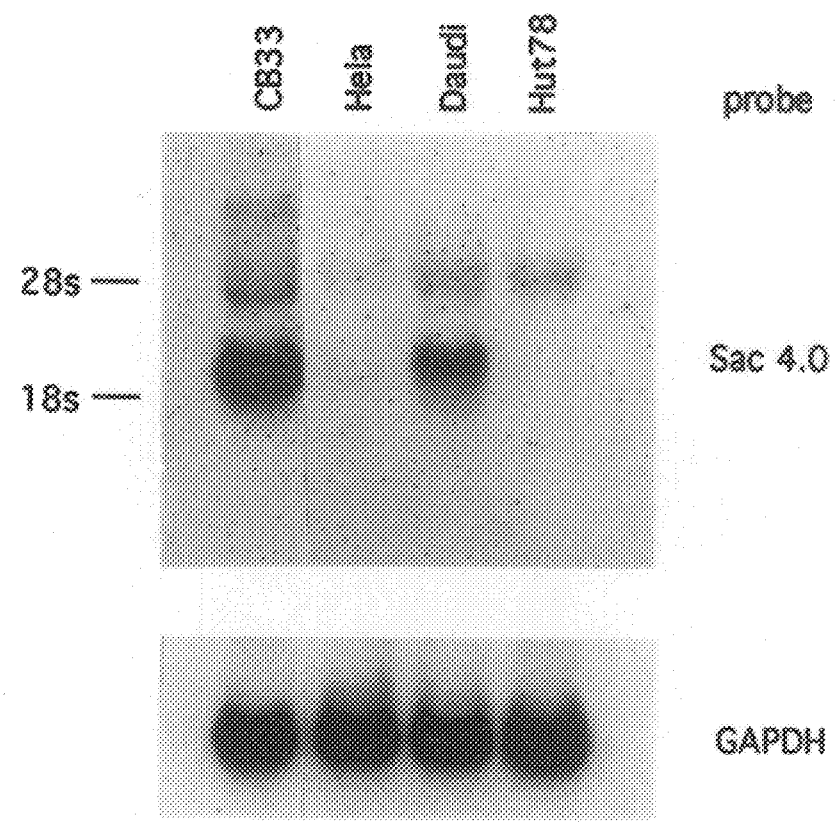

Map of Human BCL-6 Locus

Lambda-SM71 = a recombinant Lambda phage clone containing Bcl-6 breakpoint
H = Hind III
R = EcoR I
S = Sac I
X = Xho I

FIG. 9A
SEQ ID NOS:1-2

| | | | | | |
|---|---|---|---|---|---|
| GGCCCCTCGA | GCCTCGAACC | GGAACCTCCA | AATCCGAGAC | GCTCTGCTTA | TGAGGACCTC | 60 |
| GAAATATGCC | GGCCAGTGAA | AAAATCTTAT | GGCTTTGAGG | GCTTTTGGTT | GGCCAGGGGC | 120 |
| AGTAAAAATC | TCGGAGAGCT | GACACCAAGT | CCTCCCCTGC | CACGTAGCAG | TGGTAAAGTC | 180 |
| CGAAGCTCAA | ATTCCGAGAA | TTGAGCTCTG | TTGATTCTTA | GAACTGGGGT | TCTTAGAAGT | 240 |
| GGTGATGCAA | GAAGTTTCTA | GGAAAGGCCG | GACACCAGGT | TTTGAGCAAA | ATTTTGGACT | 300 |

```
GTGAAGCAAG GCATTGGTGA AGACAAA ATG GCC TCG CCG GCT GAC AGC TGT        351
                                Met Ala Ser Pro Ala Asp Ser Cys
                                 1               5

ATC CAG TTC ACC CGC CAT GCC AGG GAT GTT CTT CTC AAC CTT AAT CGT      399
Ile Gln Phe Thr Arg His Ala Arg Asp Val Leu Leu Asn Leu Asn Arg
        10              15                      20

CTC CGG AGT CGA GAC ATC TTG ACT GAT GTT GTC ATT GTT GTG AGC CGT      447
Leu Arg Ser Arg Asp Ile Leu Thr Asp Val Val Ile Val Val Ser Arg
25              30                      35                      40

GAG CAG TTT AGA GCC CAT AAA ACG GTC CTC ATG GCC TGG AGA GGC CTG      495
Glu Gln Phe Arg Ala His Lys Thr Val Leu Met Ala Trp Arg Gly Leu
                    45                      50                      55

TTC TAT AGC ATC TTT ACA GAC CAG TTG AAA TGC AAC CTT AGT GTG ATC      543
Phe Tyr Ser Ile Phe Thr Asp Gln Leu Lys Cys Asn Leu Ser Val Ile
                60                      65                      70

AAT CTA GAT CCT GAG ATC AAC CCT GAG GGA TTC TGC ATC CTC CTG GAC      591
Asn Leu Asp Pro Glu Ile Asn Pro Glu Gly Phe Cys Ile Leu Leu Asp
            75                      80                      85

TTC ATG TAC ACA TCT CGG CTC AAT TTG CGG GAG GGC AAC ATC ATG GCT      639
Phe Met Tyr Thr Ser Arg Leu Asn Leu Arg Glu Gly Asn Ile Met Ala
        90                      95                     100

GTG ATG GCC ACG GCT ATG TAC CTG CAG ATG GAG CAT GTT GTG GAC ACT      687
Val Met Ala Thr Ala Met Tyr Leu Gln Met Glu His Val Val Asp Thr
105                    110                     115                    120

TGC CGG AAG TTT ATT AAG GCC AGT GAA GCA GAG ATG GTT TCT GCC ATC      735
Cys Arg Lys Phe Ile Lys Ala Ser Glu Ala Glu Met Val Ser Ala Ile
                    125                     130                     135

AAG CCT CCT CGT GAA GAG TTC CTC AAC AGC CGG ATG CTG ATG CCC CAA      783
Lys Pro Pro Arg Glu Glu Phe Leu Asn Ser Arg Met Leu Met Pro Gln
                140                     145                     150

GAC ATC ATG GCC TAT CGG GGT CGT GAG GTG GTG GAG AAC AAC CTG CCA      831
Asp Ile Met Ala Tyr Arg Gly Arg Glu Val Val Glu Asn Asn Leu Pro
            155                     160                     165

CTG AGG AGC GCC CCT GGG TGT GAG AGC AGA GCC TTT GCC CCC AGC CTG      879
Leu Arg Ser Ala Pro Gly Cys Glu Ser Arg Ala Phe Ala Pro Ser Leu
        170                     175                     180
```

FIG. 9B

| | | | | | | | | | | | | | | | | |
|---|---|---|---|---|---|---|---|---|---|---|---|---|---|---|---|---|
| TAC | AGT | GGC | CTG | TCC | ACA | CCG | CCA | GCC | TCT | TAT | TCC | ATG | TAC | AGC | CAC | 927 |
| Tyr | Ser | Gly | Leu | Ser | Thr | Pro | Pro | Ala | Ser | Tyr | Ser | Met | Tyr | Ser | His | |
| 185 | | | | 190 | | | | | 195 | | | | | | 200 | |
| CTC | CCT | GTC | AGC | AGC | CTC | CTC | TTC | TCC | GAT | GAG | GAG | TTT | CGG | GAT | GTC | 975 |
| Leu | Pro | Val | Ser | Ser | Leu | Leu | Phe | Ser | Asp | Glu | Glu | Phe | Arg | Asp | Val | |
| | | | | 205 | | | | | 210 | | | | | 215 | | |
| CGG | ATG | CCT | GTG | GCC | AAC | CCC | TTC | CCC | AAG | GAG | CGG | GCA | CTC | CCA | TGT | 1023 |
| Arg | Met | Pro | Val | Ala | Asn | Pro | Phe | Pro | Lys | Glu | Arg | Ala | Leu | Pro | Cys | |
| | | | 220 | | | | | 225 | | | | | 230 | | | |
| GAT | AGT | GCC | AGG | CCA | GTC | CCT | GGT | GAG | TAC | AGC | CGG | CCG | ACT | TTG | GAG | 1071 |
| Asp | Ser | Ala | Arg | Pro | Val | Pro | Gly | Glu | Tyr | Ser | Arg | Pro | Thr | Leu | Glu | |
| | | 235 | | | | | 240 | | | | | 245 | | | | |
| GTG | TCC | CCC | AAT | GTG | TGC | CAC | AGC | AAT | ATC | TAT | TCA | CCC | AAG | GAA | ACA | 1119 |
| Val | Ser | Pro | Asn | Val | Cys | His | Ser | Asn | Ile | Tyr | Ser | Pro | Lys | Glu | Thr | |
| | 250 | | | | | 255 | | | | | 260 | | | | | |
| ATC | CCA | GAA | GAG | GCA | CGA | AGT | GAT | ATG | CAC | TAC | AGT | GTG | GCT | GAG | GGC | 1167 |
| Ile | Pro | Glu | Glu | Ala | Arg | Ser | Asp | Met | His | Tyr | Ser | Val | Ala | Glu | Gly | |
| 265 | | | | | 270 | | | | | 275 | | | | | 280 | |
| CTC | AAA | CCT | GCT | GCC | CCC | TCA | GCC | CGA | AAT | GCC | CCC | TAC | TTC | CCT | TGT | 1215 |
| Leu | Lys | Pro | Ala | Ala | Pro | Ser | Ala | Arg | Asn | Ala | Pro | Tyr | Phe | Pro | Cys | |
| | | | | 285 | | | | | 290 | | | | | 295 | | |
| GAC | AAG | GCC | AGC | AAA | GAA | GAA | GAG | AGA | CCC | TCC | TCG | GAA | GAT | GAG | ATT | 1263 |
| Asp | Lys | Ala | Ser | Lys | Glu | Glu | Glu | Arg | Pro | Ser | Ser | Glu | Asp | Glu | Ile | |
| | | | 300 | | | | | 305 | | | | | 310 | | | |
| GCC | CTG | CAT | TTC | GAG | CCC | CCC | AAT | GCA | CCC | CTG | AAC | CGG | AAG | GGT | CTG | 1311 |
| Ala | Leu | His | Phe | Glu | Pro | Pro | Asn | Ala | Pro | Leu | Asn | Arg | Lys | Gly | Leu | |
| | | 315 | | | | | 320 | | | | | 325 | | | | |
| GTT | AGT | CCA | CAG | AGC | CCC | CAG | AAA | TCT | GAC | TGC | CAG | CCC | AAC | TCG | CCC | 1359 |
| Val | Ser | Pro | Gln | Ser | Pro | Gln | Lys | Ser | Asp | Cys | Gln | Pro | Asn | Ser | Pro | |
| | 330 | | | | | 335 | | | | | 340 | | | | | |
| ACA | GAG | GCC | TGC | AGC | AGT | AAG | AAT | GCC | TGC | ATC | CTC | CAG | GGT | TCT | GGC | 1407 |
| Thr | Glu | Ala | Cys | Ser | Ser | Lys | Asn | Ala | Cys | Ile | Leu | Gln | Gly | Ser | Gly | |
| 345 | | | | | 350 | | | | | 355 | | | | | 360 | |
| TCC | CCT | CCA | GCC | AAG | AGC | CCC | ACT | GAC | CCC | AAA | GCC | TGC | AGC | TGG | AAG | 1455 |
| Ser | Pro | Pro | Ala | Lys | Ser | Pro | Thr | Asp | Pro | Lys | Ala | Cys | Ser | Trp | Lys | |
| | | | | 365 | | | | | 370 | | | | | 375 | | |
| AAA | TAC | AAG | TTC | ATC | GTG | CTC | AAC | AGC | CTC | AAC | CAG | AAT | GCC | AAA | CCA | 1503 |
| Lys | Tyr | Lys | Phe | Ile | Val | Leu | Asn | Ser | Leu | Asn | Gln | Asn | Ala | Lys | Pro | |
| | | | 380 | | | | | 385 | | | | | 390 | | | |
| GGG | GGG | CCT | GAG | CAG | GCT | GAG | CTG | GGC | CGC | CTT | TCC | CCA | CGA | GCC | TAC | 1551 |
| Gly | Gly | Pro | Glu | Gln | Ala | Glu | Leu | Gly | Arg | Leu | Ser | Pro | Arg | Ala | Tyr | |
| | | 395 | | | | | 400 | | | | | 405 | | | | |
| ACG | GCC | CCA | CCT | GCC | TGC | CAG | CCA | CCC | ATG | GAG | CCT | GAG | AAC | CTT | GAC | 1599 |
| Thr | Ala | Pro | Pro | Ala | Cys | Gln | Pro | Pro | Met | Glu | Pro | Glu | Asn | Leu | Asp | |
| | | 410 | | | | | 415 | | | | | 420 | | | | |

FIG. 9C

```
CTC CAG TCC CCA ACC AAG CTG AGT GCC AGC GGG GAG GAC TCC ACC ATC    1647
Leu Gln Ser Pro Thr Lys Leu Ser Ala Ser Gly Glu Asp Ser Thr Ile
425             430             435             440

CCA CAA GCC AGC CGG CTC AAT AAC ATC GTT AAC AGG TCC ATG ACG GGC    1695
Pro Gln Ala Ser Arg Leu Asn Asn Ile Val Asn Arg Ser Met Thr Gly
            445             450             455

TCT CCC CGC AGC AGC AGC GAG AGC CAC TCA CCA CTC TAC ATG CAC CCC    1743
Ser Pro Arg Ser Ser Ser Glu Ser His Ser Pro Leu Tyr Met His Pro
        460             465             470

CCG AAG TGC ACG TCC TGC GGC TCT CAG TCC CCA CAG CAT GCA GAG ATG    1791
Pro Lys Cys Thr Ser Cys Gly Ser Gln Ser Pro Gln His Ala Glu Met
        475             480             485

TGC CTC CAC ACC GCT GGC CCC ACG TTC GCT GAG GAG ATG GGA GAG ACC    1839
Cys Leu His Thr Ala Gly Pro Thr Phe Ala Glu Glu Met Gly Glu Thr
        490             495             500

CAG TCT GAG TAC TCA GAT TCT AGC TGT GAG AAC GGG GCC TTC TTC TGC    1887
Gln Ser Glu Tyr Ser Asp Ser Ser Cys Glu Asn Gly Ala Phe Phe Cys
505             510             515             520

AAT GAG TGT GAC TGC CGC TTC TCT GAG GAG GCC TCA CTC AAG AGG CAC    1935
Asn Glu Cys Asp Cys Arg Phe Ser Glu Glu Ala Ser Leu Lys Arg His
            525             530             535

ACG CTG CAG ACC CAC AGT GAC AAA CCC TAC AAG TGT GAC CGC TGC CAG    1983
Thr Leu Gln Thr His Ser Asp Lys Pro Tyr Lys Cys Asp Arg Cys Gln
        540             545             550

GCC TCC TTC CGC TAC AAG GGC AAC CTC GCC AGC CAC AAG ACC GTC CAT    2031
Ala Ser Phe Arg Tyr Lys Gly Asn Leu Ala Ser His Lys Thr Val His
        555             560             565

ACC GGT GAG AAA CCC TAT CGT TGC AAC ATC TGT GGG GCC CAG TTC AAC    2079
Thr Gly Glu Lys Pro Tyr Arg Cys Asn Ile Cys Gly Ala Gln Phe Asn
        570             575             580

CGG CCA GCC AAC CTG AAA ACC CAC ACT CGA ATT CAC TCT GGA GAG AAG    2127
Arg Pro Ala Asn Leu Lys Thr His Thr Arg Ile His Ser Gly Glu Lys
585             590             595             600

CCC TAC AAA TGC GAA ACC TGC GGA GCC AGA TTT GTA CAG GTG GCC CAC    2175
Pro Tyr Lys Cys Glu Thr Cys Gly Ala Arg Phe Val Gln Val Ala His
            605             610             615

CTC CGT GCC CAT GTG CTT ATC CAC ACT GGT GAG AAG CCC TAT CCC TGT    2223
Leu Arg Ala His Val Leu Ile His Thr Gly Glu Lys Pro Tyr Pro Cys
            620             625             630

GAA ATC TGT GGC ACC CGT TTC CGG CAC CTT CAG ACT CTG AAG AGC CAC    2271
Glu Ile Cys Gly Thr Arg Phe Arg His Leu Gln Thr Leu Lys Ser His
            635             640             645

CTG CGA ATC CAC ACA GGA GAG AAA CCT TAC CAT TGT GAG AAG TGT AAC    2319
Leu Arg Ile His Thr Gly Glu Lys Pro Tyr His Cys Glu Lys Cys Asn
        650             655             660
```

FIG. 9D

| | | | | | | | | | | | | | | |
|---|---|---|---|---|---|---|---|---|---|---|---|---|---|---|
| CTG | CAT | TTC | CGT | CAC | AAA | AGC | CAG | CTG | CGA | CTT | CAC | TTG | CGC | CAG AAG | 2367 |
| Leu | His | Phe | Arg | His | Lys | Ser | Gln | Leu | Arg | Leu | His | Leu | Arg | Gln Lys | |
| 665 | | | | | 670 | | | | | 675 | | | | 680 | |

| CAT | GGC | GCC | ATC | ACC | AAC | ACC | AAG | GTG | CAA | TAC | CGC | GTG | TCA | GCC | ACT | 2415 |
|---|---|---|---|---|---|---|---|---|---|---|---|---|---|---|---|---|
| His | Gly | Ala | Ile | Thr | Asn | Thr | Lys | Val | Gln | Tyr | Arg | Val | Ser | Ala | Thr | |
| | | | | 685 | | | | | 690 | | | | | 695 | | |

| GAC | CTG | CCT | CCG | GAG | CTC | CCC | AAA | GCC | TGC | TGAAGCATGG | AGTGTTGATG | 2465 |
|---|---|---|---|---|---|---|---|---|---|---|---|---|
| Asp | Leu | Pro | Pro | Glu | Leu | Pro | Lys | Ala | Cys | | | |
| | | | 700 | | | | | 705 | | | | |

CTTTCGTCTC CAGCCCCTTC TCAGAATCTA CCCAAAGGAT ACTGTAACAC TTTACAATGT 2525

TCATCCCATG ATGTAGTGCC TCTTTCATCC ACTAGTGCAA ATCATAGCTG GGGGTTGGGG 2585

GTGGTGGGGG TCGGGGCCTG GGGGACTGGG AGCCGCAGCA GCTCCCCCTC CCCCACTGCC 2645

ATAAAACATT AAGAAAATCA TATTGCTTCT TCTCCTATGT GNNNNNNNNN NNNNNNNNNN 2705

NNNNNNNNNN NNNNNNNNNN NNNNNNNNNN NNNNNNNNNN NNNNNNNNNN NNNNNNNNNN 2765

NNNNNNNNNN NNNNNNNNNN NNNNNNNNNN NNNNNNNNNN NNNNNNNNNN NNNNNNNNNN 2825

NNNNNNNNNN NNNNNNNNNN NNNNNNNNNN NNNNNNNNNN NNNNNNNNNN NNNNNNNNNN 2885

NNNNNNNNNN NNNNNNNNNN NNNNNNNNNN NNNNNNNNNN NNNNNNNNNN NNNNNNNNNN 2945

NNNNNNNNNN NNNNNNNNNN NNNNNNNNNN NNNNNNNNNN NNNNNNNNNN NNNNNNNNNN 3005

NNNNNNNNNN NNNNNNNNNN NNNNNNNNNN NNNNNNNNNN NNNNNNNNNN NNNNNNNNNN 3065

NNNNNNNNNN NNNNNNNNNN NNNNNNNNNN NNNNNNNNNN NNNNNNNNNN NNNNNNNNNN 3125

NNNNNNNNNN NNNNNNNNNN NNNNNNNNNN NNNNNNNNNN NNNNNNNNNN NNNNNNNNNN 3185

NNNNNNNNNN NNNNNNNNNN NNNNNNNNNN NNNNNNNNNN NNNNNNNNNN NNNNNNNNNN 3245

NTTTAAGTAT TGCATCTGTA TAAGTAAGAA AATATTTTGT CTAAAATGCC TCAGTGTATT 3305

TGTATTTTTT TGCAAGTGGG GGGTTACAAT TTACCCAGTG TGTATTAAAA AAAACCCAAA 3365

GAACCCAAAA ATCTCCAGAA GGAAAAATGT GTAATTTTGT TCTAGTTTTC AGTTTGTATA 3425

TACCCGTACA ACGTGTCCTC ACGGTGCCTT TTTTCACGGA AGTTTTCAAT GATGGGCGAG 3485

CGTGCACCAT CCCTTTTTGA AGTGTAGGCA GACACAGGGA CTTGAAGTTG TTACTAACTA 545

AACTCTCTTT GGGAATGTTT GTCTCATCCC ANTCTGCGTC ATGCTTGTGT GATAACTACT 3605

CCGGAGACAG GGTTTGGCTG TGTCTAAACT GCATTACCGC GTTGTAAAAA ATAGCTGTAC 3665

CAATATAAGA ATAAAATGTT GGAAAGTCGC AAAAAAAAAA AAAAAAAAA AAAAA 3720

FIG. 10B

```
  1 MASPADSCIQ FTRHASDVLL NLNRLRSRDI LTDVVIVVSR EQFRAHKTVL
 51 MACSGLFYSI FTDQLKCNLS VINLDPEINP EGFCILLDFM YTSRLNLREG
101 NIMAVMATAM YLQMEHVVDT CRKFIKASEA EMVSAIKPPR EEFLNSRMLM
151 PQDIMAYRGR EVVENNLPLR SAPGCESRAF APSLYSGLST PPASYSMYSH
201 LPVSSLLFSD EEFRDVRMPV ANPFPKERAL PCDSARPVPG EYSRPTLEVS
251 PNVCHSNIYS PKETIPEEAR SDMHYSVAEG LKPAAPSARN APYFPCDKAS
301 KEEERPSSED EIALHFEPPN APLNRKGLVS PQSPQKSDCQ PNSPTEACSS
351 KNACILQASG SPPAKSPTDP KACNWKKYKF IVLNSLNQNA KPGGPEQAEL
401 GRLSPRAYTA PPACQPPMEP ENLDLQSPTK LSASGEDSTI PQASRLNNIV
451 NRSMTGSPRS SSESHSPLYM HPPKCTSCGS QSPQHAEMCL HTAGPTFAEE
501 MGETQSEYSD SSCENGAFFC NECDCRFSEE ASLKRHTLQT HSDKPYKCDR
551 CQASFRYKGN LASHKTVHTG EKPYRCNICG AQFNRPANLK THTRIHSGEK
601 PYKCETCGAR FVQVAHLRAH VLIHTGEKPY PCEICGTRFR HLQTLKSHLR
651 IHTGEKPYHC EKCNLHFRHK SQLRLHLRQK HGAITNTKVQ YRVSATDLPP
701 ELPKAC*
```

FIG. 11

```
ZFPJS  (2-56)     DGSFVQHSVRVLQEINKQREKGQYCDATLDVGGLVFKAHWSVLACCSHFFQSLYG
KUP    (1-54)     .MDTASHSLVLQQLMQREFGFLCDCTVAIGDVYFKAHRAVLAAFSNYFKMIFI
VA55R  (1-51)     ...MNNSELIAVINGFRNSGRFCDISIVINDERINAHKLILSGASEYFSILFS
ttk    (9-63)     CLRWNHQSNLISVFDQLLHAETFTDVTLAVEGQHLKAHKNVLSACSPYFNILFV
kelch  (132-186)  QYSNEQHTARSFDAMNEMRKQKQELCDVILVADDVEIHAHRMVLASCSPYFYAMFI
PLZF   (10-63)    QLQNPSHPIGLLCKANQMRLAGTLCDVIMVDSQEFHAHRTVLACTSKMFEILF.
BCL-6  (8-62)     CLQFTRHASDVLLNRLRSRDILTDVIVVSREQFRAHKTVLMACSGLFYSIFL ZFPJS  (57-104)   DG..SGGSV.VLPAGF.AEIFGLLEDFFYTGHLATSGNRDQVLLAARELRV...
KUP    (55-107)   HQ..LSECIKIQPTDIQPDIFSYLLHIMYTGKGPKQIVDHSRLEEGIRFLHADYL
VA55R  (52-106)   NNFIDSNEYEVNLSHLDYQSVNDLIDYYIGIPLSTNDNVKYILSIADFLQIGSA
ttk    (64-116)   SH..PEKHPIVILKDVPYSDMKSLLDFMYRGEVSVDQERLTAFLRVAESLRIKGL
kelch  (187-240)  SFEESRQARITIQS.VDARALELLIDYVYTATVEVNEDNVQVLTAANLLQLTDV
PLZF   (64-114)   ...HRNSQHYTLDF.LSPKITQQILEYAYTATLQAKAEDLDDLLYAAEILEIEYL
BCL-6  (63-117)   DQLKCNLSVINLDFEINPEGFCILLDFMYTSRLNDREGNIMAVMATAMYLQMEHV
```

Black  
Gray

FIG. 13A
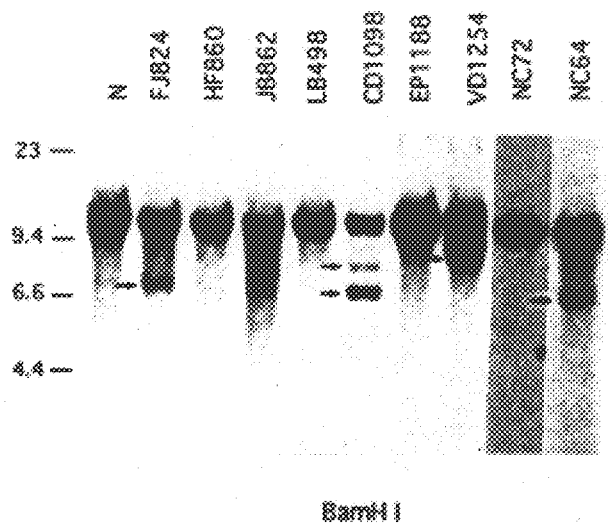
BamHI
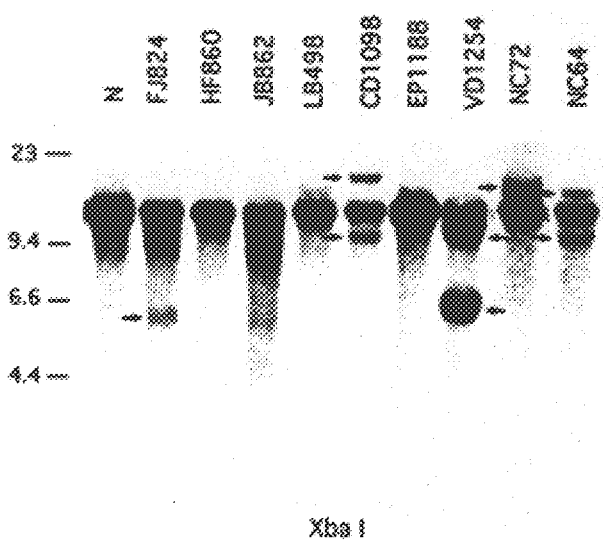
Xba I
FIG. 13B

Xba I

BamH I

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 3720 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 328..2445

( x i ) SEQUENCE DESCRIPTION: SEQ ID NO:1:

```
GGCCCCTCGA   GCCTCGAACC   GGAACCTCCA   AATCCGAGAC   GCTCTGCTTA   TGAGGACCTC        60

GAAATATGCC   GGCCAGTGAA   AAAATCTTAT   GGCTTTGAGG   GCTTTTGGTT   GGCCAGGGGC       120

AGTAAAAATC   TCGGAGAGCT   GACACCAAGT   CCTCCCCTGC   CACGTAGCAG   TGGTAAAGTC       180

CGAAGCTCAA   ATTCCGAGAA   TTGAGCTCTG   TTGATTCTTA   GAACTGGGGT   TCTTAGAAGT       240

GGTGATGCAA   GAAGTTTCTA   GGAAAGGCCG   GACACCAGGT   TTTGAGCAAA   ATTTTGGACT       300

GTGAAGCAAG   GCATTGGTGA   AGACAAA ATG GCC TCG CCG GCT GAC AGC TGT               351
                                Met Ala Ser Pro Ala Asp Ser Cys
                                  1               5

ATC CAG TTC ACC CGC CAT GCC AGG GAT GTT CTT CTC AAC CTT AAT CGT                 399
Ile Gln Phe Thr Arg His Ala Arg Asp Val Leu Leu Asn Leu Asn Arg
     10              15                  20

CTC CGG AGT CGA GAC ATC TTG ACT GAT GTT GTC ATT GTT GTG AGC CGT                 447
Leu Arg Ser Arg Asp Ile Leu Thr Asp Val Val Ile Val Val Ser Arg
 25              30                  35                  40

GAG CAG TTT AGA GCC CAT AAA ACG GTC CTC ATG GCC TGG AGA GGC CTG                 495
Glu Gln Phe Arg Ala His Lys Thr Val Leu Met Ala Trp Arg Gly Leu
                 45                  50                  55

TTC TAT AGC ATC TTT ACA GAC CAG TTG AAA TGC AAC CTT AGT GTG ATC                 543
Phe Tyr Ser Ile Phe Thr Asp Gln Leu Lys Cys Asn Leu Ser Val Ile
                 60                  65                  70

AAT CTA GAT CCT GAG ATC AAC CCT GAG GGA TTC TGC ATC CTC CTG GAC                 591
Asn Leu Asp Pro Glu Ile Asn Pro Glu Gly Phe Cys Ile Leu Leu Asp
             75                  80                  85

TTC ATG TAC ACA TCT CGG CTC AAT TTG CGG GAG GGC AAC ATC ATG GCT                 639
Phe Met Tyr Thr Ser Arg Leu Asn Leu Arg Glu Gly Asn Ile Met Ala
         90                  95                 100

GTG ATG GCC ACG GCT ATG TAC CTG CAG ATG GAG CAT GTT GTG GAC ACT                 687
Val Met Ala Thr Ala Met Tyr Leu Gln Met Glu His Val Val Asp Thr
105                 110                 115                 120

TGC CGG AAG TTT ATT AAG GCC AGT GAA GCA GAG ATG GTT TCT GCC ATC                 735
Cys Arg Lys Phe Ile Lys Ala Ser Glu Ala Glu Met Val Ser Ala Ile
                125                 130                 135
```

```
AAG  CCT  CCT  CGT  GAA  GAG  TTC  CTC  AAC  AGC  CGG  ATG  CTG  ATG  CCC  CAA      783
Lys  Pro  Pro  Arg  Glu  Glu  Phe  Leu  Asn  Ser  Arg  Met  Leu  Met  Pro  Gln
          140                      145                      150

GAC  ATC  ATG  GCC  TAT  CGG  GGT  CGT  GAG  GTG  GTG  GAG  AAC  AAC  CTG  CCA      831
Asp  Ile  Met  Ala  Tyr  Arg  Gly  Arg  Glu  Val  Val  Glu  Asn  Asn  Leu  Pro
               155                      160                      165

CTG  AGG  AGC  GCC  CCT  GGG  TGT  GAG  AGC  AGA  GCC  TTT  GCC  CCC  AGC  CTG      879
Leu  Arg  Ser  Ala  Pro  Gly  Cys  Glu  Ser  Arg  Ala  Phe  Ala  Pro  Ser  Leu
          170                      175                      180

TAC  AGT  GGC  CTG  TCC  ACA  CCG  CCA  GCC  TCT  TAT  TCC  ATG  TAC  AGC  CAC      927
Tyr  Ser  Gly  Leu  Ser  Thr  Pro  Pro  Ala  Ser  Tyr  Ser  Met  Tyr  Ser  His
185                      190                      195                      200

CTC  CCT  GTC  AGC  AGC  CTC  CTC  TTC  TCC  GAT  GAG  GAG  TTT  CGG  GAT  GTC      975
Leu  Pro  Val  Ser  Ser  Leu  Leu  Phe  Ser  Asp  Glu  Glu  Phe  Arg  Asp  Val
                    205                      210                      215

CGG  ATG  CCT  GTG  GCC  AAC  CCC  TTC  CCC  AAG  GAG  CGG  GCA  CTC  CCA  TGT     1023
Arg  Met  Pro  Val  Ala  Asn  Pro  Phe  Pro  Lys  Glu  Arg  Ala  Leu  Pro  Cys
               220                      225                      230

GAT  AGT  GCC  AGG  CCA  GTC  CCT  GGT  GAG  TAC  AGC  CGG  CCG  ACT  TTG  GAG     1071
Asp  Ser  Ala  Arg  Pro  Val  Pro  Gly  Glu  Tyr  Ser  Arg  Pro  Thr  Leu  Glu
          235                      240                      245

GTG  TCC  CCC  AAT  GTG  TGC  CAC  AGC  AAT  ATC  TAT  TCA  CCC  AAG  GAA  ACA     1119
Val  Ser  Pro  Asn  Val  Cys  His  Ser  Asn  Ile  Tyr  Ser  Pro  Lys  Glu  Thr
250                      255                      260

ATC  CCA  GAA  GAG  GCA  CGA  AGT  GAT  ATG  CAC  TAC  AGT  GTG  GCT  GAG  GGC     1167
Ile  Pro  Glu  Glu  Ala  Arg  Ser  Asp  Met  His  Tyr  Ser  Val  Ala  Glu  Gly
265                      270                      275                      280

CTC  AAA  CCT  GCT  GCC  CCC  TCA  GCC  CGA  AAT  GCC  CCC  TAC  TTC  CCT  TGT     1215
Leu  Lys  Pro  Ala  Ala  Pro  Ser  Ala  Arg  Asn  Ala  Pro  Tyr  Phe  Pro  Cys
                    285                      290                      295

GAC  AAG  GCC  AGC  AAA  GAA  GAA  GAG  AGA  CCC  TCC  TCG  GAA  GAT  GAG  ATT     1263
Asp  Lys  Ala  Ser  Lys  Glu  Glu  Glu  Arg  Pro  Ser  Ser  Glu  Asp  Glu  Ile
               300                      305                      310

GCC  CTG  CAT  TTC  GAG  CCC  CCC  AAT  GCA  CCC  CTG  AAC  CGG  AAG  GGT  CTG     1311
Ala  Leu  His  Phe  Glu  Pro  Pro  Asn  Ala  Pro  Leu  Asn  Arg  Lys  Gly  Leu
          315                      320                      325

GTT  AGT  CCA  CAG  AGC  CCC  CAG  AAA  TCT  GAC  TGC  CAG  CCC  AAC  TCG  CCC     1359
Val  Ser  Pro  Gln  Ser  Pro  Gln  Lys  Ser  Asp  Cys  Gln  Pro  Asn  Ser  Pro
330                      335                      340

ACA  GAG  GCC  TGC  AGC  AGT  AAG  AAT  GCC  TGC  ATC  CTC  CAG  GGT  TCT  GGC     1407
Thr  Glu  Ala  Cys  Ser  Ser  Lys  Asn  Ala  Cys  Ile  Leu  Gln  Gly  Ser  Gly
345                      350                      355                      360

TCC  CCT  CCA  GCC  AAG  AGC  CCC  ACT  GAC  CCC  AAA  GCC  TGC  AGC  TGG  AAG     1455
Ser  Pro  Pro  Ala  Lys  Ser  Pro  Thr  Asp  Pro  Lys  Ala  Cys  Ser  Trp  Lys
               365                      370                      375

AAA  TAC  AAG  TTC  ATC  GTG  CTC  AAC  AGC  CTC  AAC  CAG  AAT  GCC  AAA  CCA     1503
Lys  Tyr  Lys  Phe  Ile  Val  Leu  Asn  Ser  Leu  Asn  Gln  Asn  Ala  Lys  Pro
               380                      385                      390

GGG  GGG  CCT  GAG  CAG  GCT  GAG  CTG  GGC  CGC  CTT  TCC  CCA  CGA  GCC  TAC     1551
Gly  Gly  Pro  Glu  Gln  Ala  Glu  Leu  Gly  Arg  Leu  Ser  Pro  Arg  Ala  Tyr
          395                      400                      405

ACG  GCC  CCA  CCT  GCC  TGC  CAG  CCA  CCC  ATG  GAG  CCT  GAG  AAC  CTT  GAC     1599
Thr  Ala  Pro  Pro  Ala  Cys  Gln  Pro  Pro  Met  Glu  Pro  Glu  Asn  Leu  Asp
     410                      415                      420

CTC  CAG  TCC  CCA  ACC  AAG  CTG  AGT  GCC  AGC  GGG  GAG  GAC  TCC  ACC  ATC     1647
Leu  Gln  Ser  Pro  Thr  Lys  Leu  Ser  Ala  Ser  Gly  Glu  Asp  Ser  Thr  Ile
425                      430                      435                      440

CCA  CAA  GCC  AGC  CGG  CTC  AAT  AAC  ATC  GTT  AAC  AGG  TCC  ATG  ACG  GGC     1695
Pro  Gln  Ala  Ser  Arg  Leu  Asn  Asn  Ile  Val  Asn  Arg  Ser  Met  Thr  Gly
               445                      450                      455
```

-continued

| | | | | | | | | | | | | | | | | |
|---|---|---|---|---|---|---|---|---|---|---|---|---|---|---|---|---|
| TCT | CCC | CGC | AGC | AGC | AGC | GAG | AGC | CAC | TCA | CCA | CTC | TAC | ATG | CAC | CCC | 1743 |
| Ser | Pro | Arg | Ser | Ser | Ser | Glu | Ser | His | Ser | Pro | Leu | Tyr | Met | His | Pro | |
| | | | 460 | | | | | 465 | | | | | 470 | | | |
| CCG | AAG | TGC | ACG | TCC | TGC | GGC | TCT | CAG | TCC | CCA | CAG | CAT | GCA | GAG | ATG | 1791 |
| Pro | Lys | Cys | Thr | Ser | Cys | Gly | Ser | Gln | Ser | Pro | Gln | His | Ala | Glu | Met | |
| | | 475 | | | | | 480 | | | | | 485 | | | | |
| TGC | CTC | CAC | ACC | GCT | GGC | CCC | ACG | TTC | GCT | GAG | GAG | ATG | GGA | GAG | ACC | 1839 |
| Cys | Leu | His | Thr | Ala | Gly | Pro | Thr | Phe | Ala | Glu | Glu | Met | Gly | Glu | Thr | |
| | 490 | | | | | 495 | | | | | 500 | | | | | |
| CAG | TCT | GAG | TAC | TCA | GAT | TCT | AGC | TGT | GAG | AAC | GGG | GCC | TTC | TTC | TGC | 1887 |
| Gln | Ser | Glu | Tyr | Ser | Asp | Ser | Ser | Cys | Glu | Asn | Gly | Ala | Phe | Phe | Cys | |
| 505 | | | | | 510 | | | | | 515 | | | | | 520 | |
| AAT | GAG | TGT | GAC | TGC | CGC | TTC | TCT | GAG | GAG | GCC | TCA | CTC | AAG | AGG | CAC | 1935 |
| Asn | Glu | Cys | Asp | Cys | Arg | Phe | Ser | Glu | Glu | Ala | Ser | Leu | Lys | Arg | His | |
| | | | | 525 | | | | | 530 | | | | | 535 | | |
| ACG | CTG | CAG | ACC | CAC | AGT | GAC | AAA | CCC | TAC | AAG | TGT | GAC | CGC | TGC | CAG | 1983 |
| Thr | Leu | Gln | Thr | His | Ser | Asp | Lys | Pro | Tyr | Lys | Cys | Asp | Arg | Cys | Gln | |
| | | | 540 | | | | | 545 | | | | | 550 | | | |
| GCC | TCC | TTC | CGC | TAC | AAG | GGC | AAC | CTC | GCC | AGC | CAC | AAG | ACC | GTC | CAT | 2031 |
| Ala | Ser | Phe | Arg | Tyr | Lys | Gly | Asn | Leu | Ala | Ser | His | Lys | Thr | Val | His | |
| | | 555 | | | | | 560 | | | | | 565 | | | | |
| ACC | GGT | GAG | AAA | CCC | TAT | CGT | TGC | AAC | ATC | TGT | GGG | GCC | CAG | TTC | AAC | 2079 |
| Thr | Gly | Glu | Lys | Pro | Tyr | Arg | Cys | Asn | Ile | Cys | Gly | Ala | Gln | Phe | Asn | |
| 570 | | | | | 575 | | | | | 580 | | | | | | |
| CGG | CCA | GCC | AAC | CTG | AAA | ACC | CAC | ACT | CGA | ATT | CAC | TCT | GGA | GAG | AAG | 2127 |
| Arg | Pro | Ala | Asn | Leu | Lys | Thr | His | Thr | Arg | Ile | His | Ser | Gly | Glu | Lys | |
| 585 | | | | | 590 | | | | | 595 | | | | | 600 | |
| CCC | TAC | AAA | TGC | GAA | ACC | TGC | GGA | GCC | AGA | TTT | GTA | CAG | GTG | GCC | CAC | 2175 |
| Pro | Tyr | Lys | Cys | Glu | Thr | Cys | Gly | Ala | Arg | Phe | Val | Gln | Val | Ala | His | |
| | | | | 605 | | | | | 610 | | | | | 615 | | |
| CTC | CGT | GCC | CAT | GTG | CTT | ATC | CAC | ACT | GGT | GAG | AAG | CCC | TAT | CCC | TGT | 2223 |
| Leu | Arg | Ala | His | Val | Leu | Ile | His | Thr | Gly | Glu | Lys | Pro | Tyr | Pro | Cys | |
| | | | 620 | | | | | 625 | | | | | 630 | | | |
| GAA | ATC | TGT | GGC | ACC | CGT | TTC | CGG | CAC | CTT | CAG | ACT | CTG | AAG | AGC | CAC | 2271 |
| Glu | Ile | Cys | Gly | Thr | Arg | Phe | Arg | His | Leu | Gln | Thr | Leu | Lys | Ser | His | |
| | | 635 | | | | | 640 | | | | | 645 | | | | |
| CTG | CGA | ATC | CAC | ACA | GGA | GAG | AAA | CCT | TAC | CAT | TGT | GAG | AAG | TGT | AAC | 2319 |
| Leu | Arg | Ile | His | Thr | Gly | Glu | Lys | Pro | Tyr | His | Cys | Glu | Lys | Cys | Asn | |
| 650 | | | | | 655 | | | | | 660 | | | | | | |
| CTG | CAT | TTC | CGT | CAC | AAA | AGC | CAG | CTG | CGA | CTT | CAC | TTG | CGC | CAG | AAG | 2367 |
| Leu | His | Phe | Arg | His | Lys | Ser | Gln | Leu | Arg | Leu | His | Leu | Arg | Gln | Lys | |
| 665 | | | | | 670 | | | | | 675 | | | | | 680 | |
| CAT | GGC | GCC | ATC | ACC | AAC | ACC | AAG | GTG | CAA | TAC | CGC | GTG | TCA | GCC | ACT | 2415 |
| His | Gly | Ala | Ile | Thr | Asn | Thr | Lys | Val | Gln | Tyr | Arg | Val | Ser | Ala | Thr | |
| | | | | 685 | | | | | 690 | | | | | 695 | | |
| GAC | CTG | CCT | CCG | GAG | CTC | CCC | AAA | GCC | TGC | TGAAGCATGG | | | | AGTGTTGATG | | 2465 |
| Asp | Leu | Pro | Pro | Glu | Leu | Pro | Lys | Ala | Cys | | | | | | | |
| | | | 700 | | | | | 705 | | | | | | | | |

| | | | | | |
|---|---|---|---|---|---|
| CTTTCGTCTC | CAGCCCCTTC | TCAGAATCTA | CCCAAAGGAT | ACTGTAACAC | TTTACAATGT | 2525 |
| TCATCCCATG | ATGTAGTGCC | TCTTTCATCC | ACTAGTGCAA | ATCATAGCTG | GGGGTTGGGG | 2585 |
| GTGGTGGGGG | TCGGGGCCTG | GGGGACTGGG | AGCCGCAGCA | GCTCCCCCTC | CCCCACTGCC | 2645 |
| ATAAACATT | AAGAAAATCA | TATTGCTTCT | TCTCCTATGT | GNNNNNNNNN | NNNNNNNNNN | 2705 |
| NNNNNNNNNN | NNNNNNNNNN | NNNNNNNNNN | NNNNNNNNNN | NNNNNNNNNN | NNNNNNNNNN | 2765 |
| NNNNNNNNNN | NNNNNNNNNN | NNNNNNNNNN | NNNNNNNNNN | NNNNNNNNNN | NNNNNNNNNN | 2825 |
| NNNNNNNNNN | NNNNNNNNNN | NNNNNNNNNN | NNNNNNNNNN | NNNNNNNNNN | NNNNNNNNNN | 2885 |
| NNNNNNNNNN | NNNNNNNNNN | NNNNNNNNNN | NNNNNNNNNN | NNNNNNNNNN | NNNNNNNNNN | 2945 |

```
NNNNNNNNNN  NNNNNNNNNN  NNNNNNNNNN  NNNNNNNNNN  NNNNNNNNNN  NNNNNNNNNN       3 0 0 5

NNNNNNNNNN  NNNNNNNNNN  NNNNNNNNNN  NNNNNNNNNN  NNNNNNNNNN  NNNNNNNNNN       3 0 6 5

NNNNNNNNNN  NNNNNNNNNN  NNNNNNNNNN  NNNNNNNNNN  NNNNNNNNNN  NNNNNNNNNN       3 1 2 5

NNNNNNNNNN  NNNNNNNNNN  NNNNNNNNNN  NNNNNNNNNN  NNNNNNNNNN  NNNNNNNNNN       3 1 8 5

NNNNNNNNNN  NNNNNNNNNN  NNNNNNNNNN  NNNNNNNNNN  NNNNNNNNNN  NNNNNNNNNN       3 2 4 5

NTTTAAGTAT  TGCATCTGTA  TAAGTAAGAA  AATATTTTGT  CTAAAATGCC  TCAGTGTATT       3 3 0 5

TGTATTTTTT  TGCAAGTGGG  GGGTTACAAT  TTACCCAGTG  TGTATTAAAA  AAAACCCAAA       3 3 6 5

GAACCCAAAA  ATCTCCAGAA  GGAAAAATGT  GTAATTTTGT  TCTAGTTTTC  AGTTTGTATA       3 4 2 5

TACCCGTACA  ACGTGTCCTC  ACGGTGCCTT  TTTTCACGGA  AGTTTTCAAT  GATGGGCGAG       3 4 8 5

CGTGCACCAT  CCCTTTTTGA  AGTGTAGGCA  GACACAGGGA  CTTGAAGTTG  TTACTAACTA       3 5 4 5

AACTCTCTTT  GGGAATGTTT  GTCTCATCCC  ANTCTGCGTC  ATGCTTGTGT  GATAACTACT       3 6 0 5

CCGGAGACAG  GGTTTGGCTG  TGTCTAAACT  GCATTACCGC  GTTGTAAAAA  ATAGCTGTAC       3 6 6 5

CAATATAAGA  ATAAAATGTT  GGAAAGTCGC  AAAAAAAAAA  AAAAAAAAAA  AAAAA            3 7 2 0
```

( 2 ) INFORMATION FOR SEQ ID NO:2:

( i ) SEQUENCE CHARACTERISTICS:
        ( A ) LENGTH: 706 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ala  Ser  Pro  Ala  Asp  Ser  Cys  Ile  Gln  Phe  Thr  Arg  His  Ala  Arg
  1              5                        10                           15

Asp  Val  Leu  Leu  Asn  Leu  Asn  Arg  Leu  Arg  Ser  Arg  Asp  Ile  Leu  Thr
                 20                       25                       30

Asp  Val  Val  Ile  Val  Val  Ser  Arg  Gln  Phe  Arg  Ala  His  Lys  Thr
             35                       40                       45

Val  Leu  Met  Ala  Trp  Arg  Gly  Leu  Phe  Tyr  Ser  Ile  Phe  Thr  Asp  Gln
         50                       55                       60

Leu  Lys  Cys  Asn  Leu  Ser  Val  Ile  Asn  Leu  Asp  Pro  Glu  Ile  Asn  Pro
 65                       70                       75                       80

Glu  Gly  Phe  Cys  Ile  Leu  Leu  Asp  Phe  Met  Tyr  Thr  Ser  Arg  Leu  Asn
                 85                       90                       95

Leu  Arg  Glu  Gly  Asn  Ile  Met  Ala  Val  Ala  Thr  Ala  Met  Tyr  Leu
                100                      105                      110

Gln  Met  Glu  His  Val  Val  Asp  Thr  Cys  Arg  Lys  Phe  Ile  Lys  Ala  Ser
            115                      120                      125

Glu  Ala  Glu  Met  Val  Ser  Ala  Ile  Lys  Pro  Pro  Arg  Glu  Glu  Phe  Leu
        130                      135                      140

Asn  Ser  Arg  Met  Leu  Met  Pro  Gln  Asp  Ile  Met  Ala  Tyr  Arg  Gly  Arg
145                      150                      155                      160

Glu  Val  Val  Glu  Asn  Asn  Leu  Pro  Leu  Arg  Ser  Ala  Pro  Gly  Cys  Glu
                 165                      170                      175

Ser  Arg  Ala  Phe  Ala  Pro  Ser  Leu  Tyr  Ser  Gly  Leu  Ser  Thr  Pro  Pro
            180                      185                      190

Ala  Ser  Tyr  Ser  Met  Tyr  Ser  His  Leu  Pro  Val  Ser  Ser  Leu  Leu  Phe
            195                      200                      205

Ser  Asp  Glu  Glu  Phe  Arg  Asp  Val  Arg  Met  Pro  Val  Ala  Asn  Pro  Phe
        210                      215                      220
```

| | | | | | | | | | | | | | | |
|---|---|---|---|---|---|---|---|---|---|---|---|---|---|---|
| Pro 225 | Lys | Glu | Arg | Ala | Leu 230 | Pro | Cys | Asp | Ser 235 | Ala | Arg | Pro | Val | Pro 240 | Gly |
| Glu | Tyr | Ser | Arg | Pro 245 | Thr | Leu | Glu | Val | Ser 250 | Pro | Asn | Val | Cys | His 255 | Ser |
| Asn | Ile | Tyr | Ser 260 | Pro | Lys | Glu | Thr | Ile 265 | Pro | Glu | Glu | Ala | Arg 270 | Ser | Asp |
| Met | His | Tyr 275 | Ser | Val | Ala | Glu | Gly 280 | Leu | Lys | Pro | Ala | Ala 285 | Pro | Ser | Ala |
| Arg | Asn 290 | Ala | Pro | Tyr | Phe | Pro 295 | Cys | Asp | Lys | Ala | Ser 300 | Lys | Glu | Glu | Glu |
| Arg 305 | Pro | Ser | Ser | Glu | Asp 310 | Glu | Ile | Ala | Leu | His 315 | Phe | Glu | Pro | Pro | Asn 320 |
| Ala | Pro | Leu | Asn | Arg 325 | Lys | Gly | Leu | Val | Ser 330 | Pro | Gln | Ser | Pro | Gln 335 | Lys |
| Ser | Asp | Cys | Gln 340 | Pro | Asn | Ser | Pro | Thr 345 | Glu | Ala | Cys | Ser | Ser 350 | Lys | Asn |
| Ala | Cys | Ile 355 | Leu | Gln | Gly | Ser | Gly 360 | Ser | Pro | Pro | Ala | Lys 365 | Ser | Pro | Thr |
| Asp | Pro 370 | Lys | Ala | Cys | Ser | Trp 375 | Lys | Lys | Tyr | Lys | Phe 380 | Ile | Val | Leu | Asn |
| Ser 385 | Leu | Asn | Gln | Asn | Ala 390 | Lys | Pro | Gly | Gly | Pro 395 | Glu | Gln | Ala | Glu | Leu 400 |
| Gly | Arg | Leu | Ser | Pro 405 | Arg | Ala | Tyr | Thr | Ala 410 | Pro | Pro | Ala | Cys | Gln 415 | Pro |
| Pro | Met | Glu | Pro 420 | Glu | Asn | Leu | Asp | Leu 425 | Gln | Ser | Pro | Thr | Lys 430 | Leu | Ser |
| Ala | Ser | Gly | Glu 435 | Asp | Ser | Thr | Ile 440 | Pro | Gln | Ala | Ser | Arg 445 | Leu | Asn | Asn |
| Ile | Val 450 | Asn | Arg | Ser | Met | Thr 455 | Gly | Ser | Pro | Arg | Ser 460 | Ser | Ser | Glu | Ser |
| His 465 | Ser | Pro | Leu | Tyr | Met 470 | His | Pro | Pro | Lys | Cys 475 | Thr | Ser | Cys | Gly | Ser 480 |
| Gln | Ser | Pro | Gln | His 485 | Ala | Glu | Met | Cys | Leu 490 | His | Thr | Ala | Gly | Pro 495 | Thr |
| Phe | Ala | Glu | Glu 500 | Met | Gly | Glu | Thr | Gln 505 | Ser | Glu | Tyr | Ser | Asp 510 | Ser | Ser |
| Cys | Glu | Asn 515 | Gly | Ala | Phe | Phe | Cys 520 | Asn | Glu | Cys | Asp | Cys 525 | Arg | Phe | Ser |
| Glu | Glu 530 | Ala | Ser | Leu | Lys | Arg 535 | His | Thr | Leu | Gln | Thr 540 | His | Ser | Asp | Lys |
| Pro 545 | Tyr | Lys | Cys | Asp | Arg 550 | Cys | Gln | Ala | Ser | Phe 555 | Arg | Tyr | Lys | Gly | Asn 560 |
| Leu | Ala | Ser | His | Lys 565 | Thr | Val | His | Thr | Gly 570 | Glu | Lys | Pro | Tyr | Arg 575 | Cys |
| Asn | Ile | Cys | Gly 580 | Ala | Gln | Phe | Asn | Arg 585 | Pro | Ala | Asn | Leu | Lys 590 | Thr | His |
| Thr | Arg | Ile 595 | His | Ser | Gly | Glu | Lys 600 | Pro | Tyr | Lys | Cys | Glu 605 | Thr | Cys | Gly |
| Ala | Arg 610 | Phe | Val | Gln | Val | Ala 615 | His | Leu | Arg | Ala | His 620 | Val | Leu | Ile | His |
| Thr 625 | Gly | Glu | Lys | Pro | Tyr 630 | Pro | Cys | Glu | Ile | Cys 635 | Gly | Thr | Arg | Phe | Arg 640 |
| His | Leu | Gln | Thr | Leu | Lys | Ser | His | Leu | Arg | Ile | His | Thr | Gly | Glu | Lys |

```
                           645                          650                           655
Pro  Tyr  His  Cys  Glu  Lys  Cys  Asn  Leu  His  Phe  Arg  His  Lys  Ser  Gln
               660                      665                      670

Leu  Arg  Leu  His  Leu  Arg  Gln  Lys  His  Gly  Ala  Ile  Thr  Asn  Thr  Lys
               675                      680                      685

Val  Gln  Tyr  Arg  Val  Ser  Ala  Thr  Asp  Leu  Pro  Pro  Glu  Leu  Pro  Lys
               690                      695                      700

Ala  Cys
705
```

( 2 ) INFORMATION FOR SEQ ID NO:3:

( i ) SEQUENCE CHARACTERISTICS:
        ( A ) LENGTH: 103 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Asp  Gly  Ser  Phe  Val  Gln  His  Ser  Val  Arg  Val  Leu  Gln  Glu  Leu  Asn
1                   5                        10                       15

Lys  Gln  Arg  Glu  Lys  Gly  Gln  Tyr  Cys  Asp  Ala  Thr  Leu  Asp  Val  Gly
               20                      25                      30

Gly  Leu  Val  Phe  Lys  Ala  His  Trp  Ser  Val  Leu  Ala  Cys  Cys  Ser  His
          35                       40                      45

Phe  Phe  Gln  Ser  Leu  Tyr  Gly  Asp  Gly  Ser  Gly  Gly  Ser  Val  Val  Leu
     50                       55                      60

Pro  Ala  Gly  Phe  Ala  Glu  Ile  Phe  Gly  Leu  Leu  Leu  Asp  Phe  Phe  Tyr
65                       70                      75                           80

Thr  Gly  His  Leu  Ala  Leu  Thr  Ser  Gly  Asn  Arg  Asp  Gln  Val  Leu  Leu
               85                       90                           95

Ala  Ala  Arg  Glu  Leu  Arg  Val
               100
```

( 2 ) INFORMATION FOR SEQ ID NO:4:

( i ) SEQUENCE CHARACTERISTICS:
        ( A ) LENGTH: 107 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Met  Asp  Thr  Ala  Ser  His  Ser  Leu  Val  Leu  Leu  Gln  Gln  Leu  Asn  Met
1                   5                        10                       15

Gln  Arg  Glu  Phe  Gly  Phe  Leu  Cys  Asp  Cys  Thr  Val  Ala  Ile  Gly  Asp
               20                      25                      30

Val  Tyr  Phe  Lys  Ala  His  Arg  Ala  Val  Leu  Ala  Ala  Phe  Ser  Asn  Tyr
          35                       40                      45

Phe  Lys  Met  Ile  Phe  Ile  His  Gln  Thr  Ser  Glu  Cys  Ile  Lys  Ile  Gln
     50                       55                      60

Pro  Thr  Asp  Ile  Gln  Pro  Asp  Ile  Phe  Ser  Tyr  Leu  Leu  His  Ile  Met
65                       70                      75                           80

Tyr  Thr  Gly  Lys  Gly  Pro  Lys  Gln  Ile  Val  Asp  His  Ser  Arg  Leu  Glu
               85                       90                           95

Glu  Gly  Ile  Arg  Phe  Leu  His  Ala  Asp  Tyr  Leu
```

| | |
|---|---|
| 1 0 0 | 1 0 5 |

( 2 ) INFORMATION FOR SEQ ID NO:5:

( i ) SEQUENCE CHARACTERISTICS:
        ( A ) LENGTH: 106 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Met Asn Asn Ser Ser Glu Leu Ile Ala Val Ile Asn Gly Phe Arg Asn
1               5                   10                  15

Ser Gly Arg Phe Cys Asp Ile Ser Ile Val Ile Asn Asp Glu Arg Ile
                20                  25                  30

Asn Ala His Lys Leu Ile Leu Ser Gly Ala Ser Glu Tyr Phe Ser Ile
            35                  40                  45

Leu Phe Ser Asn Asn Phe Ile Asp Ser Asn Glu Tyr Glu Val Asn Leu
        50                  55                  60

Ser His Leu Asp Tyr Gln Ser Val Asn Asp Leu Ile Asp Tyr Ile Tyr
65                  70                  75                  80

Gly Ile Pro Leu Ser Leu Thr Asn Asp Asn Val Lys Tyr Ile Leu Ser
                85                  90                  95

Thr Ala Asp Phe Leu Gln Ile Gly Ser Ala
                100                 105
```

( 2 ) INFORMATION FOR SEQ ID NO:6:

( i ) SEQUENCE CHARACTERISTICS:
        ( A ) LENGTH: 108 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Cys Leu Arg Trp Asn Asn His Gln Ser Asn Leu Leu Ser Val Phe Asp
1               5                   10                  15

Gln Leu Leu His Ala Glu Thr Phe Thr Asp Val Thr Leu Ala Val Glu
                20                  25                  30

Gly Gln His Leu Lys Ala His Lys Asn Val Leu Ser Ala Cys Ser Pro
            35                  40                  45

Tyr Phe Asn Thr Leu Phe Val Ser His Pro Glu Lys His Pro Ile Val
        50                  55                  60

Ile Leu Lys Asp Val Pro Tyr Ser Asp Met Lys Ser Leu Leu Asp Phe
65                  70                  75                  80

Met Tyr Arg Gly Glu Val Ser Val Asp Gln Glu Arg Leu Thr Ala Phe
                85                  90                  95

Leu Arg Val Ala Glu Ser Leu Arg Ile Lys Gly Leu
                100                 105
```

( 2 ) INFORMATION FOR SEQ ID NO:7:

( i ) SEQUENCE CHARACTERISTICS:
        ( A ) LENGTH: 109 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

| Gln | Tyr | Ser | Asn | Glu | Gln | His | Thr | Ala | Arg | Ser | Phe | Asp | Ala | Met | Asn |
| 1 | | | | 5 | | | | | 10 | | | | | 15 | |
| Glu | Met | Arg | Lys | Gln | Lys | Gln | Leu | Cys | Asp | Val | Ile | Leu | Val | Ala | Asp |
| | | | 20 | | | | | 25 | | | | | 30 | | |
| Asp | Val | Glu | Ile | His | Ala | His | Arg | Met | Val | Leu | Ala | Ser | Cys | Ser | Pro |
| | | | 35 | | | | | 40 | | | | | 45 | | |
| Tyr | Phe | Tyr | Ala | Met | Phe | Thr | Ser | Phe | Glu | Glu | Ser | Arg | Gln | Ala | Arg |
| | | 50 | | | | | 55 | | | | | 60 | | | |
| Ile | Thr | Leu | Gln | Ser | Val | Asp | Ala | Arg | Ala | Leu | Glu | Leu | Leu | Ile | Asp |
| 65 | | | | | | 70 | | | | | 75 | | | | 80 |
| Tyr | Val | Tyr | Thr | Ala | Thr | Val | Glu | Val | Asn | Glu | Asp | Asn | Val | Gln | Val |
| | | | | 85 | | | | | 90 | | | | | 95 | |
| Leu | Leu | Thr | Ala | Ala | Asn | Leu | Leu | Gln | Leu | Thr | Asp | Val | | | |
| | | | 100 | | | | | 105 | | | | | | | |

( 2 ) INFORMATION FOR SEQ ID NO:8:

( i ) SEQUENCE CHARACTERISTICS:
        ( A ) LENGTH: 105 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

| Gln | Leu | Gln | Asn | Pro | Ser | His | Pro | Thr | Gly | Leu | Leu | Cys | Lys | Ala | Asn |
| 1 | | | | 5 | | | | | 10 | | | | | 15 | |
| Gln | Met | Arg | Leu | Ala | Gly | Thr | Leu | Cys | Asp | Val | Val | Ile | Met | Val | Asp |
| | | | 20 | | | | | 25 | | | | | 30 | | |
| Ser | Gln | Glu | Phe | His | Ala | His | Arg | Thr | Val | Leu | Ala | Cys | Thr | Ser | Lys |
| | | | 35 | | | | | 40 | | | | | 45 | | |
| Met | Phe | Glu | Ile | Leu | Phe | His | Arg | Asn | Ser | Gln | His | Tyr | Thr | Leu | Asp |
| | | 50 | | | | | 55 | | | | | 60 | | | |
| Phe | Leu | Ser | Pro | Lys | Thr | Phe | Gln | Gln | Ile | Leu | Glu | Tyr | Ala | Tyr | Thr |
| 65 | | | | | | 70 | | | | | 75 | | | | 80 |
| Ala | Thr | Leu | Gln | Ala | Lys | Ala | Glu | Asp | Leu | Asp | Asp | Leu | Leu | Tyr | Ala |
| | | | | 85 | | | | | 90 | | | | | 95 | |
| Ala | Glu | Ile | Leu | Glu | Ile | Glu | Tyr | Leu | | | | | | | |
| | | | 100 | | | | | 105 | | | | | | | |

( 2 ) INFORMATION FOR SEQ ID NO:9:

( i ) SEQUENCE CHARACTERISTICS:
        ( A ) LENGTH: 110 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

| Cys | Leu | Gln | Phe | Thr | Arg | His | Ala | Ser | Asp | Val | Leu | Leu | Asn | Leu | Asn |
| 1 | | | | 5 | | | | | 10 | | | | | 15 | |
| Arg | Leu | Arg | Ser | Arg | Asp | Ile | Leu | Thr | Asp | Val | Val | Ile | Val | Val | Ser |
| | | | 20 | | | | | 25 | | | | | 30 | | |
| Arg | Glu | Gln | Phe | Arg | Ala | His | Lys | Thr | Val | Leu | Met | Ala | Cys | Ser | Gly |
| | | | 35 | | | | | 40 | | | | | 45 | | |

-continued

| Leu | Phe 50 | Tyr | Ser | Ile | Phe | Thr 55 | Asp | Gln | Leu | Lys | Cys 60 | Asn | Leu | Ser | Val |
| Ile 65 | Asn | Leu | Asp | Pro | Glu 70 | Ile | Asn | Pro | Glu | Gly 75 | Phe | Cys | Ile | Leu | Leu 80 |
| Asp | Phe | Met | Tyr | Thr 85 | Ser | Arg | Leu | Asn | Leu 90 | Arg | Glu | Gly | Asn | Ile 95 | Met |
| Ala | Val | Met | Ala 100 | Thr | Ala | Met | Tyr | Leu 105 | Gln | Met | Glu | His | Val 110 | | |

CLONING AND USES OF THE GENETIC LOCUS BCL-6

This application is a continuation-in-part U.S. application Ser. No. 08/074,967, filed on Jun. 9, 1993 and issued as U.S. Pat. No. 5,641,672 on Jun. 24, 1997, the contents of which are hereby incorporated by reference.

The invention disclosed herein was made with Government support under NIH Grant Nos. CA-44029, CA-34775, CA-08748 and CA-37295 from the Department of Health and Human Services. Accordingly, the U.S. Government has certain rights in this invention.

BACKGROUND OF THE INVENTION

Throughout this application various references are referred to within parenthesis. Disclosures of these publications in their entireties are hereby incorporated by reference into this application to more fully describe the state of the art to which this invention pertains. Full bibliographic citation for these references may be found at the end of each Experimental Detail Section.

Non-random chromosomal abnormalities are found in up to 90% of patients with non-Hodgkin's lymphoma (NHL) and have been shown to play an important role in lymphomagenesis by activating proto-oncogenes (1). Some of these translocations, which are associated with specific histologic subsets of NHL, have been characterized at the molecular level. In the t(8;14), t(8;22), and t(2;8) translocations associated with Burkitt Lymphoma, $L_3$-type acute lymphoblastic leukemia and AIDS-associated non-Hodgkin lymphoma (NHL), a known proto-oncogene, c-myc, was found juxtaposed to the immunoglobulin (Ig) loci (2,3). In the t(14;18) translocation, which is implicated in follicular-type NHL, molecular analysis of the sequences linked to the Ig locus led to the identification of a novel proto-oncogene, bcl-2 (4–6). The t(11;14) (q13;q32), mainly associated with "mantle zone" lymphoma, appears to involve the juxtaposition of the Ig heavy-chain locus with the bcl-1 locus, the site of the candidate proto-oncogene PRAD-1/cyclin D1 (7,8). These well characterized chromosome translocations are associated, however, with only a fraction of NHL cases, while a number of other recurrent translocations remain to be characterized for their genetic components.

One important example of such cytogenetic abnormalities is represented by various alterations affecting band 3q27. This region is involved in translocations with various chromosomal sites including, but not limited, to those carrying the Ig heavy- (14q32) or light- (2p12, 22q11) chain loci (9,10). Overall, 3q27 breakpoints are detectable in 7–12% of B-cell NHL cases by cytogenetic analysis, with t(3;22) (q27;q11) being the most frequent type detectable in 4–5% of NHL (9). The clinicopathologic relevance of 3q27 breakpoints is underscored by its consistent association with diffuse-type NHL, a frequent and clinical aggressive subtype for which no specific molecular lesion has yet been identified (9).

The recurrence of 3q27 breakpoints in NHL has prompted a search for the corresponding proto-oncogene. This invention discloses the cloning of clustered 3q27 breakpoints from two NHL cases carrying t(3;14) (q27;q32) translocations and the identification of genomic rearrangements within the same breakpoint region in additional NHL cases carrying translocations involving 3q27. Within the same region, a transcriptional unit has been identified, which represents the candidate proto-oncogene (bcl-6) associated with 3q27 translocations in B-NHL.

SUMMARY OF THE INVENTION

This invention provides an isolated vertebrate nucleic acid molecule of bcl-6 locus. This invention provides an isolated vertebrate DNA molecule of bcl-6 locus. This invention provides an isolated vertebrate cDNA molecule of bcl-6. This invention provides an isolated genomic DNA molecule of bcl-6. This invention provides an isolated vertebrate RNA molecule of bcl-6. This invention provides an isolated human nucleic acid molecule of bcl-6 locus.

In addition, this invention provides a nucleic acid molecule comprising a nucleic acid molecule of at least 15 nucleotides capable of specifically hybridizing with a sequence included within the sequence of the nucleic acid molecule of bcl-6.

In addition, this invention provides an isolated vertebrate DNA molecule of bcl-6 operatively linked to a promoter of RNA transcription. This invention provides a vector which comprises the isolated vertebrate DNA molecule of bcl-6.

In addition, this invention provides the above vector, wherein the isolated nucleic acid molecule is linked to a plasmid.

In addition, this invention provides a host vector system for the production of a polypeptide encoded by bcl-6 locus, which comprises the above vector in a suitable host.

In addition, this invention provides a method of producing a polypeptide encoded by bcl-6 locus, which comprises growing the above host vector system under suitable conditions permitting production of the polypeptide and recovering the polypeptide so produced.

In addition, this invention provides a polypeptide encoded by the isolated vertebrate nucleic acid molecule of bcl-6 locus. Further, this invention provides an antibody capable of binding to polypeptide encoded by bcl-6 locus.

In addition, this invention provides an antagonist capable of blocking the expression of the polypeptide encoded by bcl-6.

In addition, this invention provides an antisense molecule capable of hybridizing to the nucleic acid molecule of bcl-6.

In addition, this invention provides an assay for non-Hodgkin's lymphoma, a method for screening putative therapeutic agents for treatment of non-Hodgkin's lymphoma and a method for diagnosing B-cell lymphoma.

Finally, this invention provides a method of treating a subject with non-Hodgkin's lymphoma.

BRIEF DESCRIPTION OF THE FIGURES

FIGS. 4A–4C: Southern blot hybridization analysis of bcl-6 rearrangements in NHL carrying 3q27 breakpoints. The probes used are illustrated in FIG. 2. U937 and SK-N-MC DNAs are used as germ-line controls since their hybridization pattern was identical to the one observed in a panel of 19 control DNAs tested. The detected cytogenetic abnormalities affecting 3q27 in each case are: KC1445: t(3;14) (q27;q32); SM1444: t(3;14) (q27;q32); TF1403: t(3;14) (q27;q32); LD1411: t(3,14) (q27;q32); EM352: t(3;22) (q27;q11); CF755: t(3;12) (q27;q11); S0955: der(3)t(3;5) (q27;q31).

FIG. 5: Identification of the bcl-6 transcriptional unit. 15 $\mu$g of total RNA isolated from the indicated human cell lines was analyzed by Northern blot hybridization using the Sac 4.0 probe (see FIG. 2). CB33:EBV-immortalized human B lymphoblastoid cell line; HeLa: human cervical carcinoma cell line; Daudi: human Burkitt lymphoma cell line; Hut78: human T-cell leukemia cell line. Hybridization of the same filter to a mouse GAPDH probe is shown as control for RNA amount loaded in each lane. The faint band comigrating with 28S RNA in all the lanes may be the result of cross-hybridization with ribosomal RNA sequences.

FIGS. 9A–9D: cDNA and Amino Acid Sequences of BCL-6 (SEQ ID NOs. 1 and 2). The Sac 4.0 probe was used to screen a recombinant phage cDNA library constructed from Bjab B cell lymphoma line RNA. A 4.0 kilobase cDNA was isolated and its nucleotide sequence was determined. It contains a long open reading frame potentially coding for 706 amino acid protein which contains five zinc-finger domains (underlined in the figure; C and H residues which identify the C2H2-type zinc-finger structure are indicated in bold).

FIGS. 10A–10B: Structure of BCL-6 cDNA and sequence of its predicted protein product. FIG. 10A: Schematic representation of the full-length BCL-6 cDNA clone showing the relative position of the open reading frame (box) with 5' and 3' untranslated sequences (lines flanking the box). The approximate positions of the zinc-finger motifs (Zn++) and the NH$_2$-terminal homology (shaded area) with other proteins are also indicated. FIG. 10B SEQ ID NO: 2: The predicted amino acid sequence of the BCL-6 protein. The residues corresponding to the six zinc-finger motifs (H-C links). The GenBank Accession number for BCL-6 cDNA and amino acid sequences is U00115.

FIG. 11: Homology of the NH$_2$-terminal region of BCL-6 to other Krüppel zinc-finger proteins, viral (VA55R), or cellular non-zinc-finger (kelch) proteins SEQ ID NO: 3–9. Black background indicates identical residues found four or more times at a given position; grey indicates conserved residues that appear in at least four sequences at a given position. Conserved amino acid substitutions are defined according to scheme (P, A, G, S, T), (Q, N, E, D), (H, K, R), (L, I, V, M), and (F< Y< W) Numbering is with respect to the methionine initiation codon of each gene.

FIGS. 13A–13B: Rearrangements of the BCL-6 gene in diffuse large-cell lymphomas (DLCL). Genomic DNA extracted from tumor biopsies of DLCL cases and from normal lymphocytes (lane N) was digested with the indicated restriction enzymes and analyzed by Southern blot hybridization using the Sac 4.0 probe. Abnormal restriction fragments are indicated by the arrows.

FIG. 16A: Analysis of EBV termini heterogeneity in AIDS-NHL. DNAs were digested with BamHI and subjected to Southern hybridization using a DNA probe specific for the fused termini of the EBV genome. U937, a monocytic leukemia cell line, is used as a negative control. A lymphoblastoid cell line derived by EBV infection of normal polyclonal B cells (NC2) is used as control for polymorphic EBV termini. Representative samples of AIDS-NHL, both positive (DK3794, DK4338, DK2814, DK3973) and negative (DK3479), are shown. FIG. 16B: Southern blot analysis of c-MYC rearrangements in AIDS-NHL. Genomic DNAs from the cases shown was digested with HindIII and probed with clone MC413RC[41], representative of c-MYC exon 3. A lymphoblastoid cell line (NC2) was used as control for c-MYC germline configuration. Among the cases shown, two cases of AIDS-DLCL (DK3537 and DK1446) display a c-MYC rearrangement. FIG. 16C: Analysis by PCR-SSCP of the p53 gene in AIDS-NHL. Representative examples are shown for p53 exon 5. Samples were scored as abnormal when differing from the normal control (N). A sample known to harbor a p53 mutation was used as positive control (POS). Among the cases shown, DK1171, a case of AIDS-SNCCL, shows a p53 mutation which was further characterized by direct sequencing of the PCR product.

FIG. 18A: Freedom from progression in BCL-6 rearranged cases (open circles, top curve) compared to BCL-6 germline cases (closed circles, bottom curve) (P=0.007). FIG. 18B: Overall survival from time of diagnosis for BCL-6 rearranged CLLC (open circle, top curve), compared to BCL-6 germline, BCL-2 germline DLLC (dark triangles, middle curve), and BCL-2 rearranged DLLC (dark boxes, bottom curve) (P=0.02).

DETAILED DESCRIPTION OF THE INVENTION

Figure 1:
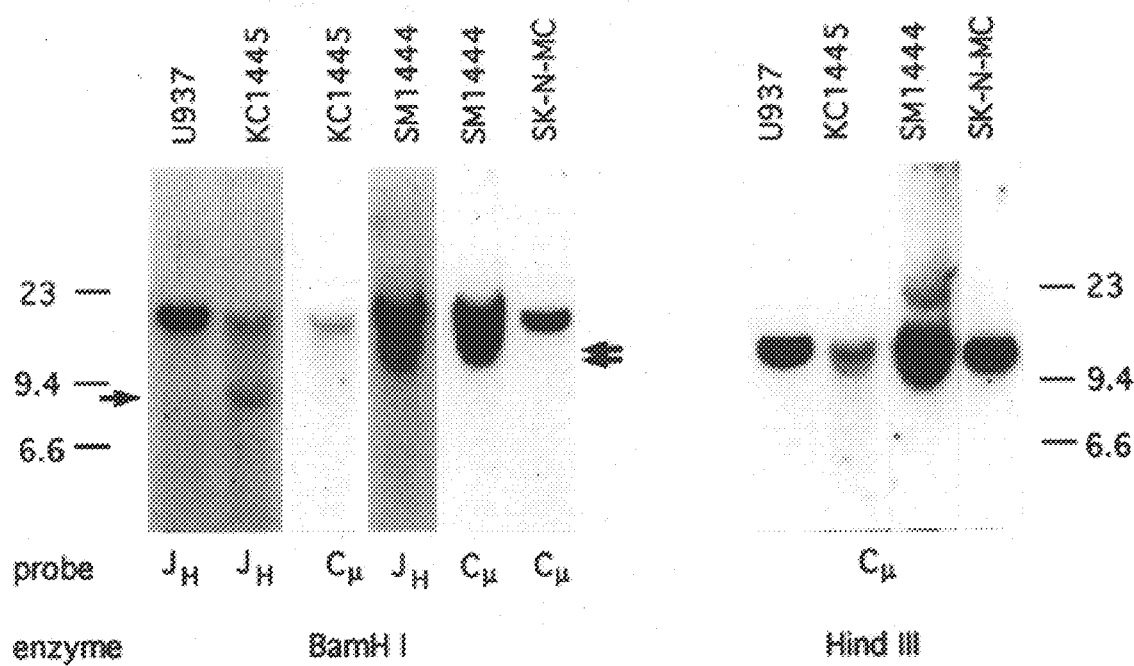
FIG. 1: Immunoglobulin gene rearrangement analysis of KC1445 and SM1444 DNA. DNA extracted from the cell lines U937 (monocytic leukemia) and SK-N-MC (neuroblastoma) were used as controls for non-rearranged, germ-line Ig genes. In the left panel, the arrow on the left points to the rearranged $J_H$ fragment which does not contain $C_\mu$ sequences in KC1445 DNA, while the two arrows on the right point to the two distinct fragments containing $J_H$ or $C_\mu$ sequences in SM1444 DNA.

The following standard abbreviations are used throughout the specification to indicate specific nucleotides:

| C = cytosine | A = adenosine |
|---|---|
| T = thymidine | G = guanosine |

This invention provides an isolated vertebrate nucleic acid molecule of the bcl-6 locus. As used herein, bcl-6 locus means the breakpoint cluster region in B-cell lymphomas. The bcl-6 locus is of 30 kilobase in length containing at least a bcl-6 gene which codes for a protein. Therefore, the bcl-6 locus contains both the 5' and 3' flanking region of the coding sequences of the bcl-6 gene.

In an embodiment, the isolated, vertebrate nucleic acid molecule of bcl-6 locus is DNA. In another embodiment, the isolated, vertebrate nucleic acid of the bcl-6 locus is cDNA. In a further embodiment, the isolated, vertebrate nucleic acid is genomic DNA. In a still further embodiment, the isolated, vertebrate nucleic acid molecule is RNA.

This invention provides an isolated, human nucleic acid molecule comprising the bcl-6 locus.

The DNA molecules described and claimed herein are useful for the information which they provide concerning the amino acid sequence of the polypeptide and as products for the large scale synthesis of the polypeptide by a variety of recombinant techniques. The molecule is useful for generating new cloning and expression vectors, transformed and transfected prokaryotic and eukaryotic host cells, and new and useful methods for cultured growth of such host cells capable of expression of the polypeptide and related products.

Moreover, the isolated vertebrate nucleic acid molecules are useful for the development of probes to study B cell lymphomas.

This invention provides a nucleic acid molecule comprising a nucleic acid molecule of at least 15 nucleotides capable of specifically hybridizing with a sequence included within the sequence of the bcl-6 locus. In an embodiment, this molecule is DNA. In another embodiment, the molecule is RNA.

As used herein, the phrase "specifically hybridizing" means the ability of a nucleic acid molecule to recognize a nucleic acid sequence complementary to its own and to form double-helical segments through hydrogen bonding between complementary base pairs.

The above nucleic acid molecule of at least 15 nucleotides capable of specifically hybridizing with a sequence of bcl-6 locus may be used as a probe for bcl-6 sequences. Nucleic acid probe technology is well known to those skilled in the art who will readily appreciate that such probes may vary greatly in length and may be labeled with a detectable label, such as a radioisotope or fluorescent dye, to facilitate detection of the probe. DNA probe molecules may be produced by insertion of a DNA molecule having the full-length or a fragment of the bcl-6 locus into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the full length or a fragment of the bcl-6 locus downstream of a bacteriophage promoter such as T3, T7 or SP6. Large amounts of RNA probe may be produced by incubating the labeled nucleotides with a linearized bcl-6 or its fragment where it contains an upstream promoter in the presence of the appropriate RNA polymerase.

This invention provides an cDNA molecule of bcl-6 locus operatively linked to a promoter of RNA transcription.

This invention provides a vector which comprises the nucleic acid molecule of bcl-6 locus. This invention provides the above vector, wherein the isolated nucleic acid molecule is linked to a plasmid.

This invention further provides isolated cDNA molecule of the bcl-6 locus operatively linked to a promoter of RNA transcription. Various vectors including plasmid vectors, cosmid vectors, bacteriophage vectors and other viruses are well known to ordinary skilled practitioners.

As an example to obtain these vectors, insert and vector DNA can both be exposed to a restriction enzyme to create complementary ends on both molecules which base pair with each other and are then ligated together with DNA ligase. Alternatively, linkers can be ligated to the insert DNA which correspond to a restriction site in the vector DNA, which is then digested with the restriction enzyme which cuts at that site. Other means are also available and known to an ordinary skilled practitioner.

Figure 8:
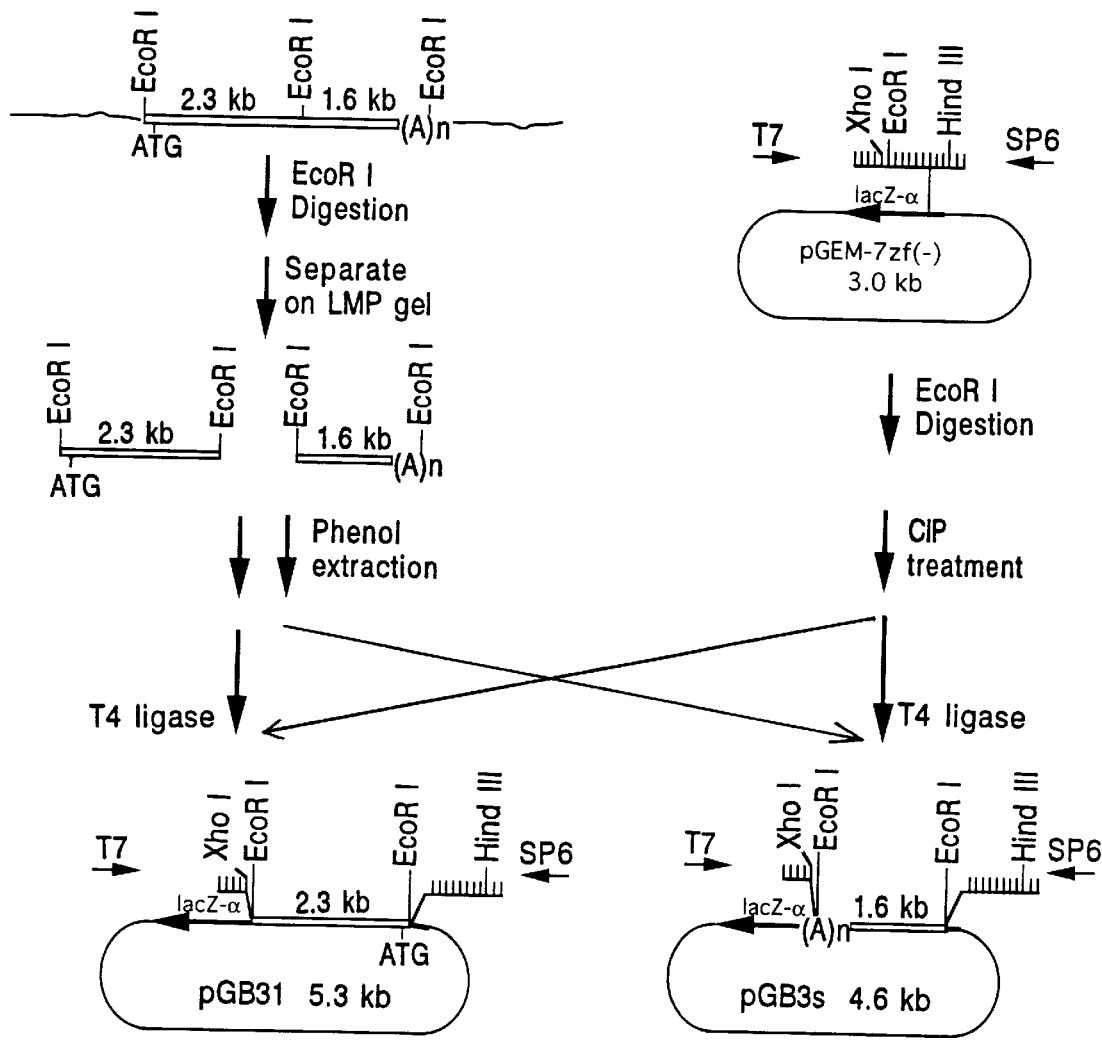
FIG. 8: pGB31 and pGB3s plasmid construction.

In an embodiment, a partial CDNA molecule of the bcl-6 locus is linked to pGEM-7zf(−) and the resulting plasmid is designated as pGB31 (FIG. 8). Plasmid, pGB31 was deposited on Jun. 3, 1993 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid, pGB31 was accorded with ATCC Accession Number 75476.

In an another embodiment, a partial cDNA molecule of the bcl-6 locus is linked to pGEM-7zf(−) and the resulting plasmid is designated as pGB3s (FIG. 8). Plasmid, pGB3s was deposited on Jun. 3, 1993 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid, pGB3s was accorded with ATCC Accession Number 75477.

This invention provides a host vector system for the production of a polypeptide encoded by bcl-6 locus, which comprises the above vector in a suitable host.

This invention provides the above host vector system, wherein the suitable host is a bacterial cell, insect cell, or animal cell.

Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well-known in the art, for example the methods described above for constructing vectors in general. Expression vectors are useful to produce cells that express the polypeptide encoded by the bcl-6 locus.

This invention further provides an isolated DNA or cDNA molecule described hereinabove wherein the host cell is selected from the group consisting of bacterial cells (such as E. coli), yeast cells, fungal cells, insect cells and animal cells. Suitable animal cells include, but are not limited to Vero cells, HeLa cells, Cos cells, CV1 cells and various primary mammalian cells.

This invention provides a method of producing a polypeptide encoded by bcl-6 locus, which comprises growing the above host vector system under suitable conditions permitting production of the polypeptide and recovering the polypeptide so produced.

This invention provides a polypeptide encoded by the isolated vertebrate nucleic acid molecule of bcl-6 locus.

This invention provides an antibody capable of binding to polypeptide encoded by bcl-6 locus. In an embodiment, the antibody is monoclonal.

This invention provides a method to select specific regions on the polypeptide encoded by the bcl-6 locus to generate antibodies. The protein sequence may be determined from the cDNA sequence. Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer of the cell membrane, while hydrophilic regions are located on the cell surface, in an aqueous environment. Usually, the hydrophilic regions will be more immunogenic than the hydrophobic regions. Therefore the hydrophilic amino acid sequences may be selected and used to generate antibodies specific to polypeptide encoded by the bcl-6 locus. The selected peptides may be prepared using commercially available machines. As an alternative, DNA, such as a cDNA or a fragment thereof, may be cloned and expressed and the resulting polypeptide recovered and used as an immunogen.

Polyclonal antibodies against these peptides may be produced by immunizing animals using the selected peptides. Monoclonal antibodies are prepared using hybridoma technology by fusing antibody producing B cells from immunized animals with myeloma cells and selecting the resulting hybridoma cell line producing the desired antibody. Alternatively, monoclonal antibodies may be produced by in vitro techniques known to a person of ordinary skill in the art. These antibodies are useful to detect the expression of polypeptide encoded by the bcl-6 locus in living animals, in humans, or in biological tissues or fluids isolated from animals or humans.

The antibody may be labelled with a detectable marker, including but not limited to: a radioactive label, or a calorimetric, luminescent, or fluorescent marker, or gold. Radioactive labels include but are not limited to: $^3$H, $^{14}$C, $^{32}$P, $^{33}$P, $^{35}$S, $^{36}$Cl, $^{51}$Cr, $^{57}$Co, $^{59}$Co, $^{59}$Fe, $^{90}$Y, $^{125}$I, $^{131}$I, and $^{186}$Re. Fluorescent markers include but are not limited to: fluorescein, rhodamine and auramine. Methods of producing the polyclonal or monoclonal antibody are known to one of ordinary skill in the art.

Further, the antibody complex may be detected by a second antibody which may be linked to an enzyme, such as alkaline phosphatase or horseradish peroxidase. Other enzymes which may be employed are well known to one of ordinary skill in the art.

This invention provides for the isolated nucleic acid molecule of bcl-6 that is labelled with a detectable marker. The detectable marker may be a radioactive label, a calorimetric, luminescent, or a fluorescent marker. Other detectable markers are known to those skilled in the art as hereinabove described.

This invention provides an antagonist capable of blocking the expression of the polypeptide encoded by the isolated nucleic acid molecule of bcl-6. The antagonist may be a triplex oligonucleotide capable of hybridizing to nucleic acid molecule bcl-6.

This invention provides an antisense molecule capable of hybridizing to the nucleic acid molecule bcl-6. The antisense molecule may be DNA or RNA.

This invention provides a triplex oligonucleotide capable of hybridizing with a double stranded DNA molecule bcl-6.

The antisense molecule may be DNA or RNA or variants thereof (i.e. DNA with a protein backbone). The present invention extends to the preparation of antisense nucleotides and ribozymes that may be used to interfere with the expression of the receptor recognition proteins at the translation of a specific mRNA, either by masking that mRNA with an antisense nucleic acid or cleaving it with a ribozyme.

Antisense nucleic acids are DNA or RNA molecules that are complementary to at least a portion of a specific mRNA molecule. In the cell, they hybridize to that mRNA, forming a double stranded molecule. The cell does not translate an MRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules upon introduction to cells.

This invention provides a transgenic nonhuman mammal which comprises the isolated nucleic acid molecule bcl-6 introduced into the mammal at an embryonic stage.

This invention provides an assay for non-Hodgkin's lymphoma, comprising (a) incubating a sample of suitable body fluid for a subject with a monoclonal antibody reactive with non-Hodgkin's lymphoma cells to a solid support, (b) removing unbound body fluid from the support, and (c) determining the level of antigen activity exhibited by the bound body fluid to the support.

The suitable bodily fluid sample is any bodily fluid sample which would contain non-hodgkin lymphoma cells or fragments thereof. A suitable bodily fluid includes, but is not limited to, serum, plasma, cerebrospinal fluid, and urine. In the preferred embodiment, the suitable bodily fluid sample is serum or plasma. In addition, the body fluid sample may cells from bone marrow, or a supernate from a cell culture. Methods of obtaining a suitable bodily fluid sample from a subject are known to those skilled in the art.

This invention provides a method for screening putative therapeutic agents for treatment of non-Hodgkin's lymphoma, which comprises determining in a first sample from a subject with non-Hodgkin's lymphoma the presence of the isolated nucleic acid molecule bcl-6, administering to the subject a therapeutic amount of the agent such that the agent is contacted with the cell associated with the condition, determining after a suitable period the amount of the isolated nucleic acid molecule in a sample from the treated subject, and comparing the amount of isolated nucleic acid molecule determined in the first sample with the amount determined in the sample from the treated subject, a difference indicating the effectiveness of the agent, thereby screening putative therapeutic agents for treatment of non-Hodgkin's lymphoma.

Further, this invention provides an assay system that is employed to identify drugs or other molecules capable of binding to the nucleic acid molecule bcl-6 or proteins, either in the cytoplasm or in the nucleus, thereby inhibiting or potentiating transcriptional activity. Such assay would be useful in the development of drugs that would be specific against particular cellular activity, or that would potentiate such activity, in time or in level of activity.

The above described probes are also useful for in-situ hybridization or in order to locate tissues which express this gene, or for other hybridization assays for the presence of this gene or its mRNA in various biological tissues.

The in-situ hybridization technique using the labelled nucleic acid molecule bcl-6 is well known in the art. Essentially, tissue sections are incubated with the labelled nucleic acid molecule to allow the hybridization to occur. The molecule will carry a marker for the detection because it is "labelled", the amount of the hybrid will be determined based on the detection of the amount of the marker. Further, immunohistochemical protocols may be employed which are known to those skilled in the art.

This invention provides a method of diagnosing diffuse-type B-cell lymphoma in a subject which comprises detecting in a sample from the subject nucleic acid molecule of bcl-6 locus.

This invention provides a method for diagnosing B-cell lymphoma in a subject comprising: (a) obtaining DNA sample from the subject; (b) cleave the DNA sample into fragments; (c) separating the DNA fragments by size fractionation; (d) hybridizing the DNA fragments with a nucleic acid molecule comprising a nucleic acid molecule of at least 15 nucleotides capable of specifically hybridizing with a sequence included within the sequence of the nucleic acid molecule of the bcl-6 locus to detect the DNA fragment containing the bcl-6 sequence; and (e) comparing the detected DNA fragment from step (d) with the DNA fragment from a known normal subject, the difference in size of the fragments indicating the occurrence of B-cell lymphoma in the subject. In a preferred embodiment, the above diagnostic method is for diffuse-type B-cell lymphomas.

A person of ordinary skill in the art will be able to obtain appropriate DNA sample for diagnosing B-cell lymphoma in a subject. The DNA sample obtained by the above described method may be cleaved by restriction enzyme. The uses of restriction enzymes to cleave DNA and the conditions to perform such cleavage are well-known in the art.

In an embodiment, the size fractionation in step (c) of the above-described method is effected by a polyacrylamide gel. In another embodiment, the size fractionation is effected by an agarose gel.

This invention also provides the above-described diagnosis method wherein step the nucleic acid molecule in step (d) is labeled with a detectable marker. The detectable marker includes but is not limited to a radiolabelled molecule, a fluorescent molecule, an enzyme, or a ligand.

In a preferred embodiment, the above-described diagnosis method further comprises transferring the DNA fragments into a solid matrix before the hybridization step (d). One example of such solid matrix is nitrocellulose paper.

Figure 6:
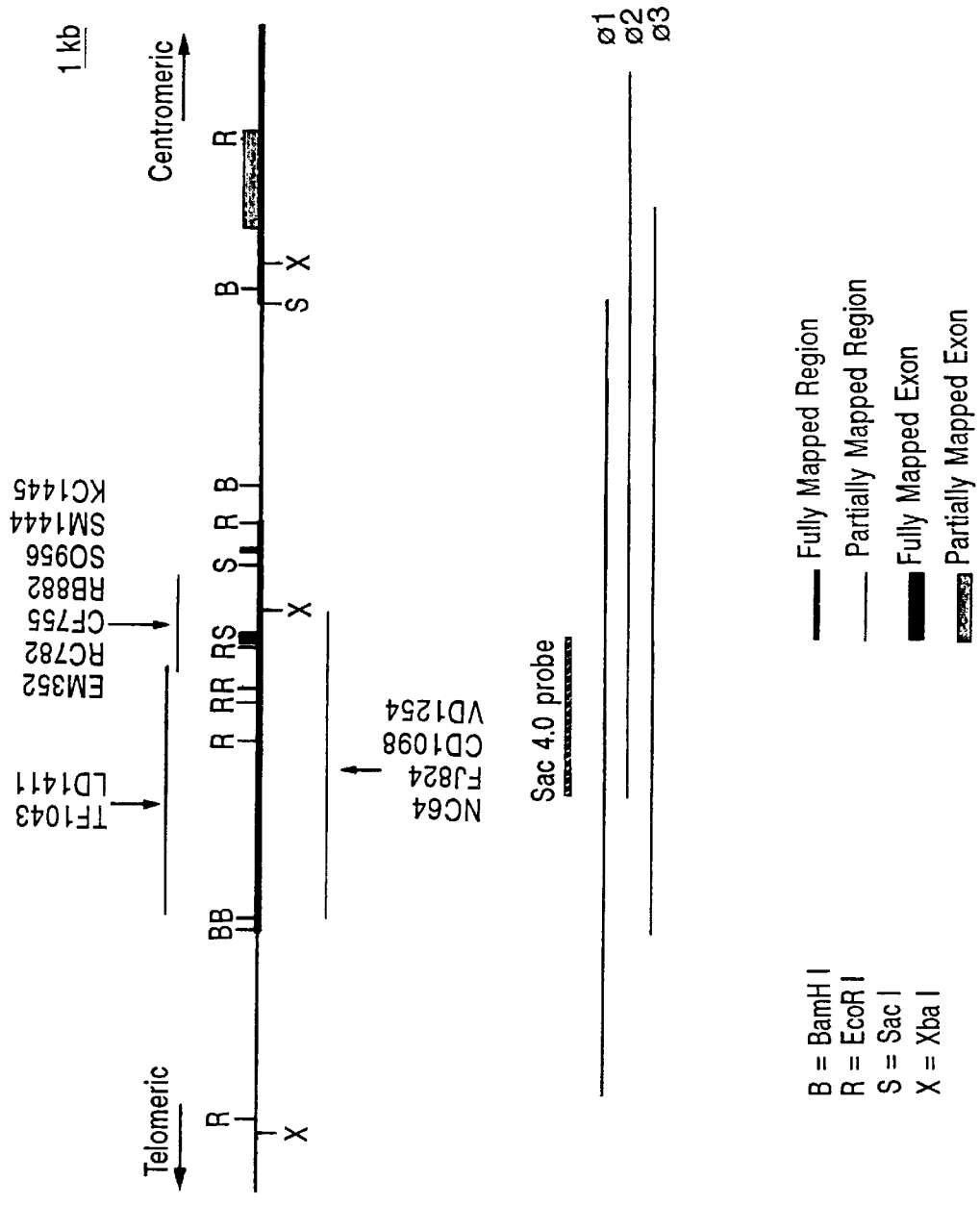
FIG. 6: Map of normal human BCL-6 locus. A recombinant genomic DNA library derived from normal placenta DNA was obtained from STRATAGENE Inc and screened by plaque hybridization using the Sac 4.0 probe. Three recombinant phages were obtained ($\phi$1–3 in the figure) whose inserts have been mapped and shown to overlap on approximately 30 kilobases of genomic DNA representing the BCL-6 locus. These sequences containing bcl-6 exons since they hybridize to the cDNA probe. The precise position of the exons has only been approximately determined and is schematically indicated in the figure. The position of the breakpoints observed in various lymphoma cases is also indicated.
Figure 7:
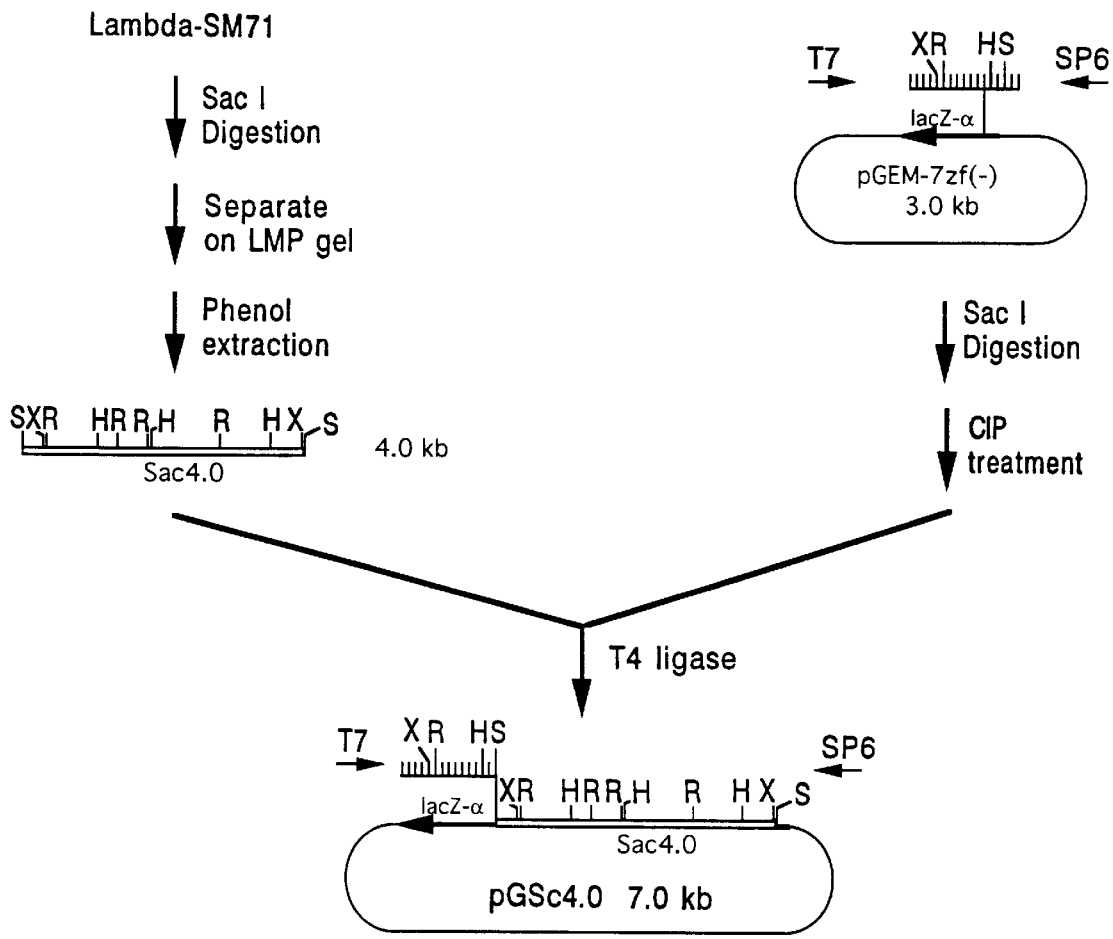
FIG. 7: psac 40 plasmid construction.

As an example for the above-described diagnosis method is shown in FIGS. 4A–4C where different NHL sample are analyzed. More lymphoma cases and their breakpoints are shown in FIG. 6.

This invention also provides a method for diagnosing B-cell lymphoma in a subject comprising: (a) obtaining RNA sample from the subject; (b) separating the RNA sample into different species by size fractionation; (c) hybridizing the RNA species with a nucleic acid molecule comprising a nucleic acid molecule of at least 15 nucleotides capable of specifically hybridizing with a sequence included within the sequence of the nucleic acid molecule of the bcl-6 locus to detect the RNA species containing the bcl-6 sequence; and (d) comparing the RNA species obtained from (c) with the RNA species from a known normal subject, the difference in size of the species indicating the occurrence of B-cell lymphoma in the subject.

In an embodiment, the size fractionation in step (b) is effected by a polyacrylamide or agarose gel.

This invention also provides the above-described method where in step (c), the nucleic acid molecule is labeled with a detectable marker. The detectable marker includes but is not limited to a radiolabelled molecule, a fluorescent molecule, an enzyme, or a ligand.

This invention also provides the above-method further comprises transferring the RNA species into a solid matrix before step (c).

This invention also provides various uses of bcl-6 locus/gene an its derivatives. This invention further provides a method for diagnosis of B cell lymphoma and/or diffuse-type B cell lymphoma using bcl-6 DNA probes or synthetic oligonucleotide primers derived from bcl-6 sequences to detect bcl-6 rearrangements/mutations by Southern blotting PCR or other DNA based techniques.

This invention also provides a method of diagnosis of B cell lymphoma and/or diffuse-type B cell lymphoma using bcl-6 DNA probes or synthetic oligonucleotide primers derived from bcl-6 sequences to detect abnormal bcl-6 RNA species by Northern blotting, PCR or other RNA-based techniques.

This invention further provides a method of diagnosis of B cell lymphoma and/or diffuse-type B cell lymphoma using antiserum or monoclonal antibodies directed against the bcl-6 protein product(s).

This invention provides a method of treating a subject with non-Hodgkin's lymphoma comprising administering an effective amount of the antisense molecule of the nucleic acid molecule bcl-6 operatively linked to a suitable regulatory element coupled with a therapeutic DNA into a tumor cell of a subject, thereby treating the subject with non-Hodgkin's lymphoma.

This invention provides a method of treating a subject with non-Hodgkin's lymphoma, comprising administering an effective amount of the antagonist capable of blocking the expression of the polypeptide encoded by the isolated nucleic acid molecule of bcl-6, and a suitable acceptable carrier, thereby treating the subject with non-Hodgkin's lymphoma.

Further, as is known to those of ordinary skill in the art effective amounts vary with the type of therapeutic agent. It is known to those of ordinary skill in the art how to determine an effective amount of a suitable therapeutic agent.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The-preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The subjects contained herein may be a mammal, or more specifically a human, horse, pig, rabbit, dog, monkey, or rodent. In the preferred embodiment the subject is a human.

The compositions are administered in a manner compatible with the dosage formulation, and in a therapeutically effective amount. Precise amounts of active ingredient required to be administered depend on the judgment of the practitioner and are peculiar to each individual.

Suitable regimes for initial administration and booster shots are also variable, but are typified by an initial administration followed by repeated doses at one or more hour intervals by a subsequent injection or other administration.

As used herein administration means a method of administering to a subject. Such methods are well known to those skilled in the art and include, but are not limited to, administration topically, parenterally, orally, intravenously, intramuscularly, subcutaneously or by aerosol. Administration of the agent may be effected continuously or intermittently such that the therapeutic agent in the patient is effective to treat a subject with non-hodgkin's lymphoma.

Finally, this invention provides a therapy of B cell lymphoma and/or diffuse-type B cell lymphoma using anti bcl-6 reagents including specific antisense sequences and compounds interfering with bcl-6 functions.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAIL SECTION I

Materials and Methods

DNA Extraction and Southern Blot Analysis. Total genomic DNA was purified from frozen tumor biopsies by cell lysis, proteinase K digestion, "salting-out" purification and ethanol precipitation as previously described (11). Southern blot hybridization analysis was performed in 50% formamide, 3× SSC, 10× dextran sulphate, 5× Denhardt's solution, 0.5% SDS at 37° C. for 16 hrs. Filters were washed in 0.2× SSC, 0.5% SDS at 60° C. for 2 hrs. DNA probes were $^{32}$P-labelled by the random priming method (12).

DNA Probes. The following probes were used for Southern blot analysis of Ig gene rearrangements: i) ($J_H$) probe: 6.6 kb BamHi/HindIII fragment from the human Ig heavy-chain ($Ig_H$) locus (13); ii) ($C_\mu$) probe: 1.3 kb EcoRI fragment containing the first two exons of human $C_\mu$(13).

Genomic Cloning. Genomic libraries from NHL cases SM1444 and KC1445 were constructed by partial Sau 3A restriction digestion of genomic DNA and ligation of gel-purified 15–20 kb fractions into LambdaGem-11 phage vector (Promega). Library screening was performed by plaque-hybridization using the $C_\mu$ probe.

Fluorescence in situ Hybridization Analysis (FISH). Phage DNA was labelled with biotin-14-dATP by nick translation and hybridized to metaphase spreads from normal human lymphocytes as described (14). To visualize the hybridization signal and the corresponding bands sequentially under the microscope, the slides were stained and counterstained with propidium iodide and 4'6'-diamideno-2-phenylindole (DAPI), respectively.

Northern Blot Hybridization Analysis. RNAs from several human cell lines were extracted by the guanidine-isothiocyanate method (15). For Northern blot analysis, RNA samples were electrophoresed through 0.9% agarose-2.2M formaldehyde gels and then transferred to nitrocellulose filters. Hybridization and washing were performed as described for Southern blot analysis.

Experimental Results

DNA was extracted from tumor tissue of two cases (SM1444 and KC1445) of IgM-producing, diffuse-type B-cell NHL carrying the t(3;14)(q27;q32) translocation. Since the involvement of the $Ig_H$ locus was suspected based on the 14q32 breakpoint, SM1444 and KC1445 DNAs were first analyzed by Southern blot hybridization using combinations of enzymes and probes specific for the $J_H$ and $C_\mu$ regions of the $Ig_H$ locus (13). In both cases, digestion by BamHI showed rearranged fragments containing $J_H$ sequences (FIG. 1). Subsequent hybridizations to the $C_\mu$ probe showed, in each case, that one rearranged fragment containing $J_H$ sequences was not linked to $C_\mu$ sequences (see failure of the $C_\mu$ probe to hybridize to the same rearranged BamHI fragment detected by $J_H$ (FIG. 1) as would be expected for the physiologically rearranged $Ig_H$ allele in IgM producing cells. In addition, in both cases, digestion with HindIII and hybridization with $C_\mu$ detected a rearranged fragment, a finding inconsistent with either germ-line or physiologically rearranged $Ig_H$ genes, since both HindIII sites flanking $C_\mu$ sequences are not involved in V-D-J arrangements (13). The observed pattern is, however, consistent with chromosomal breakpoints located within $C_\mu$ switch sequences, as previously observed in several cases of chromosomal translocations involving the $Ig_H$ locus (2,16–18).

Figure 2:
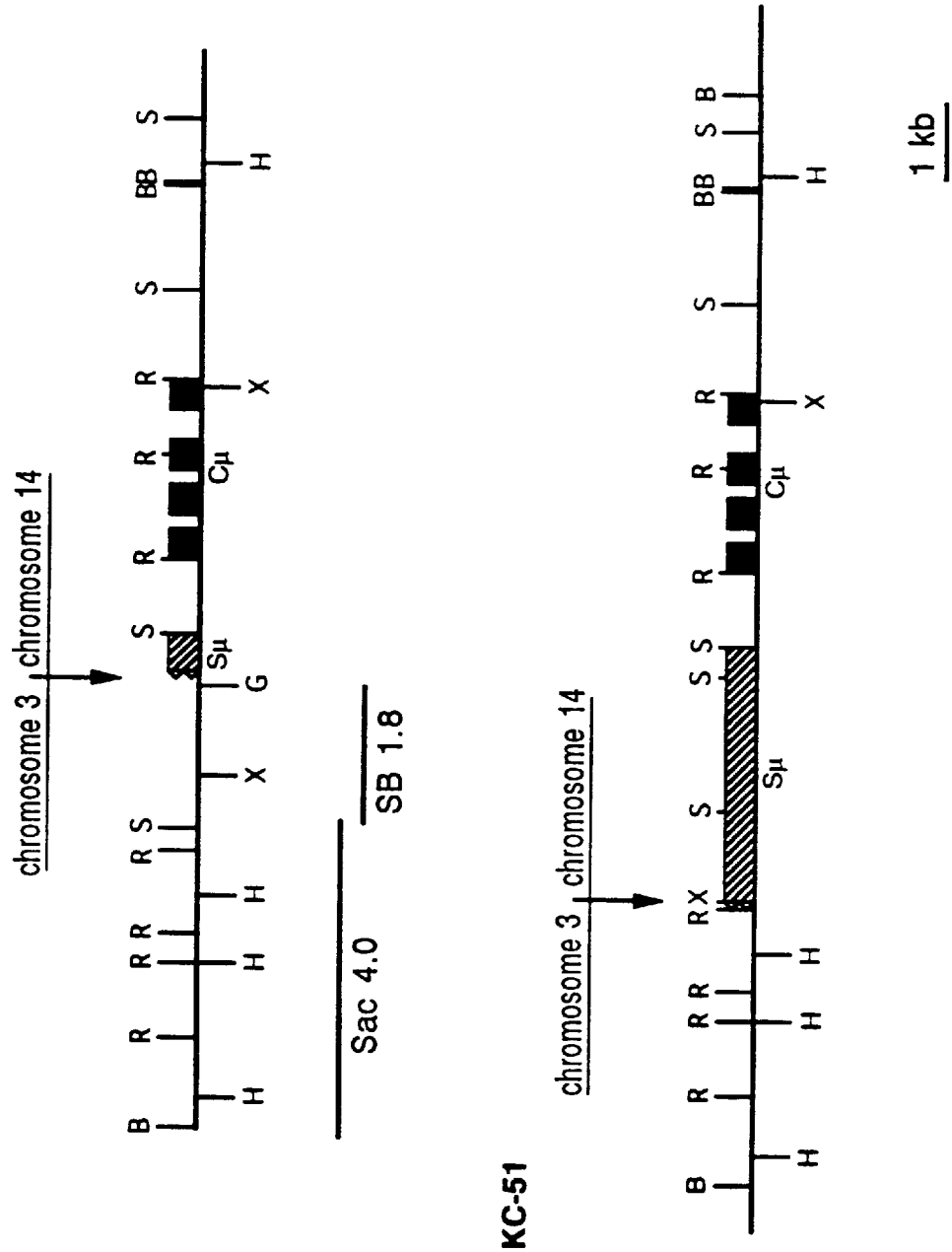
FIG. 2: Molecular cloning of the chromosomal breakpoints from two NHL cases with t(3;14). Illustrated are the maps of two representative phage clones spanning the breakpoint regions in case SM1444 (SM-71) and KC1445 (KC-51). Chromosome 14 portions of the phage inserts are indicated by a solid line with hatched and black boxes representing switch sequences and $C_\mu$ exons, respectively. Vertical arrows point to the junctions of chromosome 3 and 14 sequences. The probes used for Southern (FIG. 4) and Northern (FIG. 5) analysis are illustrated below the SM-71 map. Restriction enzyme sites are indicated as: B=BamHI; H=HindIII; R=EcoRI; G=BblII; S=sacI.

Based on this analysis, the $C_\mu$ containing fragments from each case were cloned by screening genomic libraries constructed from SM1444 and KC1445 DNAs using the $C_\mu$ probe. Restriction mapping and hybridization analysis of several phage clones led to the identification of recombinant phages from each library which contained $C_\mu$ sequences linked to sequences unrelated to the $Ig_H$ locus (see FIG. 2 for maps of representative phage clones). The Ig portions of the phage inserts overlapped along the $C_\mu$ region extending 5' into the switch region where alignment with the restriction map of the normal Ig heavy-chain locus was lost. The location of the breakpoint within $C_\mu$ switch sequences was confirmed for case SM1444 by DNA sequence analysis of the breakpoint junction of phage SM-71, which revealed the presence of the repeated motifs typical of the $Ig_H$ switch regions on the chromosome 14 side (19). The Ig-unrelated portions of phage SM-71 and KC-51 also overlapped with each other in their restriction maps, suggesting that they were derived from the same genomic region. This notion is further supported by the fact that probe Sac 4.0 derived from SM-71 was able to hybridize to the corresponding region of KC-51 in Southern blot analysis.

Figures 3A, 3B:
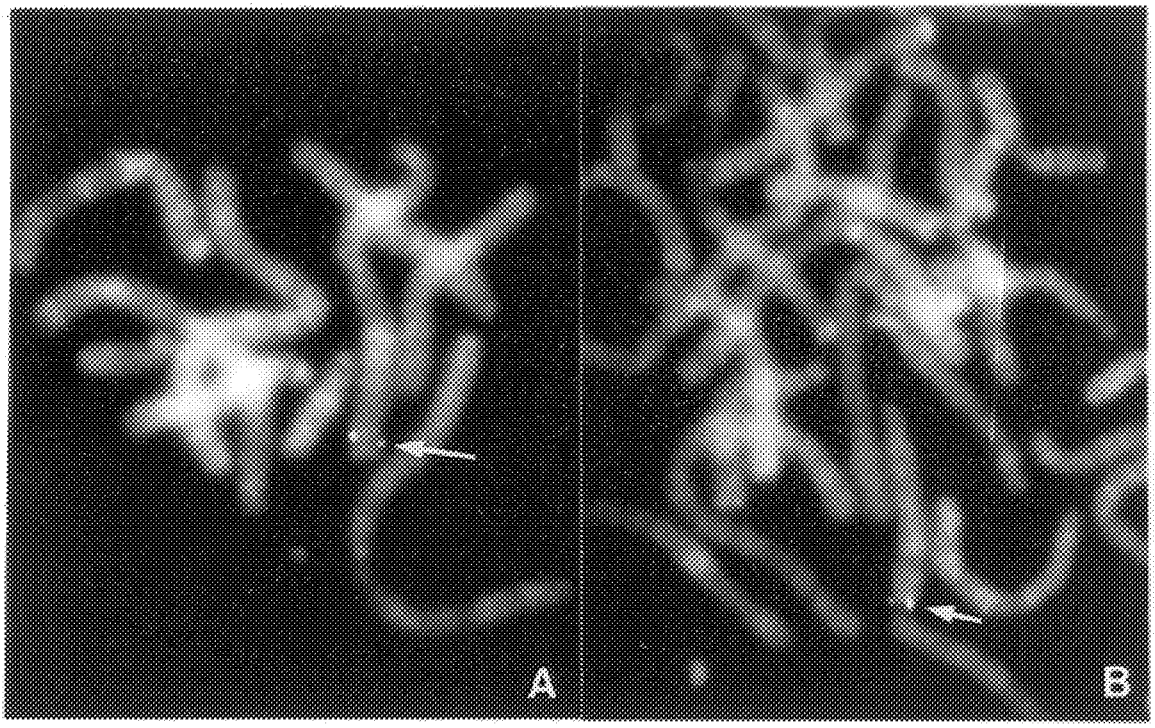
FIGS. 3A–3B: Localization of phage SM-71 sequences to chromosomes 3 and 14 by fluorescence in situ hybridization. Consistent hybridization signals at 3q27 (arrow in panel A) and 14q32 (arrow in panel B) demonstrated that the insert is derived from the translocation junction.

To determine the chromosomal origin of the Ig-unrelated sequences, a recombinant phage (SM-71) derived from case SM1444, was used as a probe in FISH analysis on metaphase chromosome spreads from mitogen-stimulated normal blood lymphocytes. The phage probe hybridized specifically to chromosome 14q32 as well as to chromosome 3q27 (FIGS. 3A–3B), indicating that the recombinant phage insert contained one of the two chromosomal junctions of the reciprocal t(3;14) translocation. Thus, taken together, the results of cloning and FISH analysis established that, in both NHL cases studied, the chromosomal translocation has linked sequences within the switch region of the $C_\mu$ locus to sequences from band 3q27, consistent with the cytogenetic description of the t(3;14) (q27;q32) translocation. In the two NHL cases studied, the breakpoints on 3q27 were located within 3 kb of the same genomic locus, which was termed bcl-6.

In order to determine whether 3q27 breakpoints in additional NHL cases were also located within the cloned portion of the bcl-6 locus, bcl-6 rearrangements were examined in a total of 19 NHL cases carrying 3q27 breakpoints, including 4 (two cloned cases and two additional ones) carrying t(3;14) (q27;q32) as well as 15 cases carrying 3q27 translocations involving regions other than 14q32. Southern blot hybridization using probes derived from phage SM-71 (see FIG. 2) detected rearranged fragments in EcoRI-and/or BglII-digested DNA in 7 of 19 cases studied, including all 4 t(3;14) cases as well as 3 cases with other types of translocations (see FIGS. 4A–4C for cytogenetic description of the cases and representative results). These results indicate that heterogeneous 3q27 breakpoints cluster in a fairly restricted region within bcl-6 independently of the partner chromosome involved in the translocation.

Whether the bcl-6 locus adjacent to the chromosomal breakpoints contained a transcriptional unit was investigated. Probe Sac 4.0 (see FIG. 2) was used to detect RNA expression in several human cell lines by Northern blot analysis. A major 2.4 kb RNA species was readily detectable in two B-cell derived cell lines tested, while a relatively less abundant 4.4 kb species is present in CB33 only. No hybridization was detected in a T-cell derived cell line (HUT 78) nor in HeLa cells (FIG. 5). This result indicates that 3q27 sequences immediately adjacent to the chromosomal breakpoint cluster are part of a gene (bcl-6) which is expressed in cells of the B lineage.

Experimental Discussion

This study reports the identification and cloning of a genomic region, bcl-6, involved in recurrent chromosomal translocations affecting band 3q27 in NHL. The region is defined by the clustered position of breakpoints in seven NHL cases carrying 3q27 translocations involving either IgH or several other loci. A more precise definition of the bcl-6 locus and of the frequency of its involvement in NHL requires cloning and characterization of additional bcl-6 sequences and studying additional tumor cases. Nevertheless, the finding that various translocation partner chromosomes have been joined to the same region on chromosome 3 in cytogenetically heterogenous NHL cases supports the notion that rearrangement of the bcl-6 locus may represent the critical common denominator of translocations involving 3q27.

The second finding of this study is that the bcl-6 locus contains a gene which is expressed in B-cells. It is not clear at this stage whether the chromosomal breakpoints directly truncate coding or regulatory sequences of bcl-6, or, whether the gene remains intact with its regulation overridden by transcriptional control motifs juxtaposed by the translocation. The clustering of breakpoints in the seven studied NHL cases suggests, however, that bcl-6 may be a proto-oncogene which can contribute to NHL pathogenesis upon activation by chromosomal translocation. Results of this study will allow elucidation of the normal structure and function of the bcl-6 gene in order to understand the pathogen consequences of chromosomal translocation of bcl-6 and its role in lymphomagenesis.

REFERENCES FOR SECTION I

1. Gaidano, G., and Dalla-Favera, R., (1992) Oncogenes and tumor suppressor genes. In: *Neoplastic Hematopatholovy*, D. M. Knowles (ed.), Wilkins & Wilkins, pp 245–261.
2. Dalla-Favera, R., et al. (1982) Human c-myc oncogene is located on the region of chromosome 8 that is translocated in Burkitt lymphoma cells, *Proc. Natl. Acad. Sci. USA* 79:7824–7827.
3. Taub, R., et al. (1982) Translocation of c-myc gene into the immunoglobulin heavy chain locus in human Burkitt lymphoma and murine plasmacytoma cells, *Proc. Natl. Acad. Sci. USA* 79:7837–7841.
4. Bakhshi, A., et al. (1985) Cloning the chromosomal breakpoint of t(14;18) human lymphomas: clustering around $J_H$ on chromosome 14 and near a transcriptional unit on 18, *Cell* 41:889–906.
5. Tsujimoto, U., et al. (1985) Involvement of the Bcl-2 gene in human follicular lymphoma, *Science* 228:1440–1443.
6. Cleary, M. L., and Sklar, J., (1985) Nucleotide sequence of a t(14;18) chromosomal breakpoint in follicular lymphoma and demonstration of a breakpoint-cluster region near a transcriptionally active locus on chromosome 18, *Proc. Natl. Acad. Sci. USA* 82:7439–7444.
7. Motokura, T., et al. (1991) A novel cyclin encoded by a bcl-1 linked candidate oncogene, *Nature* 350:512–514.
8. Raffeld, M., and Jaffe, E. S., (1991) Bcl-1, t(11;14), and mantle zone lymphomas, *Blood* 78:259–261.

9. Offit, K., et al. (1989) t(3;22) (q27;q11): A novel translocation associated with diffuse non-Hodgkin's lymphoma, *Blood* 74:1876–1879.
10. Bastard, C., et al. (1992) Translocations involving band 3q37 and Ig gene regions in non-Hodgkin's lymphoma, *Blood* 79:2527–2531.
11. Miller, S. A., et al. (1988) A simple salting out procedure for extracting DNA from human nucleated cells, *Nucleic Acids Res*, 16:1215–1218.
12. Feinberg, A. P., and Vogelstein, B., (1983) A technique for radiolabelling DNA restriction endonuclease fragments to high specific activity, *Anal. Biochem.*, 132:6–13.
13. Ravetch, J. V., et al. (1981) Structure of the human immunoglobulin μ locus: characterization of embryonic and rearranged J and D regions, *Cell*, 27:583–591.
14. Rao, P. H., et al. (1994) Subregional localization of 20 single-copy loci to chromosome 6 by fluorescence in situ hybridization, *Cyto. and Cell Genetics* 66:272–273.
15. Chirgwin, J. M., et al. (1979) Isolation of biologically active ribonucleic acid from sources enriched in ribonuclease, *Biochemistry*, 18:5294–5299.
16. Peschle, C., et al. (1984) Translocation and rearrangement of c-myc into immunoglobulin alpha heavy chain locus in primary cells from acute lymphocytic leukemia, *Proc. Natl. Acad. Sci. U.S.A.*, 81:5514–5518.
17. Showe, L. C., et al. (1985) Cloning and sequencing of a c-myc oncogene in a Burkitt's lymphoma cell line that is translocated to a germ line alpha switch region, *Mol. Cell. Biol.*, 5:501–509.
18. Neri, A., Barriga, et al. (1988) Different regions of the immunoglobulin heavy chain locus are involved in chromosomal translocations in distinct pathogenic forms of Burkitt lymphoma, *Proc. Natl. Acad. Sci. USA*, 85:2748–2752.
19. Rabbits, T. H., et al. (1991) Human immunoglobulin heavy chain genes: evolutionary comparisons of C mu, C delta and C gamma genes and associated switch sequences, *Nucleic Acids Res.*, 9:4509–4524.
20. Schmid, et al. (1991) *Nature*, 332:733.

EXPERIMENTAL DETAIL SECTION II

Introduction

The molecular analysis of specific chromosomal translocations has improved the understanding of the pathogenesis of non-Hodgkin lymphoma (NHL), a heterogeneous group of B-cell or, less frequently, T-cell malignancies (1,2). The (14;18) chromosomal translocation, which causes the deregulated expression of the anti-apoptosis gene BCL-2, plays a critical role in the development of follicular lymphoma (FL) (3–6), which accounts for 20 to 30% of all NHL diagnoses (7). Burkitt's lymphoma (BL) and mantle-cell lymphoma, two relatively rare NHL types, are characterized by chromosomal translocations causing the deregulated expression of the cell-cycle progression genes C-MYC and the BCL-1/cyclin D1, respectively (8–15).

Relatively little is known about the molecular pathogenesis of diffuse large cell lymphoma (DLCL), the most frequent and most lethal human lymphoma (7). DLCL accounts for ~40% of initial NHL diagnoses and is often the final stage of progression of FL(7). A small percentage of DLCL display C-MYC rearrangements (16) and 20 to 30% display alterations of BCL-2 reflecting the tumor's derivation from FL (17). However, no consistent molecular alteration has been identified that is specific for DLCL.

Chromosomal translocations involving reciprocal recombinations between band 3q27 and several other chromosomal sites are found in 8 to 12% of NHL cases, particularly in DLCL (18–19). From NHL samples displaying recombinations between 3q27 and the immunoglobulin (Ig) heavy chain locus on 14q32, the chromosomal junctions of several (3;14)(q27;q32) translocations were cloned and identified a cluster of breakpoints at a 3q27 locus named BCL-6.

Experimental Results

Figure 10A:
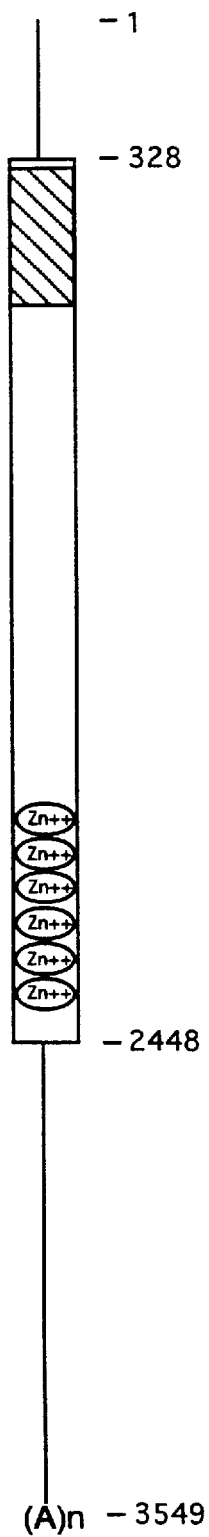

To isolate normal BCL-6 cDNA, a cDNA library constructed form the NHL cell line Bjab (22) was screened with a probe (20–21) derived from the chromosomal region flanking the breakpoints of two t(3;14)(q27;32) cases. A phage cDNA library constructed from RNA of the Bjab lymphoma cell line was screened ($1 \times 10^6$ plaques) by plaque hybridization with the Sac 4.0 probe that had been $^{32}$P-labelled by random priming (22). Sequence analysis (FIGS. 10A–10B) revealed that the longest clone (3549 bp), approximately the same size as BCL-6 RNA, codes for a protein of 706 amino acids with a predicted molecular mass of 79kD. The putative ATG initiation codon at position 328 is surrounded by a Kozak consensus sequence (23) and is preceded by three upstream inframe stop codons. The 1101-bp 3'-untranslated region contains a polyadenylation signal followed by a track of poly(A). These features are consistent with BCL-6 being a functional gene.

The $NH_2$— and COOH— termini of the BCL-6 protein (FIGS. 10A–10B) have homologies with "zinc-finger" transcription factors (24). BCL-6 contains six $C_2H_2$ zinc-finger motifs (FIG. 10A) and a conserved stretch of six amino acids (the H/C link) connecting the successive zinc-finger repeats (25), BCL-6 can be assigned to the Krüppel-like subfamily of zinc-finger proteins. The $NH_2$— terminal region of BCL-6 is devoid of the FAX (27) and KRAB (28) domains sometimes seen in Krüppel-related zinc-finger proteins, but it does have homologies (FIG. 11) with other zinc-finger transcription factors including the human ZFPJS protein, a putative human transcription factor that regulates the major histocompatibility complex II promoter, the Tramtrack (ttk) and Broad-complex (Br-c) proteins in Drosophila that regulate developmental transcription (29), the human KUP protein (31), and the human PLZF protein, which is occasionally involved in chromosomal translocations in human promyelocytic leukemia (32). The regions of $NH_2$-terminal homology among ZFPJS, ttk, Br-c, PLZF and BCL-6 also share some degree of homology with viral proteins (e.g. VA55R) of the poxvirus family (33) as well as with the Drosophila kelch protein involved in nurse cell-oocyte interaction (34). These structural homologies suggest that BCL-6 may function as a DNA-binding transcription factor that regulates organ development and tissue differentiation.

The cDNA clone was used as a probe to investigate BCL-6 RNA expression in a variety of human cell lines by Northern blot analysis. A single 3.8 kb RNA species was readily detected in cell lines derived from mature B-cells, but not from pro-B-cells or plasma cells, T cells or other hematopoietic cell lineages. The BCL-6 RNA was not detectable in other normal other tissues, except for skeletal muscle in which low level expression was seen. Thus, the expression of BCL-6 was detected in B-cells at a differentiation stage corresponding to that of DLCL cells. This selective expression in a "window" of B-cell differentiation suggests that BCL-6 plays a role in the control of normal B-cell differentiation and lymphoid organ development.

Figure 12:
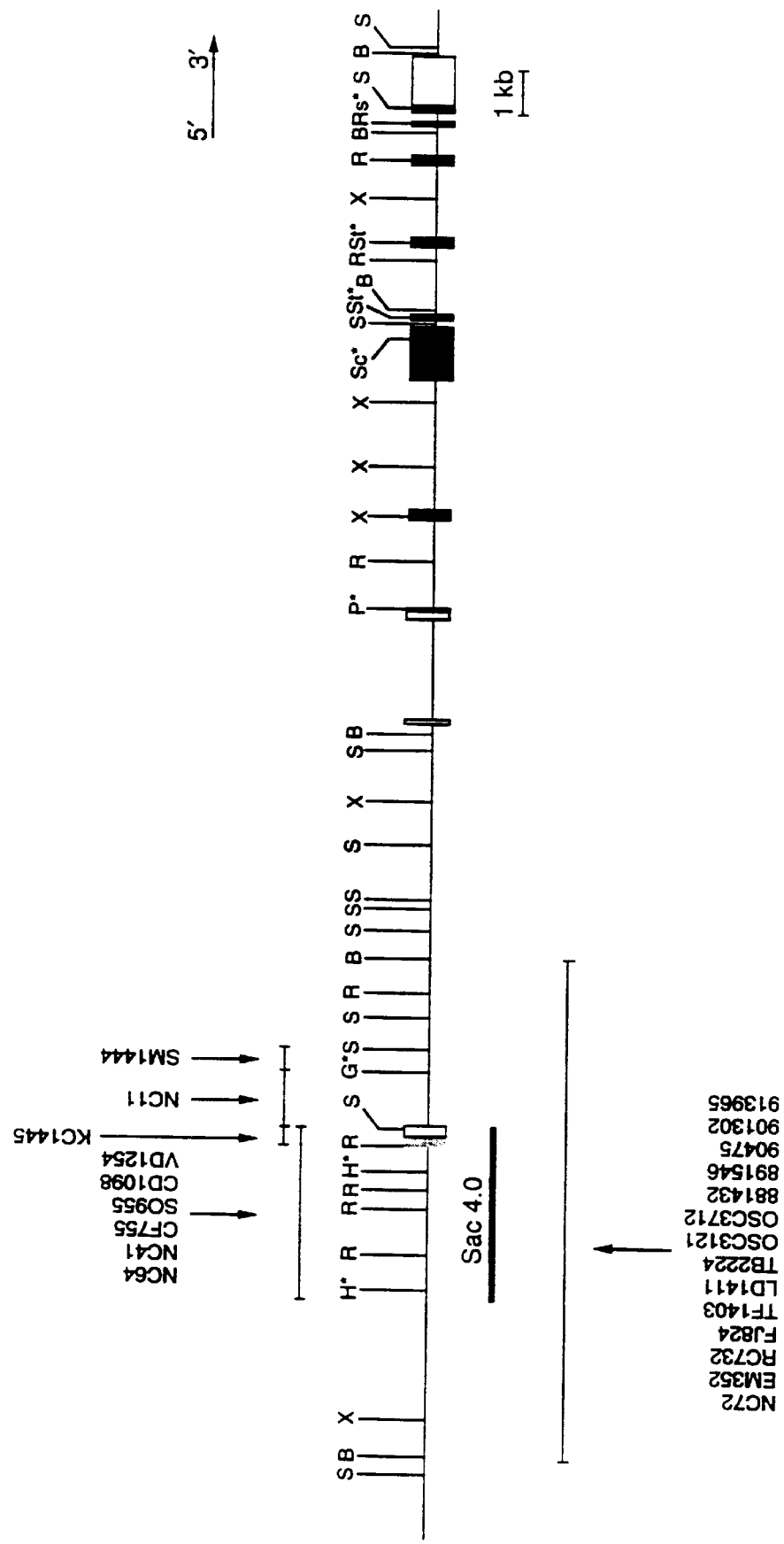
FIG. 12: Exon-intron organization of the BCL-6 gene and mapping of breakpoints detected in DLCL. Coding and non-coding exons are represented by filled and empty boxes, respectively. The position and size of each exon are approximate and have been determined by the pattern of hybridization of various cDNA probes as well as by the present of shared restriction sites in the genomic and cDNA. The putative first, second and third exons have been sequenced in the portions overlapping the cloned cDNA sequences. The transcription initiation site has not been mapped (shaded box on 5' side of first exon). Patient codes (e.e. NC11, 891546 etc.) are grouped according to the rearranged patterns displayed by tumor samples. Arrows indicate the breakpoint position for each sample as determined by restriction enzyme/hybridization analysis. For samples KC1445 and SM1444, the breakpoints have been cloned and the precise positions are known. Restriction sites marked by asterisks have been only partially mapped within the BCL-6 locus. Restriction enzyme symbols are: S, Sac I; B, Bam HI; X, Xba I; H, Hind III, R, Eco RI; G, Bgl II; P, Pst I; Sc, Sca I; St, Stu I; Rs, Rsa I. Tumor samples were collected and analyzed for histopathology at Memorial Sloan-Kettering Cancer Center or at Columbia University.

To characterize the BCL-6 genomic locus, the same cDNA probe to screen a genomic library from human placenta was used. A phage genomic library constructed from normal human placenta DNA (Stratagene) was screened ($8 \times 10^5$ plaques) with the BCL-6 cDNA. Twelve overlapping clones spanning ~50kb of genomic DNA were isolated. After restriction mapping, the position of various BCL-6 exons was determined by Southern hybridization using various cDNA probes. By restriction mapping, hybridization with various CDNA probes, and limited nucleotide sequencing, the BCL-6 gene was found to contain at least ten exons spanning ~26 kb of DNA (FIG. 12). Sequence analysis of the first and second exons indicated that they are noncoding and that the translation initiation codon is within the third exon.

Various cDNA and genomic probes were used in Southern (DNA) blot hybridizations to determine the relationship between 3q27 (Table 1). Monoallelic rearrangements of BCL-6 were detected in 12 of 17 tumors by using combinations of restriction enzymes (Bam HI and Xba I) and probe which explore ~16 kb within the BCL-6 locus. These 12 positive cases carry recombinations between 3q27 and several different chromosomes (Table 1), indicating that heterogeneous 3q27 breakpoints cluster in a restricted genomic locus irrespective of the partner chromosome involved in the translocation. Some DLCL samples (5 of 17) do not display BCL-6 rearrangements despite cytogenetic alterations in band 3q27, suggesting that another gene is involved or, more likely, that there are other breakpoint clusters 5' or 3' to BCL-6. If the latter is true, the observed frequency of BCL-6 involvement in DLCL (33%, see below) may be an underestimate.

TABLE 1

Frequency of BCL-6 rearrangements in DLCL carrying chromosomal translocations affecting band 3q27

| Translocation | Fraction of tumors with BCL-6 rearrangements |
| --- | --- |
| t (3;14) (q27;q32) | 4/4 |
| t (3;22) (q27;q11) | 2/3 |
| t (3;12) (q27;q11) | 1/1 |
| t (3;11) (q27;q13) | 1/1 |
| t (3;9) (q27;p13) | 0/1 |
| t (3;12) (q27;q24) | 0/1 |
| der (3) t (3;5) (q27;q31) | 1/1 |
| t (1;3) (q21;q27) | 1/1 |
| t (2;3) (q23;q27) | 1/1 |
| der (3) t (3;?) (q27;?) | 1/3 |

Tumor samples listed in the Table were collected and analyzed for histopathology and cytogenetics at Memorial Sloan-Kettering Cancer Center.

A panel of tumors not previously selected on the basis of 3q27 breakpoints but representative of the major subtypes of NHL as well as of other lymphoproliferative diseases was analyzed. Similar rearrangements were detected in 13 of 39 DLCL, but not in other cases including other NHL subtypes (28 FL, 20 BL, and 8 small lymphocytic NHL), acute lymphoblastic leukemia (ALL; 21 cases), and chronic lymphocytic leukemia (CLL; 31). These findings indicate that BCL-6 rearrangements are specific for and frequent in DLCL. In addition, the frequency of rearrangements in DLCL (33%) significantly exceeds that (8 to 12%) reported at the cytogenetic level, suggesting that some of the observed rearrangements may involve submicroscopic chromosomal alterations undetectable at the cytogenetic level.

All the breakpoints in BCL-6 mapped to the putative 5' flanking region, the first exon or the first intron (FIG. 12). For two patients that carry (3;12)(q27;q32) translocations, the chromosomal breakpoints have been cloned and precisely mapped to the first intron (SM1444) or to 5' flanking sequences (KC1445) of BCL-6 on 3q27, and to the switch region of IgH on 14q32 (20–21). In all rearrangements, the coding region of BCL-6 was left intact whereas the 5' regulatory region, presumably containing the promoter sequences, was either completely removed or truncated. The resultant fusion of BCL-6 coding sequences to heterologous (from other chromosomes) or alternative (within the BCl-6 locus) regulatory sequences may disrupt the gene's normal expression pattern. A BCL-6 transcript of normal size was detected by Northern blot analysis of DLCL cells carrying either normal or truncated BCL-6. Some of the truncations were in the 5' flanking sequences and would therefore not be expected to generate structurally abnormal transcripts.

Experimental Discussion

Zinc-finger encoding genes are candidate oncogenes as they have been shown to participate in the control of cell proliferation, differentiation, and organ pattern formation (24). In fact, alterations of zinc-finger genes have been detected in a variety of tumor types. These genes include PLZF (32) and PML (35–38) in acute promyeloctic leukemia, EVI-1 (38–39) in mouse and human myeloid leukemia, TTG-1 (40) in T-cell CLL, HTRX (41–43) in acute mixed-lineage leukemia, and WT-1 (44) in Wilm's tumor. Terminal differentiation of hematopoietic cells is associated with the down-regulation of many Krüppel-type zinc-finger genes. Thus, constitutive expression of BCL-6, caused by chromosomal rearrangements, interferes with normal B-cell differentiation, thereby contributing to the abnormal lymph node architecture typifying DLCL.

Given that DLCL accounts for ~80% of NHL mortality (7), the identification of a specific pathogenetic lesion has important clinicopathologic implications. Lesions in BCL-6 may help in identifying prognostically distinct subgroups of DLCL. In addition, since a therapeutic response can now be obtained in a substantial fraction of cases (7), a genetic marker specific for the malignant clone may be a critical tool for the monitoring of minimal residual disease and early diagnosis of relapse (45).

The gene cloned from chromosomal translocations affecting band 3q27, which are common in DLCL codes for a 79 kD protein that is homologous with zinc-finger transcription factors. In 33% (13/39) of DLCL samples, but not in other types of lymphoid malignancies, the BCL-6 gene is truncated within its 5' noncoding sequences, suggesting that its expression is deregulated. Thus, BCL-6 is a proto-oncogene specifically involved in the pathogenesis of DLCL.

REFERENCES FOR SECTION II

1. Chaganti, R. S. K., et al. (1989) *Molecular Diagnostics of Human Cancer*, pp. 33–36.
2. Nathwani, B. N., (1992) *Neoplastic Hemolatholovy*, pp. 555–601.
3. Tsujumoto, Y., et al. (1985) *Science* 228:1440.
4. Cleary, M. L. and Sklar, J., (1985) *Proc. Natl. Acad. Sci. U.S.A.* 82:7439.
5. Bakshi, A., et al. (1985) *Cell* 41:899.
6. Korsmeyer, S. J., (1992) *Blood* 80:879.
7. Magrath, I. T., (1990) *The Non-Hodgkin's Lymphomas* pp. 1–14.
8. Dalla-Favera, R., et al. (1982) *Proc. Natl. Acad. Sci. U.S.A.* 79:7824.
9. Taub, R., et al. (1982) *Proc. Natl. Acad. Sci. U.S.A.* 79:7837.
10. Dalla-Favera, R., (1993) *Causes and Consequences of Chromosomal Translocations* pp. 313–321.
11. Tsujimoto, Y., et al. (1985) *Nature* 315:340.
12. Meeker, T. C., et al. (1989) *Blood* 74:1801.
13. Motokura, T., et al. (1991) *Nature* 350:512.
14. Williams, M. E., et al. (1991) *Blood* 78:493.
15. Raffeld, M., and Jaffe, E., (1991) *Blood* 78:259.

16. Ladanyi, M., et al. (1991) *Blood* 77:1057.
17. Offit, K., et al. (1989) *Bri. J. Haematol.* 72:178.
18. Offit, K., et al. (1989) *Blood* 74:1876.
19. Bastard, C., et al. (1992) *Blood* 79:2527.
20. Ye, B. H., et al. (1993) *Cancer Res* 53:2732.
21. Baron, B. W., et al. (1993) *Proc. Natl. Acad. Sci. U.S.A.* 90:5262.
22. Feinbert, A. P., and Vogelstein, B., (1983) *Anal. Biochem.* 132:6.
23. Kozak, M., (1989) *J. Cell. Biol* 108:229.
24. El-Baradi, T., and Pieler, T., (1991) *Mech. Dev* 35:155.
25. Rosenbert, U. B., et al. (1989) *Nature* 319:336.
26. Bellefroid, E. J., et al. (1989) *DNA* 8:377.
27. Knochel, W., et al. (1989) *Proc. Natl. Acad. Sci. U.S.A.* 86:6097.
28. Bellefroid, E. J., et al. (1991) *DNA* 88:3608.
29. Harrison, S. D., and Travers, A. A., (1990) *EMBO J.* 9:207.
30. DiBello, R. R., et al. (1991) *Genetics* 129:385.
31. Chardin, P., et al. (1991) *Nucleaic Acid Res.* 19:1431.
32. Chen, Z., et al. (1993) *EMBO J.* 12:1161.
33. Koonin, E. V., et al. (1992) *Trends Biochem. Sci.* 17:213.
34. Xue, F., and Cooley, L., (1993) *Cell* 72:681.
35. de Thé, H., et al. (1991) *Cell* 66:675.
36. Kazizuka, A., et al. (1991) *Cell* 66:663.
37. Pandolfi, P. P., et al. (1991) *Oncogene* 6:1285.
38. Morishita, K., et al. (1988) *Cell* 54:831.
39. Fichelson, S., et al. (1992) *Leukemia* 6:93.
40. McGuire, E. A., et al. (1989) *Cell Biol.* 9:2124.
41. Djabali, M., et al. (1992) *Nature Genet.* 2:113.
42. Tkachuk, D. C., et al. (1992) *Cell* 71:691.
43. Gu, Y., et al. (1992) *Cell* 71:701.
44. Haber, D. A., et al. (1990) *Cell* 61:1257.
45. Medeiros, L. J., et al. (1992) *Neoplastic Hemopathology*, pp. 263–298.

EXPERIMENTAL DETAIL SECTION III

Introduction

Non Hodgkin's lymphoma (NHL), the most frequent tumor occurring in patients between the ages of 20 and 40, includes several distinct clinico-pathologic subtypes, among which diffuse lymphoma with a large cell component (DLLC) is the most clinically relevant in terms of morbidity and mortality (1). DLLC include intermediate-grade lymphomas with pure diffuse large-(DLCL), or mixed small- and large-cell (MX-D) histology, as well as high-grade immunoblastic (IMB) lymphoma. These tumors can occur "de novo", accounting for 30–40% of initial NHL diagnosis and, in addition, can represent the final "transformation" stage of follicular lymphomas (FL), small lymphocytic lymphoma and chronic lymphocytic leukemia. Considered together, "de novol" and "post-transformation" DLLC account for up to 80% of NHL mortality (1).

During the past decade, abnormalities involving proto-oncogenes and tumor suppressor genes have been identified in association with distinct NHL subtypes (2). These genetic lesions represent important steps in lymphomagenesis as well as tumor-specific markers which have been exploited for diagnostic and prognostic purposes (3,4). Examples include alterations of the MYC oncogene in Burkitt lymphoma (BL), and of the BCL-2 and BCL-1 oncogenes in FL and mantle-cell NHL, respectively. With respect to DLLC, several molecular alterations have been detected at variable frequency, but none has been specifically or consistently associated with the disease (2). In this invention the frequency and disease-specificity of BCL-6 (5–10) rearrangements among the principal categories of lymphoproliferative disease, including different NHL subtypes, acute and chronic lymphoid leukemias and multiple myeloma is demonstrated.

Materials and Methods

Samples of lymphnode biopsies, bone marrow aspirates and peripheral blood were collected by standard diagnostic procedures during the course of routine clinical evaluation in the Division of Surgical Pathology, Department of Pathology, Columbia University. In all instances, the specimens were collected before specific anti-tumor treatment. Diagnoses were based on the results of histopathologic, immunophenotypic and immunogenotypic analysis (11). In all cases, the fraction of malignant cells in the pathologic specimen was at least 70% as determined by cytofluorimetric or immunohistochemical analysis of cell-surface markers or antigen receptor (immunoglobulin heavy chain and T cell receptor β chain) gene rearrangement analysis (11).

Genomic DNA was prepared from diagnostic specimens by cell lysis, proteinase K digestion, phenol-chloroform extraction and ethanol precipitation. For Southern blot analysis, 6 μg of DNA were digested with the appropriate restriction endonuclease, electrophoresed in a 0.8% agarose gel, denatured, neutralized and transferred to Duralose filters (Stratagene, La Jolla, Calif.). Filters were then hybridized with the BCL-6-specific Sac 4.0 probe (10) that had been $^{32}$P-labelled by the random priming technique. After hybridization, filters were washed in 0.2× SSC (1× SSC= 0.15M NaCl+0.015M sodium citrate / 0.5% sodium dodecyl sulfate) for 2 hours at 60° C. and then subjected to autoradiography for 24–48 hours at −80° C. using intensifying screens.

All NHL cases were also analyzed for rearrangement of the BCL-2 gene using the previously described probes corresponding to the MBR and MCR regions. Immunophenotypic analysis of immunoglobulin and cell surface marker expression was performed as previously described (11).

Comparisons of histologic subsets with or without BCL-6 rearrangement were made utilizing the method of inferences from proportions (12).

Experimental Results

The tumor panel (Table 2) used for this study is representative of the major categories of lymphoproliferative disease including NHL, 125 cases, ALL 45, CLL 51 and MM 23. The NHL series was representative of low- 41, intermediate- 45 and high-grade 24 subtypes according to the Working Formulation. Fifteen cases of cutaneous T-cell NHL were also included.

The presence of BCL-6 rearrangements was analyzed by Southern blot hybridization of tumor DNAs using a probe (Sac 4.0) (10) and restriction enzymes (BamHI and XbaI) which, in combination, explore a region of 15.2 Kb containing the 5' portion of the BCL-6 gene (first exon, 7.5 Kb of first intron and 7.4 Kb of 5' flanking sequences) (10). This region was previously shown to contain the cluster of breakpoints detected in NHL. No additional rearrangements were found using probes and restriction enzymes exploring approximately 10 kb either 5' or 3' to BCL-6 sequences The results of this analysis are summarized in Table 2 and representatively shown in FIGS. 13A–13B. All cases of ALL, CLL and MM showed a normal BCL-6 gene.

Eighteen of the 125 NHL cases displayed BCL-6 rearrangements. Among distinct NHL histologic subtypes, rearrangements were detected in 16/45 (35.5%) DLLC and in 2/31 (6.4%) FL (p<0.001). One of these 2 FL cases showed both follicular and diffuse patterns of growth. Among DLLC, rearrangements were significantly more frequent in DLCL (15/33, 45.4%) than in MX-D (1/10, 10%) (p<0.01), suggesting that these genetic lesions may be specifically associated with the diffuse large cell component of these tumors. All of the DLLC cases displaying BCL-6 rearrangements lacked BCL-2 rearrangements which were found in only two 2 DLLC cases. Although cytogenetic data were not available for the panel of tumors studied, the frequency of BCL-6 rearrangements far exceeds that expected for 3q27 aberrations (10–12% in DLLC) (8, 9), suggesting that BCL-6 rearrangements can occur as a consequence of submicroscopic chromosomal aberrations.

In order to determine whether the presence of BCL-6 rearrangements correlated with distinct immunophenotypic features of DLLC, the entire panel was analyzed for expression of immunoglobulin κ and λ light chains, and B cell-associated antigens CD19, CD20 and CD22 (11). As expected, the expression of these markers was variable in the DLLC cases tested. However, no correlation with the BCL-6 rearrangement status was found.

TABLE 2

Rearrangements of the BCL-6 gene in lymphoid tumors

| TUMOR | HISTOTYPE | REARRANGED/TESTED | % |
|---|---|---|---|
| NHL | | | |
| Low grade: | SL | 0/10 | 0 |
| | SCC-F | 2*/18 | 11 |
| | MX-F | 0/13 | 0 |
| Intermediate grade: | MX-D | 1/10 | 10 |
| | DLCL | 15/33 | 45 |
| | SCC-D | 0/2 | 0 |
| High grade: | IMB | 0/2 | 0 |
| | SNCL | 0/22 | 0 |
| Others: | CTCL | 0/15 | 0 |
| ALL | B-lineage: | 0/34 | 0 |
| | T-lineage: | 0/11 | 0 |
| CLL | B-lineage: | 0/41 | 0 |
| | T-lineage: | 0/10 | 0 |
| MM | | 0/23 | 0 |

NHL, non-Hodgkin's lymphoma; ALL, acute lymphoblastic leukemia; CLL, chronic lymphocytic leukemia; MM, multiple myeloma; SL, small lymphocytic; SCC-F, follicular small cleaved cell; MX-F, follicular mixed; MX-D, diffuse mixed cell; DLCL, diffuse large cell; SCC-D, diffuse small cleaved cell; IMB, immunoblastic; SNCL, small non-cleaved cell lymphoma; CTCL, cutaneous T-cell lymphoma. *: one case showed follicular and diffuse growth patterns.

Experimental Discussion

In this study, BCL-6 rearrangement is established as the most frequent abnormality detectable in DLLC. Previous studies have indicated MYC and BCL-2 rearrangements detectable in 5–20% and 20% of DLLC, respectively (13). Compared to those lesions, which are also commonly associated with Burkitt's lymphoma (MYC) and FL (BCL-2), BCL-6 rearrangements appear to be more disease-specific since they were exclusively found in DLLC with the exception of 2 of 45 FL cases. Considering that one of these two FL cases displayed areas of diffuse histology, it is conceivable that BCL-6 rearrangements may be occasionally associated with atypical FL cases with mixed follicular and diffuse components. The recurrent and specific association between DLLC and structural lesions of a gene coding for a zinc finger-type transcription factor related to several known proto-oncogenes 10 suggests that these abnormalities may play a role in pathogenesis of DLCL.

Among the heterogeneous DLLC spectrum, BCL-6 rearrangements were significantly more frequent in tumors displaying a pure diffuse large cell histology (DLCL) all of which lacked BCL-2 rearrangements. Considering that DLCL can originate both "de novo" and from the "transformation" of FL, and that the latter typically carry BCL-2 rearrangements, results suggest that BCL-6 rearrangements may be specifically involved in the pathogenesis of "de novo" DLLC. This conclusion is consistent with recent findings indicating that other genetic alterations, namely the inactivation of the p53 tumor suppressor gene, may be involved in the transformation of FL to DLLC (14).

The results presented herein have relevant diagnostic and prognostic implications. DLLC represent a heterogeneous group of neoplasms which are treated homogeneously despite the fact that only 50% of patients experience long-term disease free survival (1). The presence of a marker such as BCL-6 rearrangement identifies a sizable subset of cases with a distinct pathogenesis and, distinct biological behavior.

The pathogenesis of non-Hodgkin lymphoma with a large-cell component (DLLC, including diffuse large-cell, DLCL, diffuse mixed-cell, MX-D, and immunoblastic, IMB) is unknown. The incidence and disease-specificity of BCL-6 rearrangements in a large panel of lymphoid tumors, including acute and chronic lymphoid leukemias (96 cases), various NHL types (125 cases), and multiple myelomas (23 cases) has been tested. BCL-6 rearrangements were found in 16/45 (35.5%) DLLC, more frequently in DLCL (15/33, 45%) than in MX-D (1/10, 10%), in 2/31 (6.4%) follicular NHL, and in no other tumor types. BCL-6 rearrangements represent the first genetic lesion specifically and recurrently associated with DLLC and should prove useful for understanding the pathogenesis as well as for the clinical monitoring of these tumors.

REFERENCES FOR SECTION III

1. Magrath, I. T. (1990) The Non-Hodgkin's Lymphomas: An Introduction, The Non-Hodgkin's Lymphomas, Edward Arnold, London, p 1.
2. Gaidano, G., and Dalla-Favera, R. (1993) Biologic and molecular characterization of non-Hodgkin's lymphoma, *Curr. Opin. Oncol.* 5:776.
3. Gribben, J. G., et al. (1991) Immunologic purging of marrow assessed by PCR before autologous bone marrow transplantation for B-cell lymphoma, *N. Engl. J. Med.* 325:1525.
4. Yunis, J. J., et al. (1989) Bcl-2 and other genomic alterations in the prognosis of large-cell lymphoma, *N. Enql. J. Med.* 320:1047.
5. Ye, B. H., et al. (1993) Cloning of bcl-6, the locus involved in chromosome translocations affecting band 3q27 in B-cell lymphoma, *Cancer Res.* 53:2732.
6. Baron, B. W., et al. (1993) Identification of the gene associated with the recurring chromosomal translocations t(3;14)(q27;q32) and t(3;22) (q27;q11) in B-cell lymphomas, *Proc. Natl. Acad. Sci. USA* 90: 5262.
7. Kerckaert, J. P., et al. (1993) LAZ3, a novel zinc-finger encoding gene, is disrupted by recurring chromosome 3q27 translocations in human lymphomas, *Nature Genet.* 5:66.
8. Offit, K, et al. (1989) t(3;22 (q27;q11): A novel translocation associated with diffuse non-Hodgkin's lymphoma, *Blood* 74: 1876.
9. Bastard, C, et al. (1992) Translocations involving band 3q27 and Ig gene regions in non-Hodgkin's lymphoma, *Blood* 79: 2527.
10. Ye, B. H., et al. (1993) Alterations of a zinc-finger encoding gene, BCL-6, in diffuse large-cell lymphoma, *Science* 262:747.
11. Knowles, D. M. (ed.) (1992) *Neoplastic Hemopathology,* Williams & Wilkins, Baltimore, Md.
12. Armitage, P., (1977) Statistical methods in medical research, Blackwell Scientific Publications, London, p. 11.
13. Chaganti, R. S. K., et al. (1989) Specific translocations in non-Hodgkin's lymphoma: incidence, molecular 14. Lo Coco, F., et al. (1993) p53 mutations are associated with histologic transformation of follicular lymphoma, *Blood* 82:2289.

EXPERIMENTAL DETAIL SECTION IV

Introduction

Non-Hodgkin lymphomas (NHL) represent one of the most common malignancies associated with human immunodeficiency virus (HIV) infection, and are recognized as an acquired immunodeficiency syndrome (AIDS)-defining condition (1–3). Since their initial observation in 1982 (4), the incidence of AIDS-associated NHL (AIDS-NHL) has been consistently increasing (1, 2), and they now represent the most frequent HIV-associated malignancy in some AIDS risk groups, namely the hemophiliacs (5). Indeed, some estimates project that 10 to 20% of all new NHL cases in the United States may eventually be related to AIDS (6).

AIDS-NHL are almost invariably B-cell derived NHL (1, 2, 7–12). When compared with NHL of similar histology arising in the immunocompetent host, AIDS-NHL display distinctive clinical features, including late stage at presentation, poor prognosis, and the frequent involvement of extranodal sites (1, 2, 7–12). Systemic AIDS-NHL are histologically heterogeneous, and have been initially classified into three distinct categories, including small non cleaved cell lymphoma (SNCCL), large non cleaved cell lymphoma (LNCCL), and large cell-immunoblastic plasmacytoid lymphoma (LC-IBPL) (7, 9). Subsequently, most investigators have agreed to classify LNCCL and LC-IBPL as a single category under the term of diffuse large cell lymphoma (DLCL).

Some progress has been made in elucidating the molecular pathogenesis of AIDS-SNCCL (1–3). AIDS-SNCCL is associated at variable frequency with multiple genetic lesions, including Epstein Barr virus (EBV) infection, c-MYC translocation, RAS gene family mutation, and p53 inactiviation by point mutation and allelic loss (1, 3, 13–25). On the other hand, the pathogenesis of AIDS-DLCL is relatively less defined. EBV infection appears to be the only genetic lesion associated with a significant fraction of these tumors, particularly with the subset displaying plasmacytoid features, p53 lesions have not been found and c-MYC activation is restricted to a small minority of cases (1–3, 13–25).

Materials and Methods

Pathologic samples. Biopsy samples of lymph node, bone marrow, peripheral blood, or other involved organs from forty patients with AIDS were collected during the course of standard diagnostic procedures. Thirty-two samples were derived from patients referred to the Department of Pathology, New York University, New York, N.Y. or to the Department of Pathology, Columbia University, New York, N.Y. Eight samples were derived from patients referred to the Departments of Hematology and Pathology, University of Southern California School of Medicine, Los Angeles, Calif. Diagnosis was based on analysis of histopathology, immunophenotypic analysis of cell surface markers, and immunogenotypic analysis of Immunoglobulin (Ig) gene rearrangement (32). In most cases, the fraction of malignant cells in the pathologic specimen was greater than 80%, as determined by cell suspension cytofluorometric or tissue section immunohistochemical analysis of cell surface markers and by Ig gene rearrangement analysis.

DNA extraction and Southern blot analysis. DNA was purified by digestion with proteinase K, "salting out" extraction, and precipitation by ethanol (33). For Southern blot analysis (34), 6 µg of DNA was digested with the appropriate restriction endonuclease, electrophoresed in a 0.8% agarose gel, denatured, neutralized, transferred to Duralon filters (Stratagene, LA Jolla, Calif.), and hybridized to probes which had been $^{32}$P-labeled by the random primer extension method (35). Filters were washed in 0.2× SSC (NaCl/Na citrate)/0.5% sodium dodecyl sulphate (SDS) for 2 hours at 60° C. and then autoradiographed using intensifying screens (Quanta III; Dupont, Boston, Mass.).

DNA probes. Immunoglobulin gene rearrangement analysis was performed using a $J_H$ probe(36) (a gift of Dr. Korsmeyer) on HindIII, EcoRI, and BamHI digests. The organization of the BCL-6 locus was investigated by hybridization of XbaI, BazHI, and BglII digested DNA to the human BCL-6 probe Sac4.0 (26–27). In selected cases, a second probe representative of the BCL-6 locus, Sac0.8, was also used. The organization of the c-MYC locus was analyzed by hybridization of EcoRI and HindIII digested DNA to the human c-MYC locus was analyzed by hybridization of EcoRI and HindIII digested DNA to the human c-MYC probe MC413RC, representative of the third exon of the c-MYC gene (37). The presence of the EBV genome was investigated with a probe specific for the EBV termini (5.2 Kb BamHI-EcoRI fragment isolated from the fused BamHI terminal fragment NJ-het) (38).

Experimental Results

Forty cases of systemic AIDS-NHL were studied, including 13 SNCCL and 24 DLCL (8 LNCCL and 16 LC-IBPL). In addition, three cases of CD30+ lymphomas, which have been sporadically reported in AIDS (39), were also included. All cases displayed a predominant monoclonal B-cell population as determined by Ig gene rearrangement analysis.

Figure 14A:
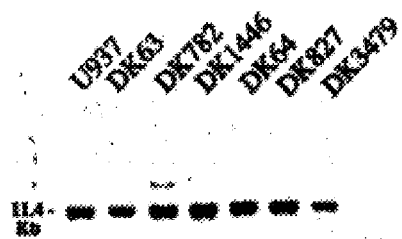
FIGS. 14A–14C: Analysis of BCL-6 rearrangements in AIDS-NHL (FIGS. 14A–14C). DNAs were digested with BamHI (FIG. 14A) or XbaI (FIGS. 14B and 14C) and hybridized to probes Sac4.0 (FIGS. 14A and 14B) or Sac0.8 (FIG. 14C). The BCL-6 germline bands detected by BamHI (11.4 Kb) and XbaI (14 Kb) are indicated. U937 was used as a BCL-6 germline control. Among the cases shown, rearrangements were detected in cases DK782, DK827, and DS16, represented by AIDS-DLCL.
Figure 14B:
Figure 14C:
Figure 15:
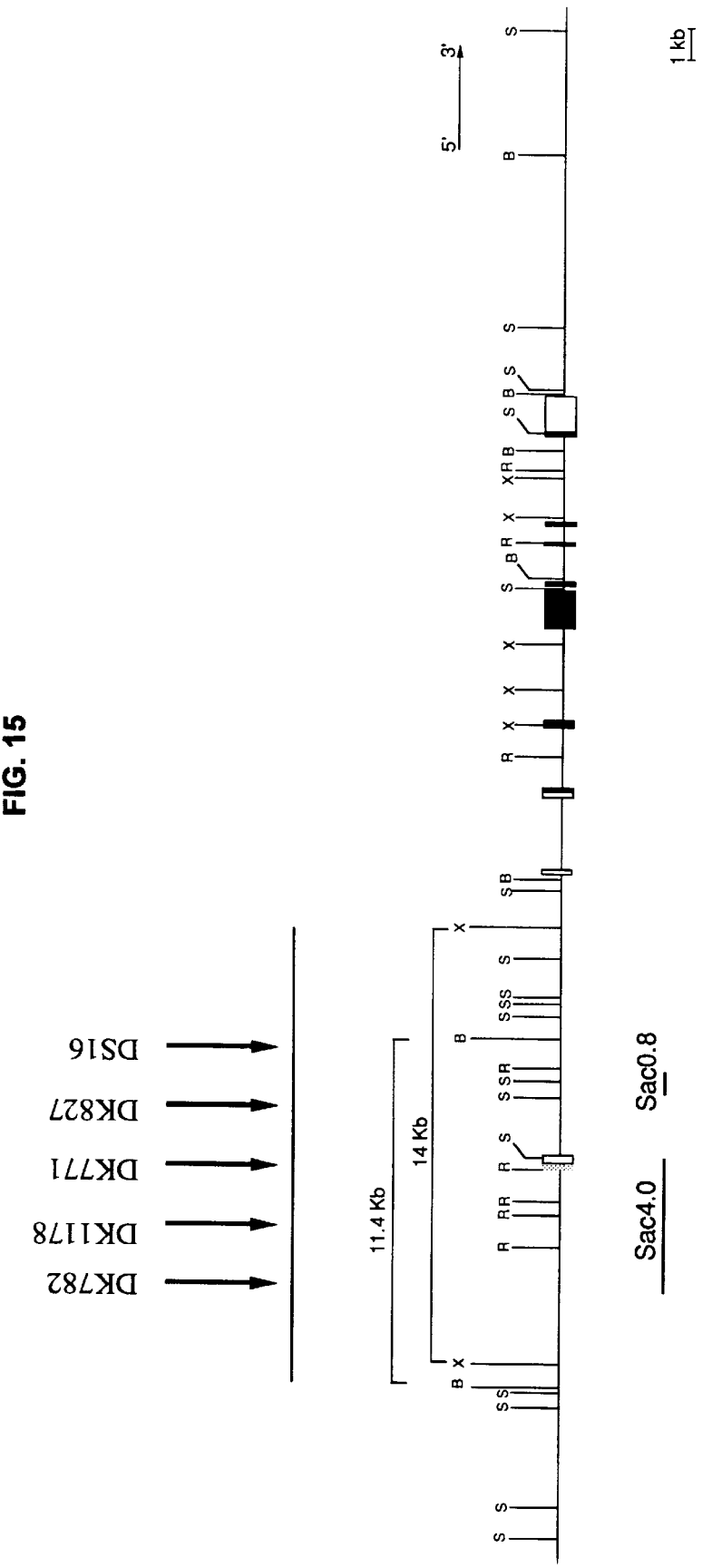
FIG. 15: Restriction map of the germline BCL-6 locus. Exon-intron organization of the BCL-6 gene. Coding and noncoding exons are represented by filled and empty boxes, respectively. The transcription initiation site has not been mapped (shaded box on 5' side of first exon). The breakpoints detected in AIDS-NHL are indicated by arrows. Restriction enzyme symbols are: S, SacI; B, BamHI; X, XbaI, R, EcoRI. RE, restriction enzyme.

Analysis of BCL-6 rearrangements. The BCL-6 gene contains at least 9 exons spanning approximately 26 Kb of genomic DNA (27). Sequence analysis has shown that the first exon is non-coding and that the translation initiation codon is located within the third exon (27). Rearrangements of BCL-6 can be detected by Southern blot analysis using a probe (Sac4.0) and restriction enzymes (BamHI and XbaI) which, in combination, explore a region of 15.2 Kb containing the 5' portion of the BCL-6 gene (27) (FIGS. 14A–14C). This same region was previously shown to contain the cluster of chromosomal breakpoints detected in NHL of the immunocompetent host (27, 29). Cases showing an abnormally migrating band in only one digest were further studied by hybridizing the Sac4.0 probe to additional digests (BglII) or, alternatively, by hybridizing BamHI and XbaI digests to a probe (Sac0.8) derived from the BCL-6 first intron, which, being located 3' of the breakpoint cluster, explores the reciprocal chromosome 3 (FIGS. 14A–14C). Only cases showing abnormally migrating bands with two restriction enzymes and/or two probes were scored as rearranged.

Rearrangements of BCL-6 were detected 5/24 AIDS-DLCL (20.8%), both in the LNCCL (2/8; 25%) and in the LC-IBPL (3/16; 18.7%) variants (Table 3 and FIGS. 14A–14C). All cases of AIDS-SNCCL and CD30+ lymphomas displayed a germline BCL-6 locus. The location of the breakpoints detected in AIDS-HNL corresponds to the pattern most commonly observed in DLCL of the immunocompetent host.

TABLE 3

Frequency of BCL-6 rearrangements in AIDS-NHL

| SNCCL[a] | LNNCL | DLCL[b] LC-IBPL | CD30 + NHL[c] |
|---|---|---|---|
| 0/13 | 2/8 | 3/16 | 0/3 |

[a]: SNCCL, small non cleaved cell lymphoma
[b]: DLCL, diffuse large cell lymphoma. The DLCL included in the panel can be further distinguised into two subgroups (LNCCL, large non cleaved cell lymphoma; and LC-IBPL, large cell immunoblastic-plasmacytoid lymphoma) as previously reported (7,9).
[c]: Non-Hodgkin lymphoma expressing the CD30 cell surface antigen (39).

Other genetic lesions. The other genetic lesions investigated in the panel of AIDS-NHL included infection by EBV of the tumor clone, activation of the c-MYC and RAS proto-oncogenes, and inactivation of the p53 tumor suppressor gene. The experimental strategies used to investigate these lesions have been described in detail elsewhere (13, 45, 40). For some of the cases, the molecular characterization of these genetic lesions have been previously reported (13, 14, 41); for the other cases, it has been assessed in the course of this study.

Figure 16A:
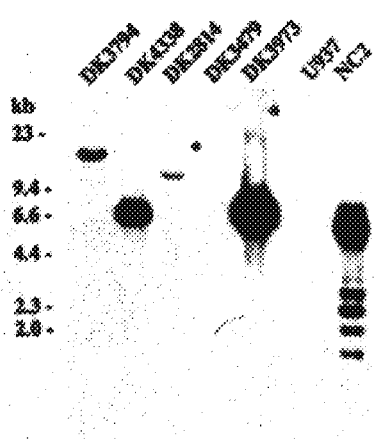
FIGS. 16A–16C: Analysis of EBV infection (FIG. 16A), c-MYC rearrangements (FIG. 16B), and p53 mutations (FIG. 16C) in AIDS-NHL.
Figure 16B:
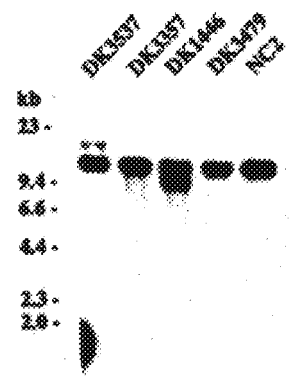
Figure 16C:
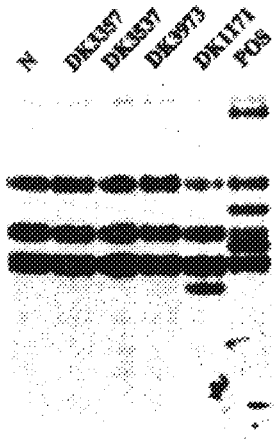

EBV infection was assessed by Southern blot hybridization using a probe representative of the EBV termini (38) which allows to analyze clonality in EBV-infected tissues (23) (FIGS. 16A–16C). A monoclonal infection was detected in 5/13 (38%) SNCCL, 17/24 DLCL (71%) [3/8 (37.5%) LNCCL and 14/16 (87.5%) LC-IBPL], and 3/3 (100%) CD30+ cases.

Rearrangements of c-MYC were tested by hybridizing HindIII and EcoRI digested DNAs with a probe representative of c-MYC exon 3(41) (FIGS. 16A–16C). Rearrangements were present in 13/13 SNCCL (100%), 5/24 (20.8%) DLCL [2/8 (25%) LNCCL and 3/16 (18.7%) LC-IBPL], and 2/3 CD30+cases.

Mutations of p53 and RAS were analyzed by a two step strategy. Single strand conformation polymorphism (SSCP) analysis was applied to p53 exons 5 through 9 (in 29 cases) or p53 exons 5 through 8 (in 6 cases) and to N-, K-, and H-RAS exons 1 and 2 (in 29 cases); cases displaying an altered electrophoretic pattern by SSCP were further studied by DNA direct sequencing of the PCR product. p53 mutations were scored in 8/13 (61.5%) SNCCL, but in none of the DLCL tested (0/22). Finally, RAS activation by point mutation was positive in 3/13 (23%) SNCCL and in 1/16 (6%) DLCL tested.

The molecular features of the cases displaying BCL-6 rearrangements are listed in Table 4. Overall, BCL-6 rearrangements were detected both in the presence and in the absence of clonal EBV infection of the tumor, whereas c-MYC alterations and p53 mutations were consistently absent in the cases displaying BCL-6 rearrangements.

TABLE 4

Molecular features of AIDS-DLCL[a]

| PATIENT | HISTOL.[b] | CLON-ALITY | BCL-6 | EBV | c-MYC | p53 | RAS |
|---|---|---|---|---|---|---|---|
| DK782 | LNCCL | + | + | − | − | − | − |
| DK1178 | LNCCL | + | + | − | − | − | − |
| DK1028 | LNCCL | + | − | − | − | − | − |
| DK3973 | LNCCL | + | − | + | − | − | − |
| DK773 | LNCCL | + | − | − | + | − | − |
| RDF834 | LNCCL | + | − | + | + | − | − |
| DK1452 | LNCCL | + | − | − | − | − | − |
| DK64 | LNCCL | + | − | + | − | − | + |
| DK771 | LC-IBPL | + | + | + | − | − | − |
| K827 | LC-IBPL | + | + | + | − | − | − |
| DS16 | LC-IBPL | + | + | + | − | − | ND |
| DK3537 | LC-IBPL | + | − | + | + | − | − |
| DK3357 | LC-IBPL | + | − | + | − | − | − |
| DK63 | LC-IBPL | + | − | + | − | − | − |
| DK1446 | LC-IBPL | + | − | + | + | − | − |
| DK3479 | LC-IBPL | + | − | − | − | − | − |
| DK2092 | LC-IBPL | + | − | + | − | − | − |
| DS17 | LC-IBPL | + | − | − | − | − | ND |
| DS45 | LC-IBPL | ND | − | + | − | − | ND |
| DS46 | LC-IBPL | + | − | + | + | − | ND |
| DS93 | LC-IBPL | + | − | + | − | − | ND |
| DS136 | LC-IBPL | + | − | + | − | − | ND |
| DS155 | LC-IBPL | + | − | + | − | − | ND |
| DS165 | LC-IBPL | + | − | + | − | − | ND |

[a]: The results of the analysis of EBV, c-MYC, p53 and RAS of some of these cases have been previously reported (14, 15, 41).
[b]: LNCCL, large non cleaved cell lymphoma; LC-IBPL, large cell-immunoblastic plasmacytoid lymphoma
[c]: ND, not done Experimental Discussion Diffuse large cell lymphoma (DLCL) represents the most frequent type of AIDS-NHL in the HIV-infected adult (8). Despite its epidemiologic relevance, the molecular pathogenesis of these tumors is largely unclarified (3). Analysis of the genomic configuration of BCL-6 in a panel of AIDS-NHL indicates that BCL-6 rearrangements are involved in approximately 20% of AIDS-DLCL, whereas they are consistently negative in AIDS-SNCCL. In this respect, BCL-6 rearrangements may be considered the first identified genetic lesion specific for the DLCL type among AIDS-NHL. BCL-6 rearrangements are present in both subgroups of DLCL, i.e. LNCCL and LC-IBPL, and occur both in the absence and in the presence of EBV infection of the tumor clone (Table 4). On the other hand, BC.L-6 rearrangements were never detected in AIDS-DLCL carrying c-MYC alterations (Table 4).

The molecular pathway leading to AIDS-SNCCL involves c-MYC rearrangements, p53 mutations, and EBV infection in 100%, 60%, and 40% of the cases, respectively (13–26). The presence of somatic hypermutation in the immunoglobulin variable regions utilized by AIDS-SNCCL points to chronic antigen stimulation as an additional mechanism in the development of these tumors. The second genetic pathway is associated with AIDS-DLCL, involves EBV in the large majority of cases, as well as c-MYC and/or BCL-6 rearrangements in a fraction of cases (13–26). These distinct pathogenetic mechanisms correlate with a number of clinical features which distinguish AIDS-SNCCL from AIDS-DLCL, including different age of onset and different CD4 counts at the time of lymphoma development (1,2,8). Results suggest that the frequency of BCL-6 rearrangements in AIDS-DLCL is significantly lower than that in DLCL in the immunocompetent host, where BCL-6 rearrangements occur in more than 40% of the cases. It is possible that the genetic pathogenesis of these two groups of tumors is different, and that the molecular mechanisms active in AIDS-DLCL are characterized by a higher degree of heterogeneity. Among DLCL in the immunocompetent host, BCL-6 rearrangements are associated with distinct clinical features, including the extranodal origin of the lymphoma and the lack of bone marrow involvement. In addition, the presence of this rearrangement appears to represent a favorable prognostic marker.

REFERENCES FOR SECTION IV

1. Karp, J. E., and Broder, S. (1991) Acquired Immunodeficiency Syndrome and non-Hodgkin's lymphomas, *Cancer Res.* 51:4743.
2. Levine, A. M. (1992) Acquired Immunodeficiency Syndrome-related lymphoma, *Blood* 80:8.
3. Gaidano, G., and Dalla-Favera, R. (1992) Biologic aspects of human immunodeficiency virus-related lymphoma, *Curr. Opinion Oncol.* 4:900.
4. Ziegler, J. L., et al. (1982) Outbreak of Burkitt's like lymphoma in homosexual men, *Lancet* 2:631.
5. Ragni, M. V., et al. (1993) Acquired immunodeficiency syndrome-associated non-Hodgkin's lymphomas and other malignancies in patients with hemophilia, *Blood* 81:1889.
6. Gail, M. H., et al. (1991) Projection of the incidence of non-Hodgkin's lymphoma related to acquired immunodeficiency syndrome, *J. Natl. Cancer Inst.* 83:965.
7. Raphael, B. G., and Knowles, D. M. (1990) Acquired. immunodeficiency syndrome-associated lymphomas, *Sermin. Oncol.* 17:361.
8. Beral, V., et al. (1991) AIDS-associated non-Hodgkin lymphoma, *Lancet* 337:805.
9. Knowles, D. M., et al. (1988) Lymphoid neoplasia associated with the acquired immunodeficiency syndrome (AIDS), *Ann. Int. Med.* 108:744.
10. Levine, A. M., et al. (1984) Development of B-cell lymphoma in homosexual men, *Ann. Intern. Med.* 100:7.
11. Carbone, A., et al. (1991) A clinicopathologic study of lymphoid neoplasias associated with human immunodeficiency virus infection in Italy, *Cancer* 68:842.
12. Ioachim, H. L., et al. (1991) Acquired immunodeficiency syndrome-associated lymphomas:
    Clinical, pathologic, immunologic, and viral characteristics of 111 cases, *Hum. Pathol.* 22:659.
13. Ballerini, P., et al. (1993) Multiple genetic lesions in acquired immunodeficiency syndrome-related non-Hodgkin's lymphoma, *Blood* 81:166.
14. Gaidano, G., et al. (1993) In vitro establishment of AIDS-related lymphoma cell lines: phenotypic characterization, oncogene and tumor suppressor gene lesions, and heterogeneity in Epstein-Barr virus infection, *Leukemia* 7:1621.
15. Groopman, J. E., et al. (1986) Pathogenesis of B-cell lymphoma in a patient with AIDS, *Blood* 67:612.
16. Pelicci, P.-G., et al. (1986) Multiple monoclonal B cell expansions and c-myc oncogene rearrangements in acquired immune deficiency syndrome-related lymphoproliferative disorders. Implications for lymphomagenesis, *J. Exp. Med.* 164:2049.
17. Subar, M., et al. (1988) Frequent c-myc oncogene activation and infrequent presence of Epstein-Barr Virus genome in AIDS-associated lymphoma, *Blood* 72:667.
18. Haluska, F. G., et al. (1989) Molecular resemblance of an AIDS-associated lymphoma and endemic Burkitt lymphomas: implications for their pathogenesis, *Proc. Natl. Acad. Sci. USA* 86:8907.
19. Meeker, T. C., et al. (1991) Evidence for molecular subtypes of HIV-associated lymphoma: division into peripheral monoclonal, polyclonal and central nervous system lymphoma, *AIDS* 5:669.
20. Epstein-Barr virus and AIDS associated lymphomas. Editorial, *Lancet* 338:979, (1991).
21. Hamilton-Dutoit, S. J., et al. (1991) Detection of Epstein-Barr virus genomes in AIDS related lymphomas: sensitivity and specificty of in situ hybridization compared with Southern blotting, *J. Clin. Pathol.* 44:676.
22. Hamilton-Dutoit, S. J., et al. (1991) AIDS-related lymphoma. Histopathology, immunophenotype, and association with Epstein-Barr virus as demonstrated by in situ nucleic acid hybridization, *Am. J. Pathol.* 138:149.
23. Neri, A., et al. (1991) Epstein-Barr virus infection precedes clonal expansion in Burkitt's and acquired immunodeficiency syndrome-associated lymphoma, *Blood* 77:1092.
24. Nakamura, H., et al. (1993) Mutation and protein expression of p53 in acquired immunodeficiency syndrome-related lymphomas, *Blood* 82:920.
25. Carbone, A., et al. (1993) Human immunodeficiency virus-associated systemic lymphomas may be subdivided into two main groups according to Epstein-Barr viral latent gene expression, *J. Clin. Oncol.* 1:1674.
26. Ye, B. H., et al. (1993) Cloning of BCL-6, the locus involved in chromosome translocations affecting band 3q27 in B-cell lymphoma, *Cancer Res.* 53:2732.
27. Ye, B. H., et al. (1993) Alterations of a zinc finger-encoding gene, BCL-6, in diffuse large cell-lymphoma, *Science* 262:747.
28. Baron, B. W., et al. (1993) Identification of the gene associated with the recurring chromosomal translocations t(3;14)(q27;q32) and t(3;22) (q27;q11) in B-cell lymphomas, *Proc. Natl. Acad. Sci. USA* 90:5262.
29. Kerckaert, J.-P., et al. (1993) LAZ3, a novel zinc-finger encoding gene, is disrupted by recurring chromosome 3q27 translocations in human lymphoma, *Nature Genet.* 5:66.
30. Deweindt, C., et al. (1993) Cloning of a breakpoint cluster region at band 3q27 involved in human non-Hodgkin's lymphoma, *Genes, Chrom. & Cancer* 8:149.
31 Bastard, C., and Tilly, H. (1993) Response to letter "t(2;3)(p12;q27) in Hodgkin's disease of a human immunodeficiency-virus positive patient with hemophilia", by Schlegelberger B, Grote W, Wacker HH, Bartels H., *Blood* 81:265.
32. Knowles, D. M., et al. (1986) T-cell receptor Beta chain ($T_B$) gene rearrangements: genetic markers of T-cell lineage and clonality, *Hum. Pathol.* 17:546.
33. Miller, S. A., et al. (1988) A simple salting out procedure for extracting DNA from human nucleated cells, *Nucleic Acid Res.* 16:1215.
34. Sambrook, J., et al. (1989) Molecular cloning: a laboratory manual. Cold Spring Harbor, N.Y., Cold Spring Harbor Laboratory.
35. Feinberg, A. P., and Vogelstein, B. (1983) A technique for radiolabeling DNA restriction endonuclease fragments to high specific activity, *Anal. Biochem.* 132:6.
36. Korsmeyer, S. J., et al. (1981) Developmental hierarchy of immunoglobulin gene rearrangement in human leukemic pre-B cells, *Proc. Natl. Acad. Sci. USA* 78:7096.
37. Dalla-Favera, R., et al. (1981) Human c-myc oncogene is located on the region of chromosome 8 that is translocated in Burkitt lymphoma cells, *Proc. Natl. Acad. Sci. USA* 78:7096.
38. Weiss, L. M., et al. (1987) Epstein-Barr virus DNA in tissues of Hodgkin's disease, *Am. J. Path.* 129:86.
39. Chadburn, A., et al. (1993) CD30(Ki-1) positive anaplastic large cell lymphomas in individuals infected with the human immunodeficiency virus, *Cancer* 72:3078.
40. Gaidano, G., et al. (1991) p53 mutations in human lymphoid malignancies: Association with Burkitt lymphoma and chronic lymphocytic leukemia, *Proc. Natl. Acad. Sci. USA* 88:5413.

41. Shibata, D., et al. (1993) Epstein-Barr virus-associated non-Hodgkin's lymphoma in patients infected with the human immunodeficiency virus, *Blood* 81:2102.

EXPERIMENTAL DETAIL SECTION V

Introduction

The group of diffuse lymphomas with a large cell component (DLLC), including diffuse mixed, immunoblastic, and large cell subtypes, and the group of follicular lymphomas, each comprise about 40 per cent of non-Hodgkin's lymphomas (NHL) in this country (1). Together, the incidence of NHL is increasing at 3 to 4 per cont a year, a rate second only to that of malignant melanoma and lung cancer in women (2). Despite significant advances in treatment, approximately half of patients with DLLC will succomb to their disease, although "high risk" individuals may successfully be treated by intensive chemotherapy and radiotherapy regimens including autologous bone marrow transplantation (3–7). The formulation of prognostic models allow clinical trials to be directed toward groups of patients with different risks for failure after conventional treatment (5).

Cytogenetic studies as well as molecular genetic analysis of alterations involving proto-oncogenes and tumor suppressor genes have provided insights into the pathogenesis of NHL, and have also contributed diagnostic and prognostic markers (8,9). Examples include rearrangements of the BCL-2 gene at 18q21 observed in up to 85 per cent of follicular lymphomas, the BCL-1 gene at 11q13 rearranged in intermediate differentiation NHL, and the MYC gene, perturbed in Burkitt's lymphoma (8,9). While no recurring genetic abnormality has been specifically associated with diffuse large cell lymphoma, rearrangement of BCL-2 has been observed in 20 to 30 per cent of cases, where it has been associated with decreased overall or disease free survival (10–12). Chromosomal translocations including those involving the MYC proto-oncogene, while noted in DLLC, were not as prognostically significant as other recurring chromosomal abnormalities (8,13).

BCL-6 (14–19) rearrangement is found to denote a subset of DLLC characterized by extranodal presentation and a favorable clinical outcome. These results indicate that, in concert with other clinical features, this molecular marker may be utilized as a prognostic indicator at the time of diagnosis.

Materials and Methods

This study was comprised of 102 cases of DLLC studied at diagnosis with documented clonal rearrangement of the IGH gene and DNA available for further analysis, derived from 229 DLLC serially ascertained over a nine year period. Excluded were 127 cases studied at relapse, T cell DLLC, or cases for which no DNA was available. For this study, DLLC was defined as lymphomas of diffuse large cleaved, non-cleaved, immunoblastic, or mixed subtype, according to the International Working Formulation (20) as classified by a hematopathologist (DCS or DF). Cytogenetic analysis was attempted on each of the specimens as previously described (21). For detection of BCL-6 rearrangements, DNA from each case was digested with BamHI and XbaI and subjected to Southern blot analysis utilizing a 4 kb Sac1-Sac1 fragment of the BCL-6 gene as a probe (19). Cases which did not yield metaphases for karyotypic analysis were also analyzed for rearrangement of the MBR and MCR breakpoint regions of the BCL-2 gene, as previously described (11). Aggregate descriptions of 47 of the cases in the current series were included in prior reports of cytogenetic abnormalities in DLLC (11, 13, 14). A detailed molecular analysis of 8 cases (nos. 352, 755, 1098, 1254, 1403, 1444, 1445) demonstrating BCL-6 rearrangement has been reported separately (19).

For each case, clinical data were compiled as previously described (22). Stage was assessed according to the modified Ann Arbor criteria (25). For the purposes of separate evaluation of number of extranodal sites of disease, radiographs or pathologic involvement of these sites were scored. In the quantitation of extranodal sites of disease as a prognostic variable, bone marrow, but not splenic involvement was scored, in accord with the International Prognostic Index (5).

Clinical endpoints including complete response and freedom from progression were defined as previously described (3). Of 102 patients with DLLC genetically analyzed prior to cytotoxic treatments, 93 received systemic chemotherapy. Nine patients with early stage disease were treated by surgical resection and/or radiation therapy. All patients were treated with curative intent. Chemotherapy treatments were classified into three groups: NHL-4, CHOP and BACOP (1st generation); m-BACOD, NHL-7 (2nd generation); MBCOP-B, NHL-9, NHL-14, NHL-15, L-20 (3rd generation)(4,24,29). Eight patients expired before completion of therapy, with incomplete staging evaluations, or of infectious complications during or shortly after treatment. These cases were considered not valuable for the determination of remission status, but were included in the analysis of overall survival and freedom from progression. One patient was judged to be a complete remission which was confirmed by autopsy after expiration due to infectious complications 3 weeks after completion of protocol treatment. All deaths, regardless of cause were considered as endpoints in the analysis of overall survival. Median survival was determined by the method of Kaplan and Meler (30). Analysis of correlations between gene rearrangements and clinical features were performed utilizing Fisher's exact test (13). Means were compared utilizing two sample t-tests. Univariate comparisons of survival and duration free from progression were made by log rank test. Survival and freedom from progression estimates are quoted with confidence intervals (CI) given in parentheses. Multivariate analysis was performed utilizing the Cox regression model (31). Stepwise multiple logistic regression was sued in the multivariate analysis of factors prognostic for achieving a complete response. For all statistical analyses, a P<0.05 based on a 2-sided test was considered significant.

Experimental Results

Figure 17A:
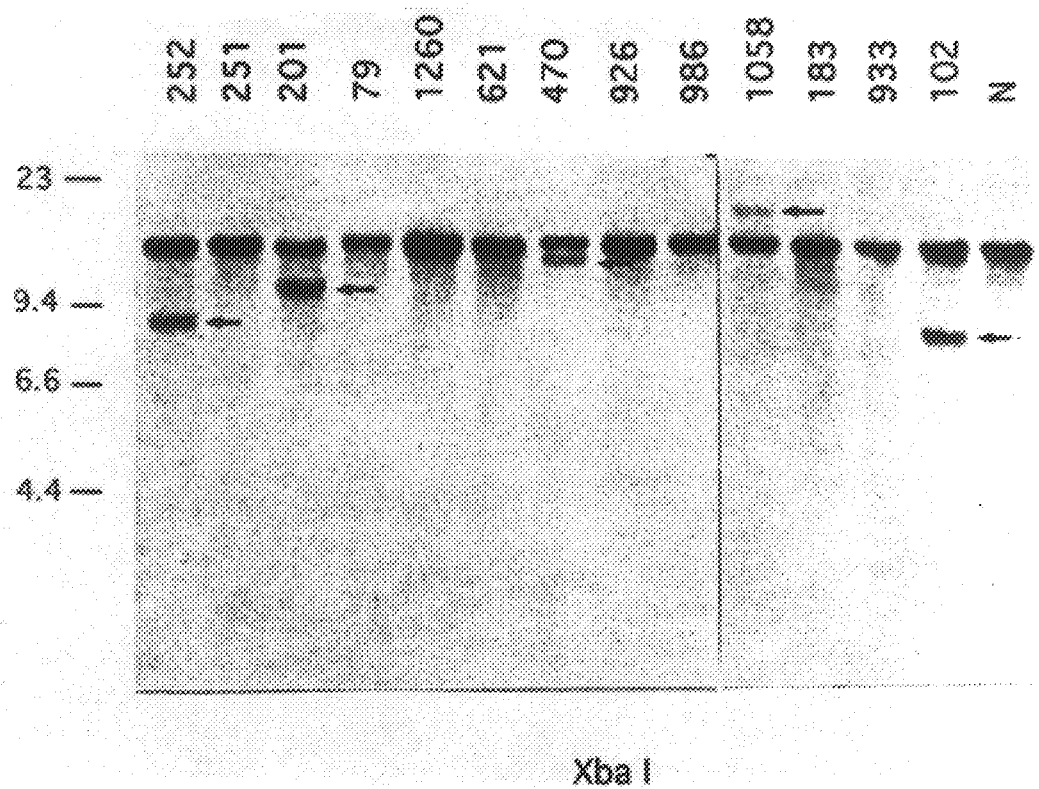
FIGS. 17A–17B: Southern blot analysis of the BCL-6 gene configuration in diffuse large cell lymphomas. Genomic DNA extracted from tumor biopsies was digested with the indicated restriction endonucleases and hybridized using the Sac4.0 probe (19). Rearranged fragments are indicated by the arrows. N=normal control DNA obtained from human lymphocytes.
Figure 17B:
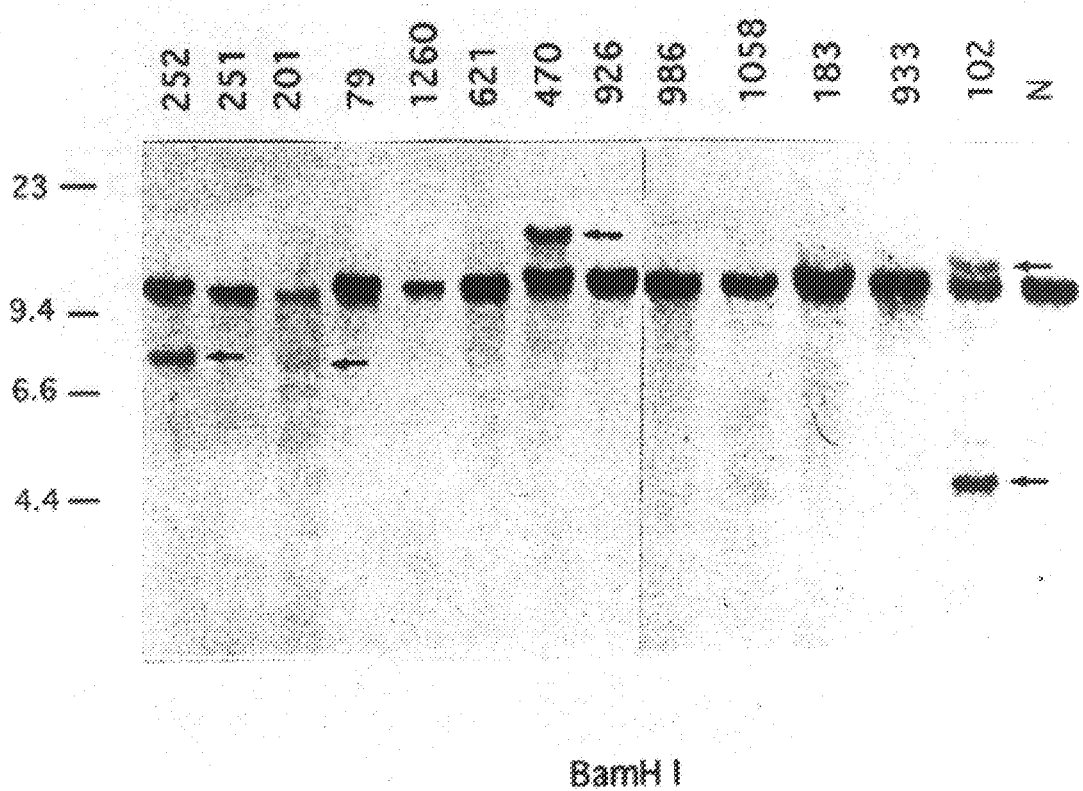

Of 102 cases of DLLC studied at diagnosis, 23 demonstrated BCL-6 rearrangement, 21 demonstrated t(14;18) or rearrangement of BCL-2, and 58 demonstrated no evidence of either BCL-6 or BCL-2 rearrangement. Representative results of hybridization analysis for rearrangement of BCL-6 are depicted in FIGS. 17A–17B. The clinical characteristics of groups according to BCL-6 or BCL-2 rearrangement are summarized in Table 5. The histologic subtypes and clinical features of the BCL-6 rearranged cases are shown in Table 6.

The key to Table 6 is as follows: Underlining signifies site from which biopsy was performed. Histology: DLC=diffuse large cell; IMB-immunoblastic; DML =diffuse mixed lymphoma; LDH=lactate dehydrogenase in units/ml; (B)=bulky disease (>8 cm or ⅓ thoracic diameter); CHOP= cyclophosphamide, daunorubicin, vincristine, prednisone; MACOPB=methotrexate, daunorubicin, cyclophosphamide, vincristine, prednisone, bleomycin; MBACOD=same drugs as MACOPB with dexamethasone instead of prednixone and drugs in different schedule; PrCyBom-drugs of MACOPB plus cytosine arabinoside, etopiside, methotrexate; L-20-vincristine, cyclophosphamide, methotrexate, daunorubicin, prednisone, cytosine arabinoside, 1-asparaginase, BCNU, 6-mercaptopurine, dactinomycin; 1–20 includes randomization to autologous transplantation; NHL-7=CHOP plus methyl GAG, etoposide(36), NHL-14=short course PrCy-Bom; NHL-15=high dose daunorubicin, vincristine, cyclophosphamide(29); RT=radiation therapy; SURG= surgery CR=complete response; sCR=surgical complete response (all evaluable disease resected); PR=partial response; "+"=alive at last follow-up; e=expired; rel= relapse; NE=not evaluable; *=Patient 1445 had a history of low grade NHL of eyelid 7 years earlier, treated by radiotherapy. # Skin involvement of patient 252 was not noted in a prior report (14) and patient 1445 had a history of low grade NHL of eyelid 7 years earlier, treated by radiotherapy.

While each of the BCL-6 rearranged cases was classified as a DLLC, the range of morphologies included diffuse large cell (cleaved and non-cleaved), and less frequently, immunoblastic, or mixed histologies. Extensive necrosis and extranodal extension were common histologic features, and were present in one of two cases of BCL-6 rearrangement which did not show clinical evidence of extranodal disease.

The BCL-6 rearranged cases had a mean age of 64.1 years at presentation and a high frequency of extranodal involvement by disease; 19 of 23 cases had stages IE, IIE, IIIE or stage IV desease, compared to 48 of 79 of BCL-6 germline cases (p+0.07). Extranodal sites included muscle or subcutaneous tissues (6 cases), stomach (5 cases), lung or pleura (5 cases), skin, breast, bowel, thyroid, pancreas, or kidney, as assessed by biopsy or radiographic abnormalities which improved after chemotherapy. Of the 7 cases with state IE or IIE decrease, 5 were primary extranodal lymphomas, while 2 were extranodal extensions from a primary nodal site. Two cases were primary splenic lymphomas. In two cases, there was only peripheral adenopathy. Compared to BCL-6 germline cases, there was no significant difference in the proportion of BCL-6 rearranged cases with stage IV disease. Bone marrow involvement was observed in 15 of 75 BCL-6 germline cases biopsied, compared to only 1 of the 23 stage IV BCL-6 rearranged cases (P=0.1).

All but one of the 23 patients with BCL-6 rearrangement at the time of diagnosis received anthracycline-containing chemotherapy. This patient remained free of disease eight years after resection of a primary splenic large cell lymphoma. At median follow-up in excess of two years, 21 of the 23 patients with BCL-6 rearrangement survived; the actuarial survival was 91 per cent (CI 80 per cent to 100 per cent). Two patients expired during or immediately following treatment; an autopsy in one case revealed no evidence of lymphoma. This patient, and 19 others were judged to have achieved a complete remission after treatment. Two patients relapsed with recurrent disease in the lung and two patients had persistent subcutaneous masses. One of the relapse patients (case 295) went on to autologous transplanation and remains free of disease 78 months post-transplant.

With respect to known prognostic variables, the proportion of the BCL-6 rearranged cohort with LDH>500 U per liter was similar to the proportion of the BCL-6 germline DLLC (3/23 versus 13/79; P=0.99). Five of 23 cases of DLLC with BCL-6 rearrangement demonstrated bulky disease, compared to 35 of 79 cases without BCL-6 rearrangement (P=0.1). The proportion of cases with "limited stage" (I, IE, II, or IIE) disease was comparable in the cohorts with and without BCL-6 rearrangement (Table 5).

TABLE 5

Characteristics of 102 cases of DLLC

|  | BCL-6+ | BCL-6− BCL2− | BCL-6− BCL2+ |
|---|---|---|---|
| n= | 23 | 58 | 21 |
| Mean age (years) | 64.1 | 52.7 | 62.8 |
| Mean lactate dehydrogenase (U/ml) | 405 | 331 | 389 |
| Mean extranodal sites | 1.6 | .93 | .81 |
| Bone marrow involvement | 1/23 | 8/54 | 7/21 |
| Stage |  |  |  |
| I(IE) | 3(1) | 3(3) | 0 |
| II(IIE) | 7(6) | 22(6) | 5 |
| III(IIIE) | 2(1) | 8(2) | 4 |
| IV | 11 | 25 | 12 |
| Histology |  |  |  |
| Diffuse large cell | 20 | 53 | 19 |
| Diffuse mixed | 1 | 2 | 1 |
| Immunoblastic | 2 | 3 | 1 |
| Treatment |  |  |  |
| 1st generation chemo. | 12 | 16 | 10 |
| 2nd generation chemo. | 1 | 10 | 3 |
| 3rd generation chemo. | 9 | 24 | 8 |
| other | 1 | 8 | 0 |
| Complete Remission Rate | 20/23 86% | 35/50 70% | 15/21 71% |
| Projected survival at 36 months | 91% (CI 80%–100%) | 59% (CI 44%–74%) | 46% (CI 21%–72%) |
| Projected freedom from progression at 36 months | 82% (CI 66%–98%) | 56% (CI 43%–70%) | 31% (CI 8%–53%) |

TABLE 6

Clinical features of 23 cases of DLLC with BCL6 rearrangement

| CASE NUMBER | AGE/ SEX | STAGE | EXTRANODAL SITES | HISTOLOGY | LDH (BULK) | TREATMENT | CLINICAL OUTCOME |
|---|---|---|---|---|---|---|---|
| 102 | 66/F | IIS | spleen | DLC | 3624 | SURG,CHOP | CR,96+ |
| 147 | 61/F | IS | spleen | DLC | 365 (B) | SURG,RT | sCR,101+ |
| 252 | 54/M | IV | spleen,skin | DLC | 126 | MACOPB | CR,58+ |
| 278 | 68/M | IV | pleura, iliac mass | DLC | 235 (B) | MACOPB | PR,6e |
| 295 | 46/M | IV | lung | DLC | 179 | MACOPB,L-20 | CR,rel,97+ |
| 352 | 53/F | IV | stomach,liver, spleen,small | IMB | 775 (B) | MACOPB | CR,81+ |

TABLE 6-continued

Clinical features of 23 cases of DLLC with BCL6 rearrangement

| CASE NUMBER | AGE/ SEX | STAGE | EXTRANODAL SITES | HISTOLOGY | LDH (BULK) | TREATMENT | CLINICAL OUTCOME |
|---|---|---|---|---|---|---|---|
| | | | bowel,pleural effasion | | | | |
| 470 | 74/F | IV | lung | DLC | 224 | CHOP | CR,30+ |
| 534 | 70/F | IIES | spleen,mass involving pancreas | DLC | 278 (B) | CHOP | CR,80+ |
| 763 | 79/F | IIE | stomach | DLC | 196 | CHOP | CR,60+ |
| 970 | 75/M | IV | kidney, stomach | DLC | 240 | NHL-14 | CR,4e |
| 1020 | 60/M | IIIE | tonsil, pancreas | DLC | 303 | CHOP | CR,100+ |
| 1056 | 63/M | IIE | stomach | DLC | 213 | SURG,MBACOD | CR,100+ |
| 1058 | 59/M | IIE | axillary pass involving breast | DLC | 206 | PrCyBom | CR,37+ |
| 1098 | 74/F | IV | subcutaneous masses | DML | 181 | RT,CHOP | PR,36+ |
| 1189 | 71/M | IV | subcutaneous masses | DLC | 330 | CHOP | PR,21+ |
| 1254 | 74/F | IIE | thyroid | DLC | 196 | CHOP/RT | CR,27+ |
| 1264 | 76/F | IV | Lung,liver spleen,kidney | DLC | 234 | CHOP | CR,rel,27+ |
| 1299 | 50/M | IE | deltoid mass, bone | DLC | 529 (B) | PrCyBom | CR,16+ |
| 1363 | 47/M | III | NONE | DLC | 129 | NHL-15 | CR,16+ |
| 1403 | 62/M | I | NONE | IMB | 222 | CHOP,RT | CR,11+ |
| 1407 | 71/M | IIE | stomach | DLC | 206 | SURG,CHOP | CR,12+ |
| 1444 | 70/F | IV | lung | DLC | 150 | CHOP | CR,14+ |
| 1445 | 63/F | IV | neck mass involving muscle*,bone marrow | DLC | 174 | NHL-15 | CR,8+ |

Figure 18A:
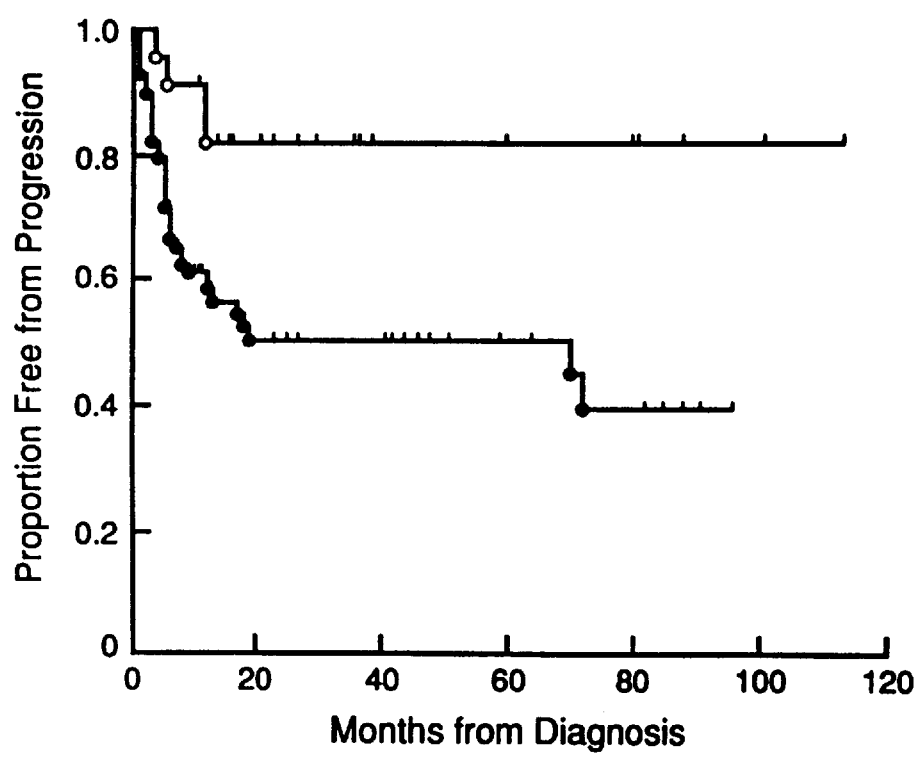
FIGS. 18A–18B.

Multivariate analysts of clinical outcome. The median duration free from progression of disease was not reached in the BCL-6 rearranged DLLC compared to 70 months for BCL-6 germline cases, regardless of BCL-2 status (P=0.009) (FIG. 18A). Projected freedom from progression at 36 months was 82% (CI 66%–98%) and 49% (CI 37%–60%), respectively. Multivariate analysis revealed that four variables, BCL-6 status, stage IV disease, bulk of disease, and LDH (log transformed) were the most powerful prognostic indicators for freedom from progression (Table 7). Multivariate analysis of survival demonstrated that bulk, LDH, BCL-6 status, and stage IV disease were the most useful predictors of overall survival (P=0.01, P=0.02, P=0.02, P=0.05, respectively).

TABLE 7

Multivariate analysis of freedom from progression

| Variables selected into Cox regression model | Relative Risk | P value (Wald chi square) |
|---|---|---|
| BCL-6 rearranged | 0.18 (CI) .04–.78) | 0.007 |
| Bulky disease | 2.4 (CI 1.3–7.4) | 0.01 |
| Stage IV disease | 2.1 (CI 0.98–5.2) | 0.03 |
| LDH (log transformed) | 1.6 (CI 1.1–3.9) | 0.05 |

The prognostic value of BCL-6 gene status was compared to risk variables calculated according to the International Prognostic Index[5], including serum LDH level, stage, performance status, and number of extranodal sites. A cox regression analysis confirmed the independent prognostic value of BCL-6 gene status;

patients with BCL-6 rearrangement had a relative risk (RR) of dying of 0.09 (CI 0.02 to 0.42) compared to patients without BCL-6 rearrangement, controlling for the other prognostic variables in the model (P=0.002).

Figure 18B:
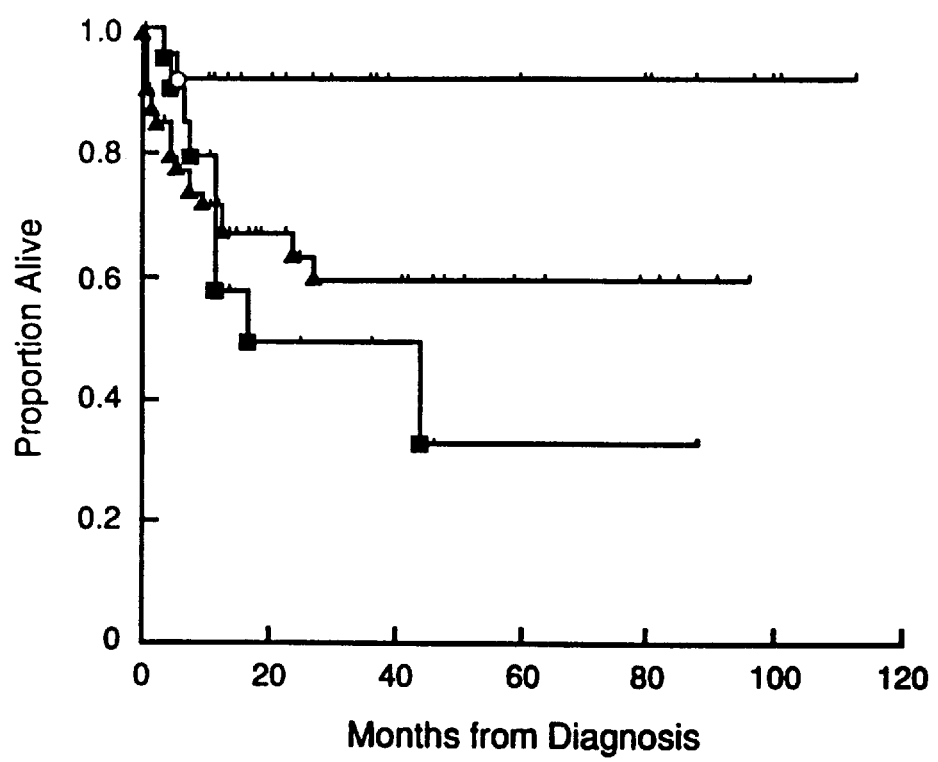

When cases were considered with respect to BCL-2 status, the BCL-2 rearranged cases demonstrated a trend for a decreased survival compared to BCL-2 germline cases, regardless of BCL-6 status (P=0.12). When BCL-6 and BCL-2 status were considered together (FIG. 18B), BCL-6 rearranged cases demonstrated a projected actuarial survival at 36 months of 91% (CI 80%–100%) compared to 59% (CI 44%–74%) for the BCL-6 germline/BCL-2 germline cohort, and 46% (CI 21%–72%) for the BCL-2 rearranged cohort. While the logrank test between these three cohorts demonstrated a difference in survival (P=0.02, FIG. 18B), the major factor driving the significant summary P value was the better survival of the BCL-6 rearranged cohort. The projected freedom from progression at 36 months was 82% (CI 66%–98%), 56% (CI 43%–70%) and 31% (CI 8%–53%) for the three groups. Median follow-up for survivors was two years. BCL-2 rearrangement did not emerge as an independent prognostic marker in the multivariate analysis of survival or freedom from progression.

There was also no prognostically significant effect of generation of chemotherapy treatment on survival, or freedom from progression (P=0.95, 0.21, respectively). There was a trend for a higher complete response rate among the BCL-6 rearranged cohort (Table 5, P=0.1), although logistic regression revealed that only the clinical parameters LDH, stage IV, and bulk of disease were independent predictors of response.

Relationship between BCL-6, BCL-2, and 8q24 rearrangements. Of the 79 cases which lacked BCL-6 rearrangement, 21 demonstrated t(14;18) (q32;q21) or rearrangement of BCL-2 by molecular analysis. These cases were characterized by an older age at diagnosis, but were similar to the larger cohort of BCL-2 negative, BCL-6 negative cases with respect to LDH, and distribution of histologies (Table 6).

Nine cases of DLLC demonstrated t(8;14) (q24;q32). Three of these biopsies were from extranodal sites including liver, bone and soft tissue. Two additional cases were splenic lymphomas. In two cases, t(8;14) bearing DLLC also demonstrated BCL-6 rearrangement. There was no impact on survival of the t(8;14) in DLLC with or without BCL-6 rearrangement. The two cases of t(8;14) with co-incident BCL-6 rearrangement did not show evidence of histologic transformation or other unusual histologic features. One of these cases (no. 147) was the single case treated by splenectomy and radiation therapy alone. The second case was the single BCL-6 rearranged case successfully salvaged by autologous transplantation.

Cytogenetic features, including the relationship between 3q27 and BCL-6 rearrangement. Of the 65 DLLC with karyotypic abnormalities, 14 demonstrated translocations and one a deletion affecting band 3q27; only 11 among these 15 cases showed rearrangement of BCL-6 Five cases with apparently normal chromosomes 3 demonstrated BCL-6 rearrangements by DNA analysis.

Experimental Discussion

As a group, DLLC are among the most common forms of NHL seen in this country (1). These tumors have not, however, been associated with a characteristic genetic abnormality (8). Seen in the vast majority of follicular lymphomas, t(14;18) (q32;q21) or its molecular equivalent, BCL-2 rearrangement, have been observed in 20 to 30 per cent of DLLC (8). In such cases, the t(14;18) may reflect a follicular origin of these tumors. The recognition of translocations involving 3q27 and the sites of IG genes, 14q32, 22q11, and 2p12, in predominantly diffuse NHL led to the molecular cloning of BCL-6 (14–19). While not unique to diffuse large cell lymphomas, translocations affecting 3q27 were observed only in 7 of>200 cases of follicular NHL with abnormal karyotype reported in catalog of chromosome abnormalities in cancer (32). Of 28 cases of follicular NHL analyzed in a prior study, none demonstrated rearrangement of BCL-6 (19). BCL-6 rearrangement was established as the most common genetic lesion specific to DLLC at the time of diagnosis.

Unlike 18q21 translocations in NHL, which to date only have involved IG gene loci as reciprocal partners, 3q27 translocations demonstrated a marked promiscuity of rearrangement partners. In addition to the sites of the IG genes, reciprocal translocations involving the 3q27–29 region with at least 12 other loci; a total of 79 DLLC with 3q27 translocations has been demonstrated.

Since 4 tumors in the current series with documented 3q27 aberrations did not reveal BCL-6 rearrangement with the probe used in this study, the true frequency of BCL-6 rearrangement in DLLC at diagnosis may be higher than the 23 per cent rate reported here. Additional breakpoints may be documented outside the recognized break cluster region of BCL-6 (19), in neighboring genes such as EV-1 (34), or in other genes not yet described. Such molecular heterogeneity is not unique in NHL; seemingly identical chromosomal translocations have been shown to demonstrate a diversity of breakpoints possibly involving different genes (35).

The frequent occurrence of BCL-6 rearrangement in DLLC characterized by extranodal involvement represents one of the few genetic markers for this subset of lymphoma (8). Rearrangements of BCL-1, BCL-2, or BCL-3 have been documented infrequently in extranodal lymphomas (36–38), while 5 of 12 gastric lymphomas in one series demonstrated MYC (8q24) rearrangement (38). The current series did not confirm the association between 8q24 rearrangement and gastric lymphoma, although t(8;14) was seen in five cases of extranodal lymphoma, one of which also showed BCL-6 rearrangement. The proportion of BCL-6 rearranged cases with stages IE, IIE, IIIE, or IV disease was higher than the proportion of BCL-6 germline DLLC; in the latter group, stage IV disease was more commonly due to bone marrow involvement. Whether this association with extranodal involvement of disease reflects an effect of the primary deregulation of BCL-6 or "secondary" genetic events associated with tumor progression (8,21) is unclear. The observation of t(3;22), t(2;3), or t(3;14) as solitary cytogenetic abnormalities in some tumors (14,15), is consistent with a primary pathogenetic role for this translocation.

While this analysis and two other reports did not confirm the very short survival of BCL-2 rearranged DLLC initially reported (10, 12, 13, 39), the BCL-2 rearranged DLLC did demonstrate a trend for a poorer overall survival. The finding of a favorable prognosis for the subset of stage IE-IIE extranodal DLLC with BCL-6 rearrangement is consistent with prior reports of a good prognosis associated with localized extranodal large cell NHL treated with surgery or radiotherapy (40). Extranodal involvement in advanced stage disease, noted in the majority of the BCL-6 rearranged cases, has generally been considered a poor prognostic factor in large series of DLLC, although the negative impact of this feature was most evident when combined with other adverse indicators such as bulk, high LDH, or low performance status (5, 22, 41). In contrast, bone marrow involvement, observed in 22 percent of DLLC, and considered an extranodal site in the International Prognostic Index (5), was rare in the BCL-6 rearranged cohort. The favorable treatment outcome of the BCL-6 cohort, must also be tempered by the observation of relapse or residual disease in 3 of the patients still alive. An additional relapse case remains in remission 6 years after "salvage" autologous transplantation.

The BCL-6 rearranged cohort of DLLC also possessed other clinical markers of favorable prognosis; although comparable with respect to LDH and proportion with stage I-IIIE disease, the proportion of cases with bulky disease or bone marrow involvement was lower in the BCL-6 rearranged cohort. Multivariate analysis suggested, however, that BCL-6 gene rearrangement added independent prognostic power when analyzed together with clinically-derived variables of the International Prognostic Index (5). This observation is illustrated by case 352, which displayed both BCL-6 rearrangement as well as clinical features consistent with a high level of risk in the International Index (elevated LDH, extensive extranodal involvement, low performance status, and stage IV disease), but who attained a durable remission.

Because of issues of toxicity versus efficacy of autologous bone marrow transplantation or peripheral stem cell rescue, the identification of both favorable and unfavorable prognostic markers offers the potential to stratify treatment approaches to DLLC based on risk groups (4–7, 22, 41). The probability of treatment failure remains as high as 25–40 per cent for the most favorable subsets of DLLC based on current prognostic models, highlighting the need for genetic or other prognostic markers (5). In addition to its potential diagnostic and prognostic applications, the further identification of BCL-6 breakpoint regions offers the opportunity to develop new polymerase chain reaction-derived measures of minimal residual disease (43). The availability of BCL-6 rearrangement as a new molecular marker of large cell lymphoma constitutes a potentially important clinical tool in the management of patients with this desease.

REFERENCES FOR SECTION V

1. Simon, R., et al. (1988) The non-Hodgkin's lymphoma pathologic classification project; Longterm follow-up of 1153 patients with non-Hodgkin's lymphoma, *Ann. Internal. Med.* 109:939–945.
2. Devesa, S. S., and Fears, T. (1992) Non-Hodkin's lymphoma time trends: United States and international data, *Cancer Res.* 52:5432–40.
3. Fisher, R. I., et al. (1993) Comparison of a standard regimen (CHOP) with three intensive chemotherapy regimens for advanced non-Hodgkin's lymphoma, *N. Engl. J. Med.* 328:1002–6.
4. Armitage, J. O. (1993) Treatment of non-Hodgkin's lymphoma, *N. Engl. J. Med.* 328:1023–30.
5. A predictive model for aggressive non-Hodgkin's lymphoma. The International Non-Hodgkin's lymphoma prognostic factors project, *N. Engl. J. Med.* 329:987–94.
6. Gulati, S. C., et al. (1988) Autologous bone marrow transplantation for patients with poor-prognosis lymphoma, *J. Clin. Oncol.* 6:1303–13.
7. McMaster, M. L., et al. (1991) Results of treatment with high intensity, brief duration chemotherapy in poor prognosis non-Hodgkin's lymphoma, *Cancer* 68:233–41.
8. Offit, K., and Chaganti, R. S. K. (1991) Chromosomal aberrations in non-Hodgkin's lymphoma: biological and clinical correlations, *Hematol. Oncol. Clin. North Am.* 5:853–869.
9. McKeithan, T. W. (1990) Molecular biology of non-Hodgkin's lymphomas, *Semin. Oncol.* 1:30–42.
9. Yunis, J. J., (1989) bcl-2 and other genomic alterations in the prognosis of large-cell lymphoma, *N. Engl. J. Med.* 320:1047–54.
10. Offit, K., et al. (1989) 18q21 rearrangement in diffuse large cell lymphoma: incidence and clinical significance, *Br. J. Haematol.* 72:178– 83.
11. Jacobson, J. O., et al. (1993) bcl-2 rearrangements in de novo diffuse large cell lymphoma, *Cancer* 72:231–6.
12. Offit, K., et al. (1991) Cytogenetic analysis of 434 consecutively ascertained specimens of non-Hodkin's lymphoma: clinical correlations, *Blood* 77:1508–15.
13. Offit, K., et al. (1989) t(3;22)(q27;q11): A novel translocation associated with diffuse non-Hodgkin's lymphoma, *Blood* 74:1876–79.
14. Bastard, C., et al. (1992) Translocations involving band 3q27 and Ig gene regions in non-Hodgkin's lymphoma, *Blood* 79:2527–31.
15. Ye, B. H., et al. (1993) Cloning of bcl6, the locus involved in chromosome translocations affecting band 3q27 in B-cell lymphoma, *Cancer Res.* 53:2732–35.
16. Baron, B. W., et al. (1993) Identification of the gene associated with the recurring chromosomal translocations t(3;14)(q27;q32) and t(3;22)(q27;q11) in B-cell lymphomas, *Proc. Natl. Acad. Sci.* 90:5262–66.
17. Kerckaert, J.-P., et al. (1993) LAZ3, a novel zinc-finger encoding gene, is disrupted by recurring chromosome 3q27 translocations in human lymphomas, *Nat. Genet.* 5:66–70.
18. Ye, B. H., et al. (1993) Alterations of a novel zinc-finger encoding gene, bcl-6, in diffuse large-cell lymphoma, *Science* 262:747–750.
19. The non-Hodkin's lymphoma pathologic classification project. National Cancer Institute sponsored study of classification of non-Hodkin's lymphomas: summary and description of a working formulation for clinical usage, *Cancer* 49:2112–35.
20. Offit, K., et al. (1991) Cytogenetic analysis of 434 consecutively ascertained specimens of non-Hodkin's lymphoma: correlations between recurrent aberrations, histology, and exposure to cytotoxic treatment, *Genes Chromosom. Cancer* 3:189–201.
21. Danieu, L., et al. (1986) Predictive model for prognisis in advanced diffuse histiocytic lymphoma, *Cancer Res.* 46:5372–79.
22. Carbone, P. P., et al. (1971) Report of the committee on Hodgkin's disease staging classification, *Cancer Res.* 31:1860–61.
23. Kempin, S., et al. (1983) Combined modality therapy of advanced nodular lymphomas, *Proc. Annu. Meet. Am. Soc. Clin. Oncol.* 2:56.
24. Carrato, A., et al. (1987) Randomized comparison of CHOP versus Bleo CHOP for the treatment of diffuse NHL, *Proc. Annu. Meet. Am. Soc. Clin. Oncol.* 6:779.
25. Lowenthal, D. A., et al. (1987) The NHL-7 protocol: Alternating non-cross resistant chemotherapy containing methyl-GAG for diffuse non-Hodkin's lymphoma, *Proc. Annu. Meet. Am. Soc. Clin. Oncol.* 6:778.
26. Warrell, R. P., et al. (1989) Short term intensive treatment of intermediate-grade non-Hodkin's lymphoma using infusional chemotherapy, *Proc. Annu. Meet. Am. Soc. Clin. Oncol.* 8:1054.
27. Straus, D. H., et al. (1991) Small non-Cleaved cell lymphoma (undifferentiated lymphoma/Burkitt's type) in American adults. Results with treatment designed for acute lymphoblastic leukemia in adults, *Am. J. Med.* 90:328–337.
28. O'Brien, J., et al. (1992) NHL-15 protocol for diffuse aggressive lymphomas: a dose intense regimen of doxorubicin, vincristine, and cyclophosphamide, *Blood* 80:157a.
29. Kaplan, E. L., and Meier, P. (1958) Nonparametric estimation from incomplete observations, *J. Am. Stat. Soc.* 53:457–81.
30. Cox, D. R. Regression models and life tables, *J. R. Stat. Soc. B.* 34:187–220.
31. Mitelman, F. (1991) Catalog of chromosome aberrations in cancer, New York.
32. Leroux, D., et al. (1990) Translocation t(3;22) (q27;q11) in three patients with diffuse large B cell lymphoma, *Leukemia* 4:373–376.
33. Fichelson, S., et al. (1992) Evi-1 expression in leukemic patients with rearrangements of the 3q25–q28 chromosomal region, *Leukemia* 6:93–99.
34. Ladanyi M, et al. (1992) Follicular lymphoma with t(8;14)(q24;q32). A distinct clinical and molecular subset of t(8;14)-bearing lymphomas, *Blood* 79:2124–30.
35. Raghoebier, S., et al. (1991) Essential differences in oncogene involvement between primary nodal and extranodal large cell lymphoma, *Blood* 78:2680–86.
36. Clark, H. M., et al. (1992) Cytogenetic and molecular studies of t(8;14) and t(14;19) in nodal and extranodal b:cell lymphoma, *J. Pathol.* 166:129–37.
37. Van Krieken, J. H. J. M., et al. (1991) Molecular genetics of gastrointestinal non-Hodkin's lymphomas: unusual prevalence and pattern of c-myc rearrangements in aggressive lymphomas, *Blood* 76:797–800.
38. Romaguera, J. E., et al. (1993) The clinical relevance of t(14;18)/bcl-2 rearrangement and del 6q in diffuse large cell lymphoma and immunoblastic lymphoma, *Ann. Oncol.* 4:51–4.
39. Rudders, R. A., et al. (1978) Primary extranodal lymphoma: Response to treatment and factors influencing prognosis. *Cancer* 42:406–16.

40. Coiffier, B., et al. (1991) Prognostic factors in aggressive malignant lymphomas: description and validation of a prognostic index that could identify patients requiring a more intensive therapy, *J. Clin. Oncol.* 9:211–19.
41. Schneider, A. M., et al. (1990) Treatment results with an aggressive chemotherapeutic regimen (MACOP-B) for intermediate and some high grade non-Hodkin's lymphomas, *J. Clin. Oncol.* 8:94–102.
42. Gribben, J. G., et al. (1993) Detection by polymerase chain reaction of residual cells with the BCl-2 translocation is associated with increased risk of relapse after autologous bone marrow transplantation for b-cell lymphoma, *Blood* 81:3449–87.

What is claimed is:

1. A method for detecting a rearrangment of a bcl-6 gene in B-cell lymphoma in a subject, comprising:
   (a) obtaining a DNA sample from the subject;
   (b) cleaving the DNA sample into fragments;
   (c) seperating the DNA fragments by size fractionation;
   (d) hybidizing the DNA fragments with a nucleic acid molecule comprising at least 15 contiguous nucleotides which is complementary to a sequence of an isolated nucleic acid molecule having the nucleic acid sequence as set forth in SEQ ID NO:1 and specifically hybridizes with the nucleic acid sequence as set forth in SEQ ID NO:1 to detect the DNA fragment containing the bcl-6 nucleic acid sequence; and
   (e) comparing the detected DNA fragment from (d) with a DNA fragment from a known normal subject, the difference in size of the fragments indicating occurrence of a rearrangement of the bcl-6 gene in B-cell lymphoma in the subject.

2. The method of claim 1, where in step (b), the DNA sample is cleaved by restriction enzyme.

3. The method of claim 1, wherein the size fractionation is step (c) is effected by a polyacrylamide or agarose gel.

4. The method of claim 1, where in step (d), the nucleic acid molecule is labeled with a detectable marker.

5. The method of claim 4, wherein the detectable marker is a radiolabelled molecule, a fluorescent molecule, an enzyme, or a ligand.

6. The method of claim 1, further comprising transferring the DNA fragments into a solid matrix before step (d).

7. A method for detecting a rearrangement of a bcl-6 gene in B-cell lymphoma in a subject, comprising:
   (a) obtaining an RNA sample from the subject;
   (b) separating the RNA sample into different species by size fractionation;
   (c) hybridizing the RNA species with a nucleic acid molecule comprising at least 15 contiguous nucleotides which is complementary to a sequence of an isolated nucleic acid molecule having the nucleic acid sequence as set forth in SEQ ID NO:1 and specifically hybridizes with the nucleic acid sequence as set forth in SEQ ID NO:1 to detect the RNA species containing bcl-6 nucleic acid sequence; and
   (d) comparing the detected RNA species from step (c) with the RNA species from a known normal subject, the difference in size of the species indicating the rearrangement of the bcl-6 gene in B-cell lymphoma in the subject.

8. The method of claim 7, wherein the size fractionation in step (b) is effected by a polyacrylamide or agarose gel.

9. The method of claim 7, where in step (c), the nucleic acid molecule is labeled with a detectable marker.

10. The method of claim 9, wherein the detectable marker is a radiolabelled molecule, a fluorescent molecule, an enzyme, or a ligand.

11. A method of claim 7, further comprising transferring the RNA species into a solid matrix before step (c).

* * * * *